United States Patent
Cong et al.

(10) Patent No.: US 9,688,721 B2
(45) Date of Patent: *Jun. 27, 2017

(54) TUBULYSIN COMPOUNDS, METHODS OF MAKING AND USE

(71) Applicant: Bristol-Myers Squibb Company, Princeton, NJ (US)

(72) Inventors: Qiang Cong, Palo Alto, CA (US); Heng Cheng, Foster City, CA (US); Sanjeev Gangwar, Foster City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/171,592

(22) Filed: Jun. 2, 2016

(65) Prior Publication Data
US 2016/0264624 A1    Sep. 15, 2016

Related U.S. Application Data

(60) Continuation of application No. 14/605,549, filed on Jan. 26, 2015, now Pat. No. 9,382,289, which is a division of application No. 14/177,376, filed on Feb. 11, 2014, now Pat. No. 8,980,824.

(60) Provisional application No. 61/764,825, filed on Feb. 14, 2013.

(51) Int. Cl.

| | |
|---|---|
| A61K 38/00 | (2006.01) |
| C07K 5/117 | (2006.01) |
| A61K 47/48 | (2006.01) |
| C07K 7/06 | (2006.01) |
| C07K 5/10 | (2006.01) |
| A61K 38/07 | (2006.01) |
| C07K 5/06 | (2006.01) |
| C07K 5/078 | (2006.01) |
| A61K 38/05 | (2006.01) |
| C07K 5/107 | (2006.01) |

(52) U.S. Cl.
CPC ............ *C07K 5/1024* (2013.01); *A61K 38/05* (2013.01); *A61K 38/07* (2013.01); *A61K 47/48246* (2013.01); *A61K 47/48415* (2013.01); *A61K 47/48569* (2013.01); *A61K 47/48592* (2013.01); *A61K 47/48607* (2013.01); *A61K 47/48615* (2013.01); *A61K 47/48638* (2013.01); *C07K 5/06* (2013.01); *C07K 5/06139* (2013.01); *C07K 5/06165* (2013.01); *C07K 5/10* (2013.01); *C07K 7/06* (2013.01); *C07K 5/1016* (2013.01)

(58) Field of Classification Search
CPC .. A61K 38/05; A61K 38/07; A61K 47/48246; A61K 47/48415; A61K 47/48569; A61K 47/48592; A61K 47/48607; A61K 47/48615; A61K 47/48638; C07K 5/06; C07K 5/06139; C07K 5/06165; C07K 5/10

See application file for complete search history.

(56) References Cited

U.S. PATENT DOCUMENTS

| | | |
|---|---|---|
| 6,214,345 B1 | 4/2001 | Firestone et al. |
| 6,984,720 B1 | 1/2006 | Korman et al. |
| 6,989,452 B2 | 1/2006 | Ng et al. |
| 7,087,600 B2 | 8/2006 | Ng et al. |
| 7,129,261 B2 | 10/2006 | Ng et al. |
| 7,335,748 B2 | 2/2008 | Harkins et al. |
| 7,375,078 B2 | 5/2008 | Feng |
| 7,387,776 B2 | 6/2008 | Keler et al. |
| 7,517,903 B2 | 4/2009 | Chen et al. |
| 7,691,962 B2 | 4/2010 | Boyd et al. |
| 7,714,016 B2 | 5/2010 | Gangwar |
| 7,847,105 B2 | 12/2010 | Gangwar et al. |
| 7,875,278 B2 | 1/2011 | Cardarelli et al. |
| 7,968,586 B2 | 6/2011 | Gangwar et al. |
| 8,008,449 B2 | 8/2011 | Korman et al. |
| 8,097,703 B2 | 1/2012 | Rao-Naik et al. |

(Continued)

FOREIGN PATENT DOCUMENTS

| | | |
|---|---|---|
| DE | 10008089 | 10/2001 |
| DE | 102004030227 | 1/2006 |

(Continued)

OTHER PUBLICATIONS

PatBase abstract of WO 98/13375.
PatBase abstract of DE 102004030227.
PatBase abstract of DE 10008089.
Steinmetz, H. et al., "Isolation, Crystal and Solution Structure Determination, and Biosynthesis of Tubulysins-Powerful Inhibitors of Tubulin Polymerization from Myxobacteria", Angew. Chem. Int. Ed., vol. 43, pp. 4888-4892 (2004).

(Continued)

*Primary Examiner* — Marcela M Cordero Garcia
(74) *Attorney, Agent, or Firm* — Yuan Chao

(57) ABSTRACT

Tubulysin compounds of the formula (I)

(I)

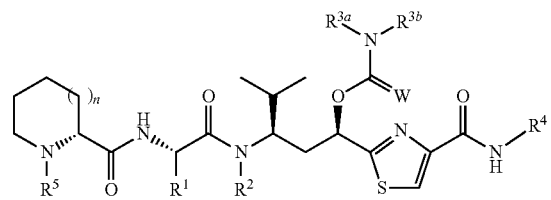

where $R^1$, $R^2$ $R^{3a}$, $R^{3b}$, $R^4$, $R^5$, W, and n are as defined herein, are anti-mitotic agents that can be used in the treatment of cancer, especially when conjugated to a targeting moiety.

1 Claim, 28 Drawing Sheets

(56) References Cited

U.S. PATENT DOCUMENTS

| | | | |
|---|---|---|---|
| 8,124,738 B2 | 2/2012 | Terret et al. | |
| 8,268,970 B2 | 9/2012 | Terrett et al. | |
| 8,383,779 B2 | 2/2013 | Terrett et al. | |
| 8,476,451 B2 | 7/2013 | Ellman et al. | |
| 8,580,820 B2 | 11/2013 | Zanda et al. | |
| 8,980,824 B2* | 3/2015 | Cong | A61K 47/48246 424/179.1 |
| 9,109,008 B2* | 8/2015 | Cong | A61K 47/48246 |
| 9,382,289 B2* | 7/2016 | Cong | A61K 47/48246 |
| 2002/0169125 A1 | 11/2002 | Leung et al. | |
| 2003/0096743 A1 | 5/2003 | Senter et al. | |
| 2005/0239713 A1 | 10/2005 | Domling et al. | |
| 2005/0249740 A1 | 11/2005 | Domling et al. | |
| 2006/0128754 A1 | 6/2006 | Hoefle et al. | |
| 2006/0217360 A1 | 9/2006 | Hoefle et al. | |
| 2008/0176958 A1 | 7/2008 | Davis et al. | |
| 2008/0248052 A1 | 10/2008 | Vlahov et al. | |
| 2008/0279868 A1 | 11/2008 | Boyd et al. | |
| 2009/0074660 A1 | 3/2009 | Korman et al. | |
| 2009/0297438 A1 | 12/2009 | Huang et al. | |
| 2010/0034826 A1 | 2/2010 | Terrett et al. | |
| 2010/0047841 A1 | 2/2010 | Wipf et al. | |
| 2010/0048490 A1 | 2/2010 | Vlahov et al. | |
| 2010/0092484 A1 | 4/2010 | Xu et al. | |
| 2010/0093024 A1 | 4/2010 | Goerke et al. | |
| 2010/0113476 A1 | 5/2010 | Chen et al. | |
| 2010/0143368 A1 | 6/2010 | King et al. | |
| 2010/0145036 A1 | 6/2010 | Sufi et al. | |
| 2010/0150950 A1 | 6/2010 | Coccia et al. | |
| 2010/0209432 A1 | 8/2010 | Terrett et al. | |
| 2010/0240701 A1 | 9/2010 | Vlahov et al. | |
| 2010/0323973 A1 | 12/2010 | Leamon et al. | |
| 2010/0324008 A1 | 12/2010 | Low et al. | |
| 2011/0027274 A1 | 2/2011 | Cheng et al. | |
| 2011/0245295 A1 | 10/2011 | Chai et al. | |
| 2012/0129779 A1 | 5/2012 | Wichter | |
| 2012/0252739 A1 | 10/2012 | Wichter | |
| 2013/0224228 A1 | 8/2013 | Jackson et al. | |

FOREIGN PATENT DOCUMENTS

| | | |
|---|---|---|
| EP | 2292639 A1 | 3/2011 |
| WO | WO 81/01145 | 4/1981 |
| WO | WO 97/21712 | 6/1997 |
| WO | WO 98/13375 | 4/1998 |
| WO | WO 02/096910 | 12/2002 |
| WO | WO 2005/051976 | 6/2005 |
| WO | WO 2008/030612 | 3/2008 |
| WO | WO 2008/083312 | 7/2008 |
| WO | WO 2010/087994 | 8/2010 |
| WO | WO 2011/069116 | 6/2011 |
| WO | WO 2012/010287 | 1/2012 |

OTHER PUBLICATIONS

Domling, A. et al., "Total Synthesis of Tubulysin U and V", Angew. Chem. Int. Ed., vol. 45, pp. 7235-7239 (2006).

Sani, M. et al, "Total Synthesis of Tubulysin U and V", Angew. Chem. Int. Ed., vol. 46, pp. 3526-3529 (2007).

Ullrich, A. et al, "Pretubulysin, a Potent and Chemically Acc3essible Tubulysin Precursor from Angiococcus Disciformis", Angew. Chem. Int. Ed., vol. 48, pp. 4422-4425 (2009).

Jeger, S. et al, "Site-Specific and Stoichiometric Modification of Antibodies by Bacterial Transglutaminase", Angew. Chem. Int. Ed., vol. 49, pp. 39995-9997 (2010).

Michael D. B., "Click Chemistry and Bioorthogonal Reactions: Unprecedented Selectivity in the Labeling of Biological Molecules", Biochemistry., vol. 48, pp. 6571-6584 (2009).

Kaur, G. et al., "Biological Evaluation of Tubulysin A: A Potential Anti cancer and Antiangiogenic Natural Product", Biochem J.., vol. 396, pp. 235-242 (2006).

Dubowchik, G. et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity", Bioconjugate Chem., vol. 13, pp. 855-869 (2002).

Dubowchik, G. et al., "Cathepsin B-Sensitive Dipeptide Prodrugs. 1. A Model Study of Structural Requirements for Efficient Release of Doxorubicin", Bioorganic & Medicinal Chemistry Letters, vol. 8, pp. 3341-3346 (1998).

Dubowchik, G. et al., "Cathepsin B-Sensitive Dipeptide Prodrugs. 2. Models of Anticancer Drugs Paclitaxel (Taxol®), Mitomycin C and Doxorubicin", Bioorganic & Medicinal Chemistry Letters, vol. 8, pp. 3347-3352 (1998).

Balasubramanian, R. et al., "Tubulysin Analogs Incorporating Desmethyl and Dimethyl Tubuphenylalanine Derivatives", Bioorganic & Medicinal Chemistry Letters, vol. 18, pp. 2996-2999 (2008).

Iontcho R., V. et al., "Design and Regioselective Synthesis of a New Generation of Targeted Chemotherapeutics. Part II: Folic Acid Conjugates of Tubulysins and Their Hydrazides", Bioorganic & Medicinal Chemistry Letters, vol. 18, pp. 4558-4561 (2008).

Shibue, T. et al., "Synthesis and Biological Evaluation of Tubulysin D. Analogs Related to Steroisomers of Tubuvaline", Bioorganic & Medicinal Chemistry Letters, vol. 21, pp. 431-434 (2011).

Vlahov, I. et al., "Acid Mediated Formation of an N-Acyliminium Ion from Tubulysins: A New Methodology for the Synthesis of Natural Tubulysins and Their Analogs", Bioorganic & Medicinal Chemistry Letters, vol. 21, pp. 6778-6781 (2011).

Goerke, A. et al., "High-Level Cell-Free Synthesis Yields of Proteins Containing Site-Specific Non-Natural Amino Acids", Biotechnology and Bioengineering, vol. 102, pp. 400-416 (2009).

Thomas P., "Sortase-Mediated Protein Ligation: An Emerging Biotechnology Tool for Protein Modification and Immobilisation", Biotechnol Letters, vol. 32, pp. 1-10 (2010).

Leamon, C. et al., "Folate Targeting Enables Durable and Specific Antitumor Responses from a Therapeutically Null Tubulysin B Analogue", Cancer Research, vol. 68, pp. 9839-9844 (2008).

Khalil, M. et al., "Mechanism of Action of Tubulysin, An Antimitotic Peptide from Myxobacteria", ChemBioChem, vol. 7, pp. 678-683 (2006).

Chai, Y. et al., "Discovery of 23 Natural Tubulysins from Angiococcus Disciformis an d48 and Cystobacter SBCb004", Chemistry & Biology 17, vol. 17, pp. 296-309 (2010).

Wang, Z. et al., "Structure-Activity and High-Content Imaging Analyses of Novel Tubulysins", Chem Biol Drug Des, vol. 70, pp. 75-86 (2007).

Shibue, T. et al., "Total Syntheses of Tubulysins", Chemistry Eur. J., vol. 16, pp. 11678-11688 (2010).

Patterson, A. et al., "Design, Synthesis, and Biological Properties of Highly Potent Tubulysin D. Analogues", Chemistry Eur. J., vol. 13, pp. 9534-9541 (2007).

Neri, D. et al., "Efforts Toward the Total Synthesis of Tubulysins: New Hopes for a More Effective Targeted Drug Delivery to Tumors", Chem Med Chem., vol. 1, pp. 175-180 (2006).

Schluep, T. et al., "Polymeric Tubulysin-Peptide Nanoparticles With Potent Antitumor Activity", Clin Cancer Res, vol. 15, pp. 181-189 (2009).

Hemel, E. et al., "Antimitotic Peptides and Depsipeptides", Curr. Med. Chem—Anti-Cancer Agents, vol. 2, pp. 19-53 (2002).

Balasubramanian, R. et al., "Total Synthesis and Biological Evaluation of Tubulysin U, Tubulysin V, and Their Analogues", J. Med. Chemistry, vol. 52, pp. 238-240 (2009).

Agard, N. et al., "A Strain-Promoted [3+2] Azide-Alkyne Cycloaddition for Covalent Modification of Biomolecules in Living Systems", J. Am. Chem., vol. 126, pp. 15046-15047 (2004).

Peltier H. et al., "The Total Synthesis of Tubulysin D", J. Am. Chem., vol. 128, pp. 16018-16019 (2006).

Pando O. et al., "The Multiple Multicomponent Approach to Natural Product Mimics: Tubugis, N-Substituted Anticancer Peptides with Picomolar Activity", J. Am. Chem., vol. 133, pp. 7692-7695 (2011).

Sasse, F. et al., "Tubulysins, New Cytostatic Peptides from Myxobacteria Acting on Microtubuli", J. Antibiotics, vol. 53, pp. 879-885 (2000).

Carl, P. et al., "A Novel Connector Linkage Applicable in Prodrug Design", J. Medicinal Chemistry, vol. 24, pp. 479-480 (1981).

(56) References Cited

OTHER PUBLICATIONS

Toki B. et al., "Protease-Mediated Fragmentation of p-Amidobenzyl Ethers: A New Strategy for the Activation of Anticancer Prodrugs", J. Org. Chemistry, vol. 67, pp. 1866-1872 (2002).
Patterson A. et al., "Expedient Synthesis of N-Methyl Tubulysin Analogues with High Cytotoxicity", J. Org. Chemistry, vol. 73, pp. 4362-4369 (2008).
Domling A. et al., "Myxobacterial Epothilones and Tubulysins as Promising Anticancer Agents", Molecular Diversity, vol. 9, pp. 141-147 (2005).
Reddy J. et al., "In Vivo Structural Activity and Optimization Studies of Folate-Tubulysin Conjugates", Molecular Pharmaceutics, vol. 6 pp. 1518-1525 (2009).
Doronina S. O. et al., "Development of Potent Monoclonal Antibody Auristatin Conjugates for Cancer Therapy", Nature Biotechnology, vol. 21 pp. 778-784 (2003).
Sasse F. et al., "Success in Tubulysin D Synthesis", Nature Chemical Biology, vol. 3 pp. 87-89 (2007).
Schrama D. et al., "Antibody Targeted Drugs as Cancer Therapeutics", Nature Reviews Drug Discovery, vol. 5 pp. 147-159 (2006).
Shankar S.P. et al., "Synthesis and Structure-Activity Relationship Studies of Novel Tubulysin U Analogues—Effect on Cytotoxicity of Structural Variations in the Tubuvaline Fragment", Organic & Biomolecular Chemistry vol. 11 pp. 2273-2287 (2013).
Lundquist J. T. et al., "Improved Solid-Phase Peptide Synthesis Method Utilizing r-Azide-Protected Amino Acids", Organic Letters vol. 3 pp. 781-783 (2001).
Wipf P. et al., "Synthesis of the Tubuvaline-Tubuphenylalanine", Organic Letters vol. 6 pp. 4057-4060 (2004).
Wipf P. et al., "Synthesis of the Tubuvaline-Total Synthesis of N14-Desacetoxytubulysin H", Organic Letters vol. 9 pp. 1605-1607 (2007).
Dubowchik G. M. et al., "Receptor-Mediated and Enzyme-Dependent Targeting of Cytotoxic Anticancer Drugs", Pharmacology & Therapeutics vol. 83 pp. 67-123 (1999).
Levary D.A. et al., "Protein-Protein Fusion Catalyzed by Sortase A", PLOS One vol. 6 pp. 1-6 (2011).
Hofle G. et al., "Semisynthesis and Degradation of the Tubulin Inhibitors Epothilone and Tubulysin", Pure and Applied Chemistry vol. 75 pp. 167-178 (2003).
Shankar S.P. et al., "Studies Towards a Novel Synthesis of Tubulysins: Highly Asymmetric Aza-Michael Reactions of 2-Enoylthiazoles with Metalated Chiral Oxazolidinones", SynLett vol. 8 pp. 1341-1345 (2009).
Shankar S.P. et al., "Total Synthesis and Cytotoxicity Evaluation of an Oxazole Analogue of Tubulysin U", SynLett vol. 12 pp. 1673-1676 (2011).
Shibue T. et al., "Stereoselective Synthesis of Tubuvaline Methyl ester and Tubuphenylalanine, Components of Tubulysins, Tubulin Polymerization Inhibitors", Tetrahedron Letters vol. 50 pp. 3845-3848 (2009).
International Search Report and Written Opinion, mailed Apr. 7, 2014, for PCT Application No. PCT/US2014/015503.

\* cited by examiner

TUBULYSIN COMPOUNDS, METHODS OF MAKING AND USE

CROSS-REFERENCE TO RELATED APPLICATIONS

This application is a continuation of allowed application Ser. No. 14/605,549, filed Jan. 26, 2015; which is a divisional of application Ser. No. 14/177,376, filed Feb. 11, 2014, now U.S. Pat. No. 8,980,824 B2, granted Mar. 17, 2015; which claims the benefit under 35 U.S.C. §119(e) of U.S. Provisional Application No. 61/764,825, filed Feb. 14, 2013, the disclosures of which are incorporated herein by reference.

SEQUENCE LISTING

Incorporated herein by reference in its entirety is a Sequence Listing named "SEQT_12026USCNT.txt," comprising SEQ ID NO:1 through SEQ ID NO:26, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Jan. 4, 2014, and is approximately 15 KB in size.

BACKGROUND OF THE INVENTION

This invention relates to compounds structurally similar to the tubulysins, conjugates thereof with a ligand, methods for making and using such compounds and conjugates, and compositions comprising such compounds and conjugates.

The tubulysins are cytotoxins originally isolated from cultures of the myxobacteria *Archangium gephyra* or *Angiococcus disciformis*, with each organism producing a different mixture of tubulysins (Sasse et al. 2000; Reichenbach et al. 1998). Their crystal structure and biosynthetic pathway have been elucidated (Steinmetz et al. 2004) and their biosynthesis genes have been sequenced (Hoefle et al. 2006b). Pretubulysin, a biosynthetic precursor of the tubulysins, also has been shown to possess some activity (Ullrich et al. 2009). (Full citations for the documents cited herein by first author or inventor and year are listed at the end of this specification.)

The tubulysins belong to a group of naturally occurring antimitotic polypeptides and depsipeptides that includes the phomopsins, the dolastatins, and the cryptophycins (Hamel 2002). Antimitotic agents other than polypeptides or depsipeptides also exist, for example paclitaxel, the maytansines, and the epothilones. During mitosis, a cell's microtubules reorganize to form the mitotic spindle, a process requiring the rapid assembly and disassembly of the microtubule constituent proteins α- and β-tubulin. Antimitotic agents block this process and prevent a cell from undergoing mitosis. At the molecular level the exact blockage mechanism may differ from one anti-mitotic agent to another. The tubulysins prevent the assembly of the tubulins into microtubules, causing the affected cells to accumulate in the $G_2/M$ phase and undergo apoptosis (Khalil et al. 2006). Paclitaxel effects the same end result by binding to microtubules and preventing their disassembly.

The tubulysins have a tetrapeptidyl scaffold constructed from one proteinogenic and three non-proteinogenic amino acid subunits as shown in formula (A): N-methylpipecolinic acid (Mep), isoleucine (Ile), tubuvaline (Tuv), and either tubuphenylalanine (Tup, R' equals H) or tubutyrosine (Tut, R' equals OH). Among the better-known naturally occurring tubulysins (designated A, B, etc.), the sites of structural variation are at residues R', R" and R'" of formula (A), as shown in Table 1:

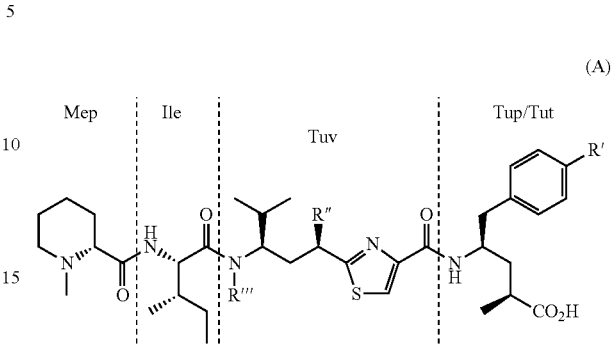

(A)

TABLE 1

Naturally Occurring Tubulysins

| Tubulysin | R' | R" | R'" |
|---|---|---|---|
| A | OH | OC(=O)Me | CH$_2$OC(=O)i-Bu |
| B | OH | OC(=O)Me | CH$_2$OC(=O)n-Pr |
| C | OH | OC(=O)Me | CH$_2$OC(=O)Et |
| D | H | OC(=O)Me | CH$_2$OC(=O)i-Bu |
| E | H | OC(=O)Me | CH$_2$OC(=O)n-Pr |
| F | H | OC(=O)Me | CH$_2$OC(=O)Et |
| G | OH | OC(=O)Me | CH$_2$OC(=O)CH=CH$_2$ |
| H | H | OC(=O)Me | CH$_2$OC(=O)Me |
| I | OH | OC(=O)Me | CH$_2$OC(=O)Me |
| U | H | OC(=O)Me | H |
| V | H | OH | H |
| Y | OH | OC(=O)Me | H |
| Z | OH | OH | H |
| Pretubulysin | H | H | Me |

Additionally, other naturally occurring tubulysins have been identified (Chai et al. 2010).

Kaur et al. 2006 studied the antiproliferative properties of tubulysin A and found that it was more potent than other antimitotic agents such as paclitaxel and vinblastine and was active in xenograft assays against a variety of cancer cell lines. Further, tubulysin A induced apoptosis in cancer cells but not normal cells and showed significant potential antiangiogenic properties in in vitro assays. The antimitotic properties of other tubulysins also have been evaluated and generally have been found to compare favorably against those of non-tubulysin antimitotic agents (see, e.g., Balasubramanian et al. 2009; Steinmetz et al. 2004; Wipf et al. 2004). For these reasons, there is considerable interest in the tubulysins as anti-cancer agents (see, e.g., Domling et al. 2005c; Hamel 2002).

Numerous publications describe efforts directed at the synthesis of tubulysins, including: Balasubramanian et al. 2009; Domling et al. 2006; Hoefle et al. 2003; Neri et al. 2006; Peltier et al. 2006; Sani et al. 2007; Sasse et al. 2007; Shankar et al. 2009; Shibue et al. 2009 and 2010; and Wipf et al. 2004. Other publications describe structure-activity relationship (SAR) studies, via the preparation and evaluation of tubulysin analogs or derivatives: Balasubramanian et al. 2008 and 2009; Chai et al. 2011; Domling 2006; Domling et al. 2005a; Ellman et al. 2013; Hoefle et al. 2001 & 2006a; Pando et al. 2011; Patterson et al. 2007 & 2008; Richter 2012a, 2012b, and 2012c; Shankar et al. 2013; Shibue et al. 2011; Sreejith et al. 2011; Vlahov et al. 2010a; Wang et al.

2007; Wipf et al. 2007 and 2010; and Zanda et al. 2013. The SAR studies mainly explored structural variations in the Mep ring, residues R" and R'" of the Tuv subunit, and the aromatic ring or aliphatic carbon chain of the Tup/Tut subunit.

Domling et al. 2005 disclose conjugates of tubulysins with a partner molecule generically described as a polymer or a biomolecule, but with examples limited to polyethylene glycol (PEG) as the partner molecule. Cheng et al. 2011 also disclose tubulysin analogs adapted for use in conjugates. Other documents disclosing conjugates of tubulysins are Boyd et al. 2008 and 2010; Jackson et al. 2013; Vlahov et al. 2008a, 2008b and 2010b; Leamon et al. 2008 and 2010; Reddy et al. 2009; and Low et al. 2010. Leung et al. 2002 disclose polyanionic polypeptides that can be conjugated to drugs (including tubulysins) to improve their bioactivity and water solubility.

Davis et al. 2008 and Schluep et al. 2009 disclose cyclodextrin based formulations in which tubulysins are covalently attached to a cyclodextrin via a hydrazide-disulfide linker moiety bonded to the Tup/Tut carboxyl group.

The deacetylation of the Tuv subunit (i.e., R" in formula (A) is hydroxyl instead of acetyl) reportedly leads to loss of biological activity (Domling et al. 2006). In a study of tubulysins U and V, which differ in the former being acetylated and the latter being deacetylated, tubulysin V was reported to be less potent by about 200× to 600×, depending on the assay (Balasubramanian et al. 2009). Because an acetate group is susceptible to hydrolysis, deacetylation at the R" position is a concern, as a potential instability center leading to loss of activity, for the development of tubulysin analogs for pharmaceutical applications.

BRIEF SUMMARY OF THE INVENTION

We have discovered that it is possible to guard against the loss of biological activity associated with deacetylation as discussed above by replacing an acetate at the R" position with a carbamate group. A carbamate group as described herein does not cause significant loss of biological activity but yet is more stable.

Accordingly, in one aspect, this invention provides a compound having a structure represented by formula (I)

(I)

wherein
$R^1$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, or unsubstituted or substituted alkylaryl;

$R^2$ is H, unsubstituted or substituted $C_1$-$C_{10}$ alkyl, unsubstituted or substituted $C_2$-$C_{10}$ alkenyl, unsubstituted or substituted $C_2$-$C_{10}$ alkynyl, unsubstituted or substituted aryl, unsubstituted or substituted heteroaryl, unsubstituted or substituted $(CH_2)_{1-2}O(C_1$-$C_{10}$ alkyl), unsubstituted or substituted $(CH_2)_{1-2}O(C_2$-$C_{10}$ alkenyl), unsubstituted or substituted $(CH_2)_{1-2}O(C_2$-$C_{10}$ alkynyl), $(CH_2)_{1-2}OC(=O)(C_1$-$C_{10}$ alkyl), unsubstituted or substituted $(CH_2)_{1-2}OC(=O)(C_2$-$C_{10}$ alkenyl), unsubstituted or substituted $(CH_2)_{1-2}OC(=O)(C_2$-$C_{10}$ alkynyl), unsubstituted or substituted $C(=O)(C_1$-$C_{10}$ alkyl), unsubstituted or substituted $C(=O)(C_2$-$C_{10}$ alkenyl), unsubstituted or substituted $C(=O)(C_2$-$C_{10}$ alkynyl), unsubstituted or substituted cycloaliphatic, unsubstituted or substituted heterocycloaliphatic, unsubstituted or substituted arylalkyl, unsubstituted or substituted alkylaryl, or wherein each $R^{2a}$ is independently H, $NH_2$, NHMe, Cl, F, Me, Et, or CN;

$R^{3a}$ and $R^{3b}$ are independently H, $C_1$-$C_5$ alkyl, $CH_2(C_5$-$C_6$ cycloalkyl), $CH_2C_6H_5$, $C_6H_5$, or $CH_2CH_2OH$;

$R^4$ is wherein $R^{4a}$ is H or $C_1$-$C_3$ alkyl; and Y is H, OH, Cl, F, CN, Me, Et, $NO_2$, or $NH_2$;

$R^5$ is H, $C_1$-$C_5$ alkyl, $C_2$-$C_5$ alkenyl, $C_2$-$C_5$ alkynyl, $CO(C_1$-$C_5$ alkyl), $CO(C_2$-$C_5$ alkenyl), or $CO(C_2$-$C_5$ alkynyl);

W is O or S (preferably O); and n is 0, 1, or 2;

or a pharmaceutically acceptable salt thereof.

In another embodiment, this invention provides a conjugate comprising a compound according to formula (I) covalently linked to a targeting moiety that specifically or preferentially binds to a chemical entity on a target cell, which target cell preferably is a cancer cell. Preferably, the targeting moiety is an antibody—more preferably a monoclonal antibody and even more preferably a human monoclonal antibody—or the antigen-binding portion thereof and the chemical entity is a tumor associated antigen. the tumor associated antigen can be one that is displayed on the surface of a cancer cell or one that is secreted by a cancer cell into the surrounding extracellular space.

In another embodiment, there is provided a composition of matter comprising a compound of this invention and a linker moiety having a reactive functional group, suitable for conjugation to a targeting moiety.

In another embodiment, there is provided a method of treating a cancer in a subject suffering from such cancer, comprising administering to the subject a therapeutically effective amount of a compound of this invention or a conjugate thereof with a targeting moiety (particularly an antibody). In another embodiment, there is provided the use of a compound of this invention or a conjugate thereof with a targeting moiety (particularly an antibody) for the preparation of a medicament for the treatment of cancer in a subject suffering from such cancer. The cancer can be renal, gastric, lung, or ovarian cancer.

BRIEF DESCRIPTION OF THE DRAWING(S)

FIGS. 1, 2a-2b, and 3 show, in combination, a scheme for the synthesis of compound (III-1).

FIGS. 16a, 16b, 17a, 17b, 18a, 18b, 19a, 19b, and 20 present additional in vivo data on the activity of conjugates of this invention.

Figure 21:
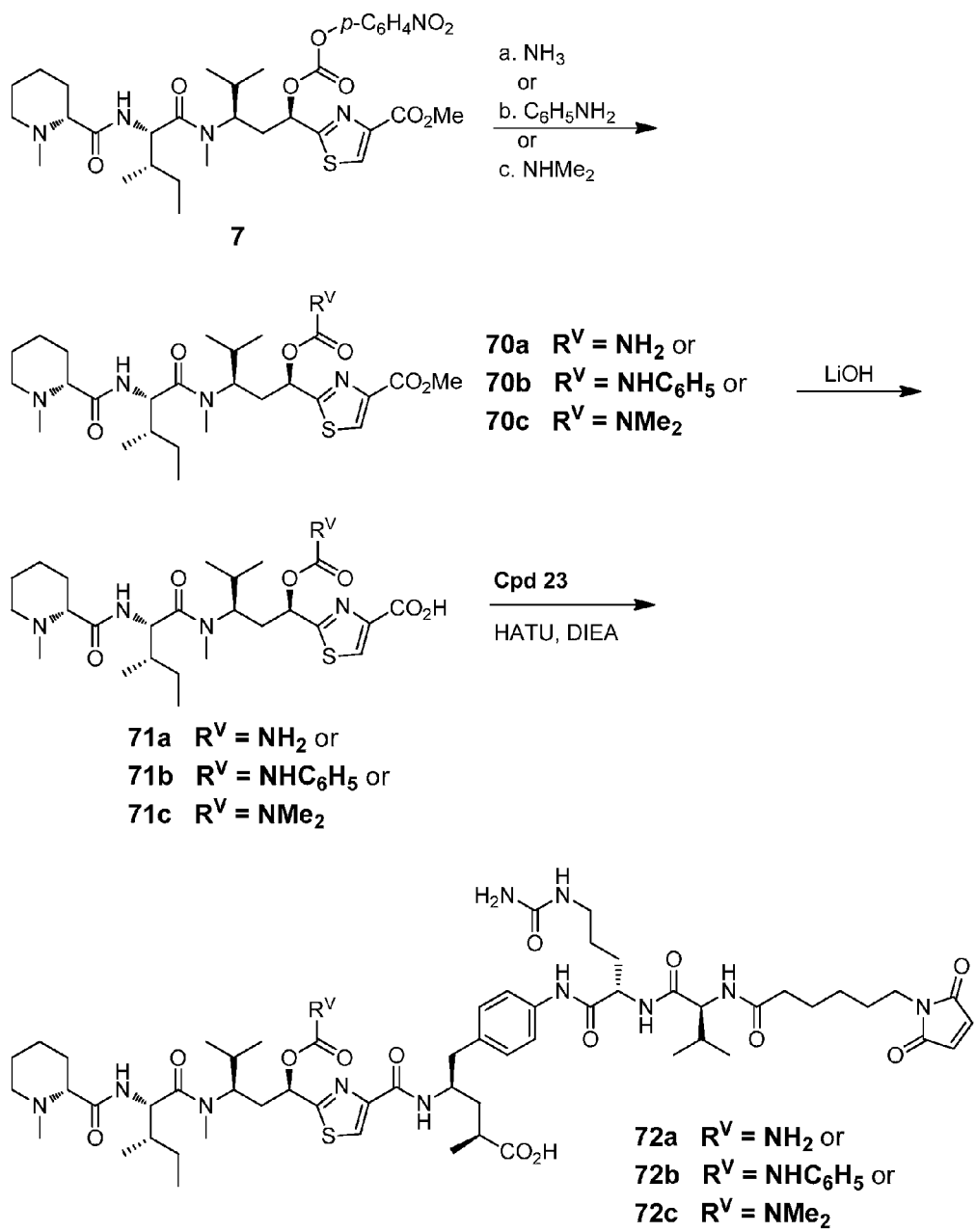
Figure 22:
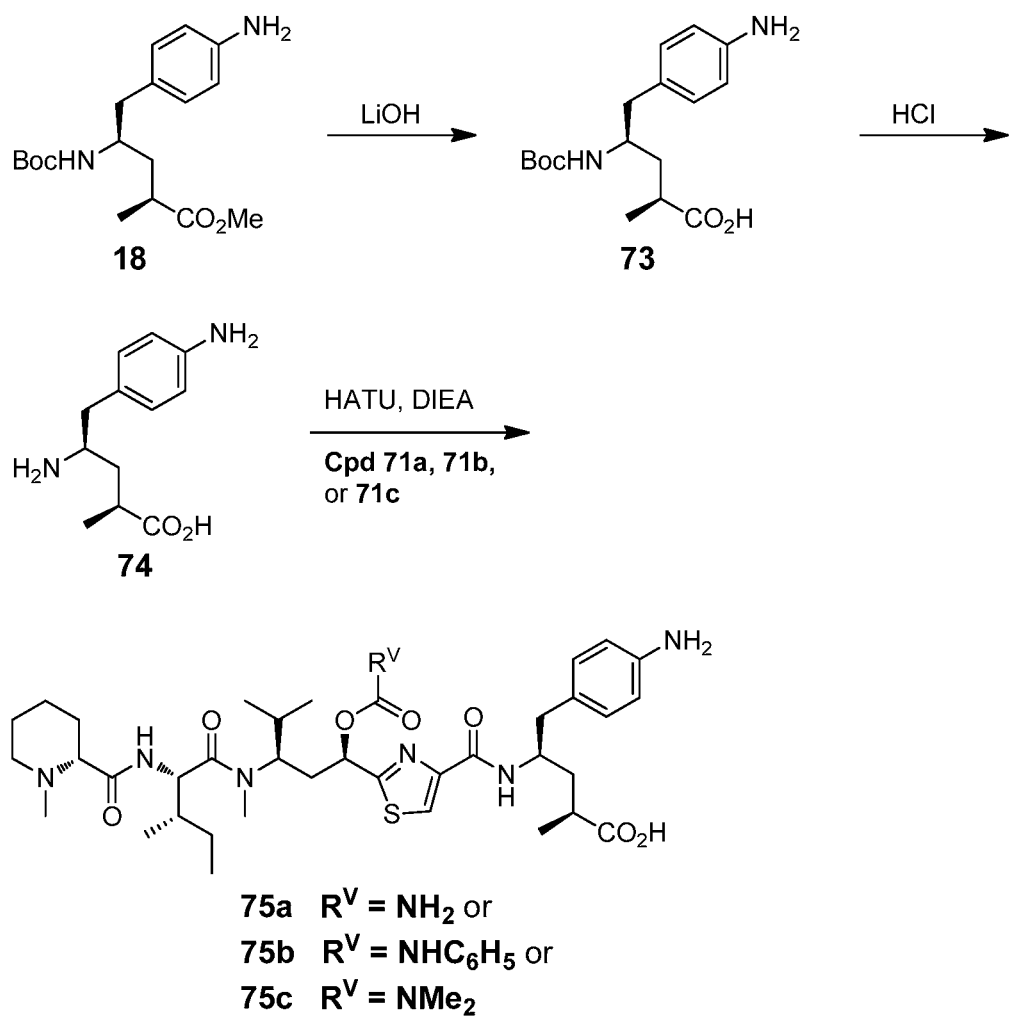

FIGS. 21 and 22 show schemes for the synthesis of additional compounds of this invention, illustrating structural variations at the carbamate group.

Figure 23:
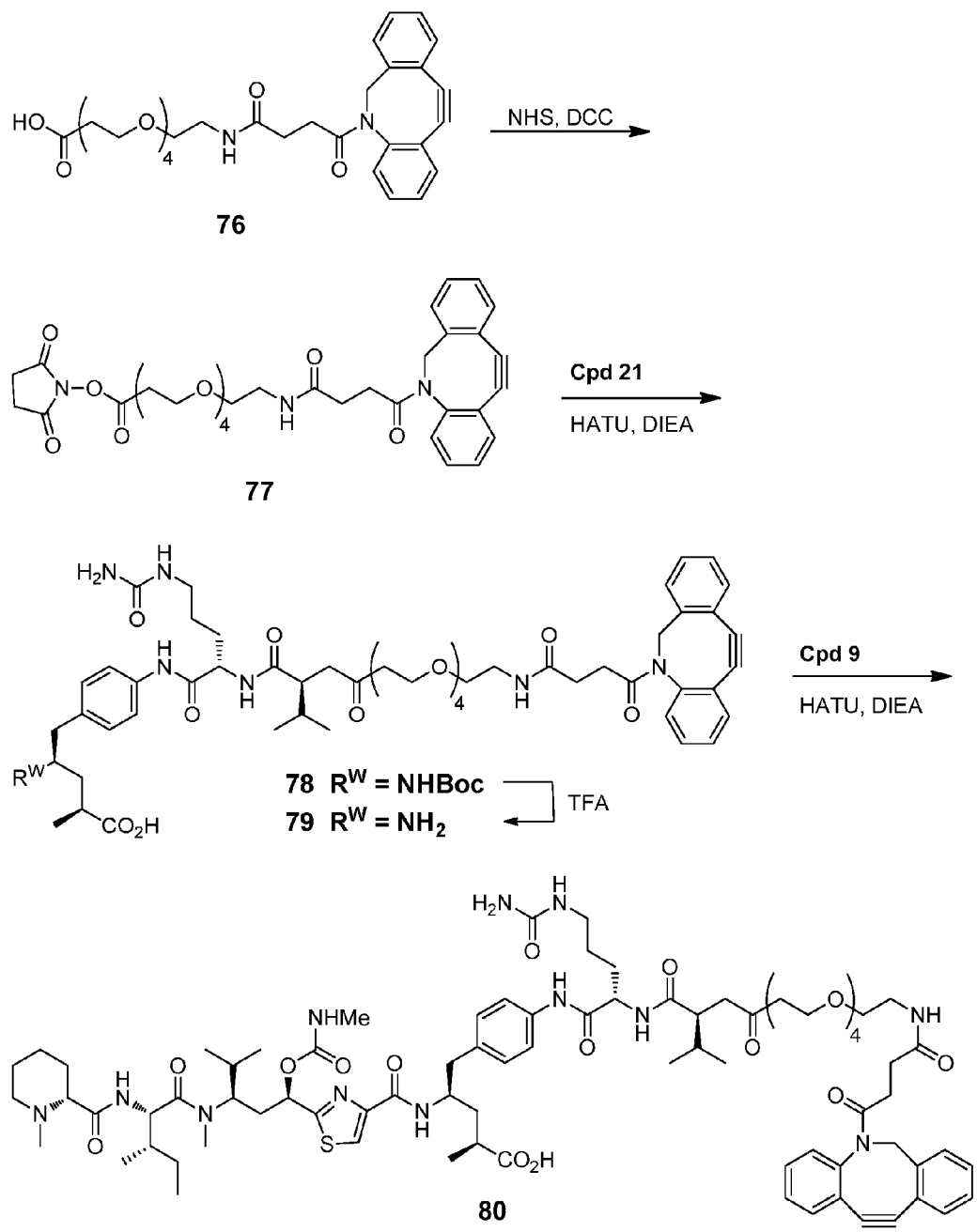

FIG. 23 shows a scheme for the synthesis of compounds of this invention suitable for conjugation via "click" chemistry.

Figure 24:
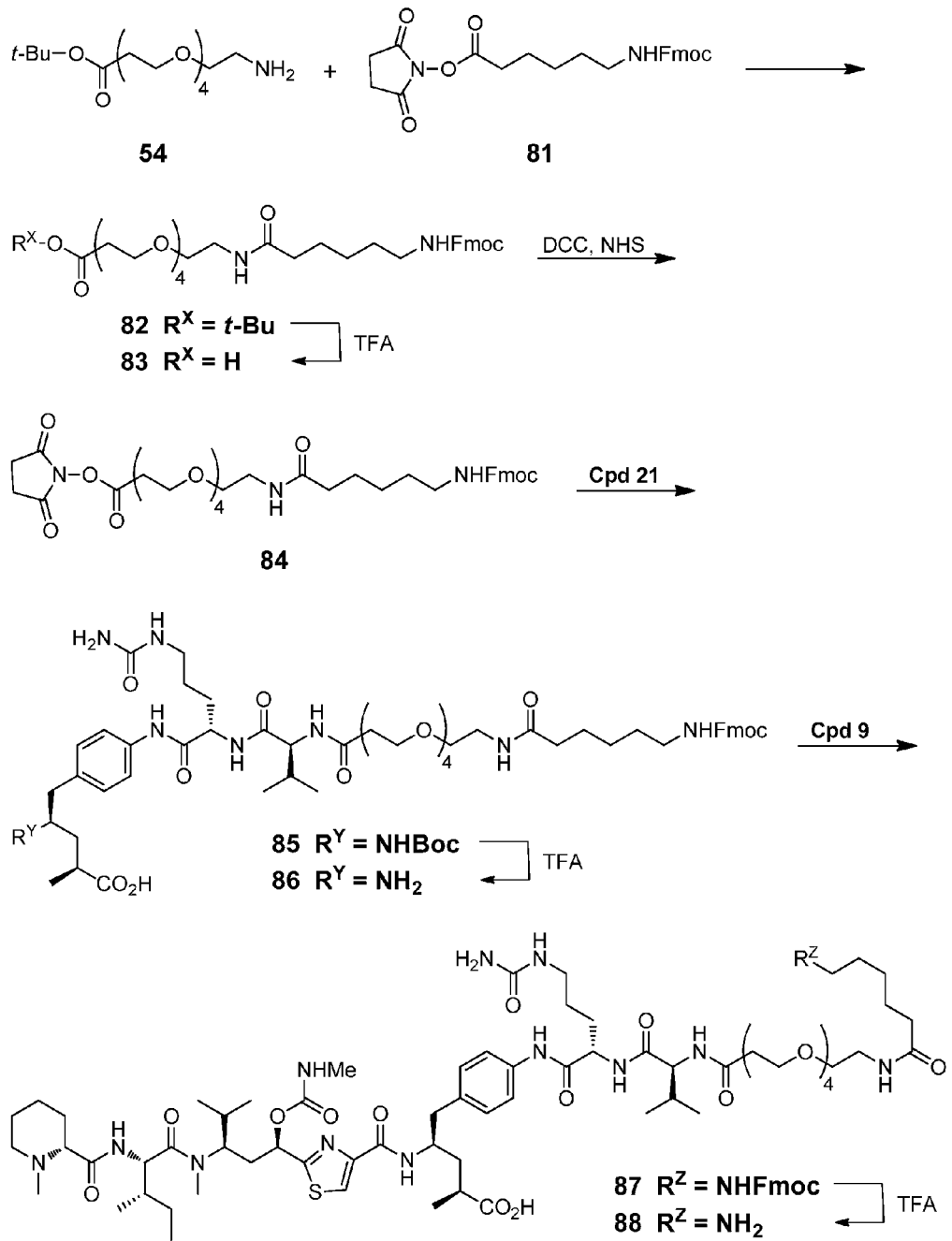

FIG. 24 shows a scheme for the synthesis of compounds of this invention suitable for conjugation via an aliphatic amine group.

DETAILED DESCRIPTION OF THE INVENTION

Definitions

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (C1q) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce inter-actions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_1$-$C_5$ aliphatic," or "$C_1$ to $C_5$ aliphatic," the latter two phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties).

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexyl-phenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzo-furanyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzo-furanyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of an aryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

Compositions

In formula (I), repeated below for convenience, (I)

the group $R^1$ preferably is Me, Et, n-Pr, i-Pr, or more preferably the latter.

Also in formula (I), the group $R^2$ preferably is $C_1$-$C_5$ alkyl, $C_1$-$C_5$ alkenyl, $C_1$-$C_5$ alkynyl, $CH_2OC(=O)C_1$-$C_5$ alkyl, $CH_2OC(=O)C_1$-$C_5$ alkenyl, $CH_2OC(=O)C_1$-$C_5$ alkynyl, —(CH$_2$)$_{1-2}$—[phenyl], or —(CH$_2$)$_{1-2}$—[phenyl]—NH$_2$.

Also in formula (I), preferred groups N(R$^{3a}$)(R$^{3b}$) are:

with it being especially preferred that one of R$^{3a}$ and R$^{3b}$ is H and the other is Me. In other preferred embodiments, R$^{3a}$ and R$^{3b}$ are both H or both Me, or one of R$^{3a}$ and R$^{3b}$ is H and the other is C$_6$H$_5$.

In another preferred embodiment, R$^{3a}$ and R$^{3b}$ are independently H, C$_1$-C$_5$ alkyl, CH$_2$(C$_5$-C$_6$ cycloalkyl), CH$_2$C$_6$H$_5$, or CH$_2$CH$_2$OH.

In the definitions of R$^1$ and R$^2$ in formula (I), where a group is defined as being either unsubstituted or substituted, it preferably is unsubstituted.

In the formulae of this specification, a bond traversing a phenyl ring between two carbons of the phenyl ring means that the group attached to the bond may be located at any of the ortho, meta, or para positions of the phenyl ring. By way of illustration, the formula represents , , or

.

The synthesis of counterparts of the tubulysin Tuv and Tup subunits with various R$^2$ and R$^4$ groups is taught by Cheng et al. 2011, the disclosure of which is incorporated herein by reference.

In a preferred embodiment of compounds according to formula (I), R$^1$ is

, $R_2$ is $C_1$-$C_5$ alkyl (especially Me or n-Pr) or

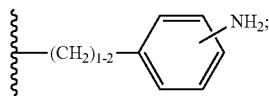

one of $R^{3a}$ and $R^{3b}$ is H and the other is Me; $R^4$ is

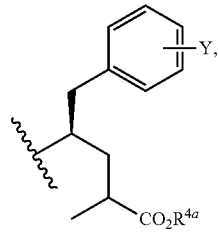

where Y is H or $NO_2$ and $R^{4a}$ is H, Me, or Et;
$R_5$ is Me; W is O, and n is 1.

In another preferred embodiment of compounds according to formula (I), n is 1 W is O, Y in $R^4$ is H or $NO_2$ (preferably H), and $R^2$ is

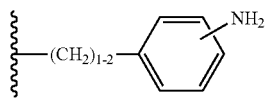

and more preferably

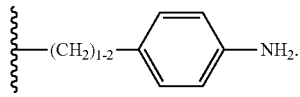

A compound according to this preferred embodiment is represented by formula (Ia)

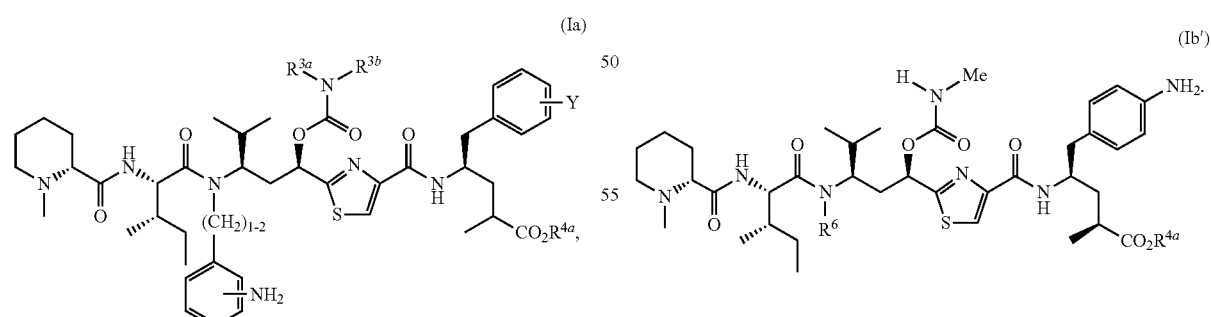

(Ia)

wherein Y is H or $NO_2$; $R^{4a}$ is H, Me, or Et; and $R^{3a}$ and $R^{3b}$ are independently H, $C_6H_5$, Me, or Et; or a pharmaceutically acceptable salt thereof.

Even more preferably, the compound has a structure represented by formula (Ia'):

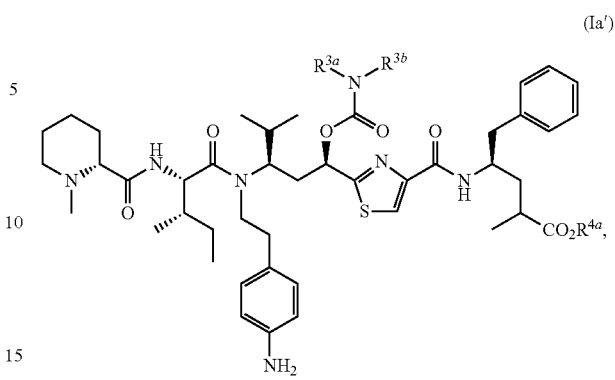

(Ia')

where $R^{4a}$ is H, Me, or Et; and $R^{3a}$ and $R^{3b}$ are independently H, $C_6H_5$, Me, or Et; or a pharmaceutically acceptable salt thereof.

In yet another preferred embodiment, W is O, Y is $NH_2$, n is 1, and both groups $R^{2a}$ in $R^2$ are other than $NH_2$. A compound according to this embodiment is represented by formula (Ib):

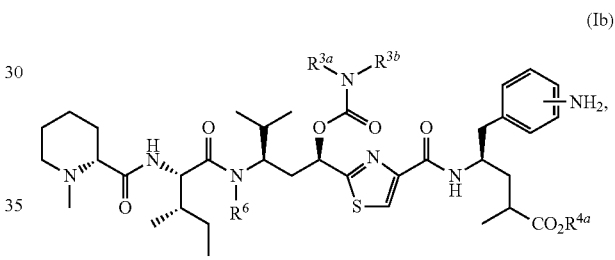

(Ib)

where $R^{4a}$ is H, Me, or Et; $R^{3a}$ and $R^{3b}$ are independently H, $C_6H_5$, Me, and Et; and $R^6$ is $C_1$-$C_5$ alkyl, $CH_2OC(=O)C_1$-$C_5$ alkyl, or $(CH_2)_{1-2}C_6H_5$; or a pharmaceutically acceptable salt thereof.

In yet another preferred embodiment, the compound has a structure represented by formula (Ib'):

(Ib')

where $R^{4a}$ is H, Me, or Et (preferably H) and $R^6$ is Me or n-Pr; or a pharmaceutically acceptable salt thereof.

Preferably, in formulae (Ia), (Ia'), and (Ib), one of $R^{3a}$ and $R^{3b}$ is H and the other is Me. In other preferred embodiments, $R^{3a}$ and $R^{3b}$ are both H or both Me, or one of $R^{3a}$ and $R^{3b}$ is H and the other is $C_6H_5$. In yet other preferred embodiments, $R^{3a}$ and $R^{3b}$ are independently H, Me, or Et Specific examples of compounds of this invention include the compounds shown immediately following, along with their pharmaceutically acceptable salts:
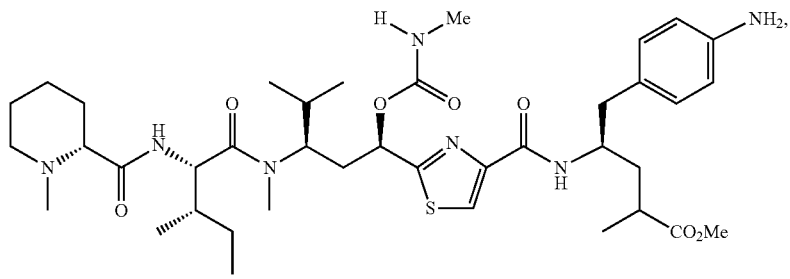
(I-1)
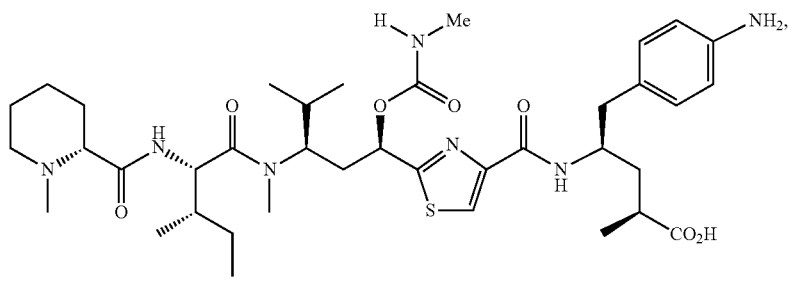
(I-2)
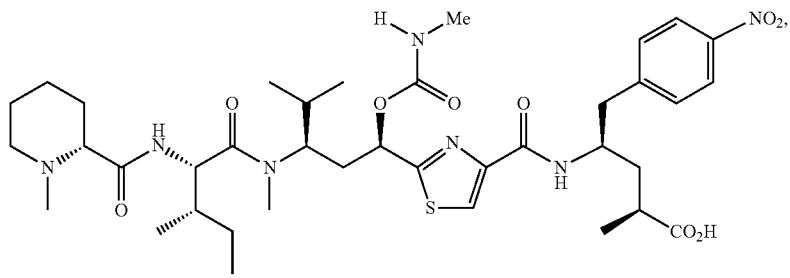
(I-3)
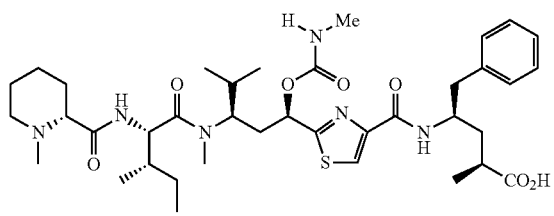
(I-4)
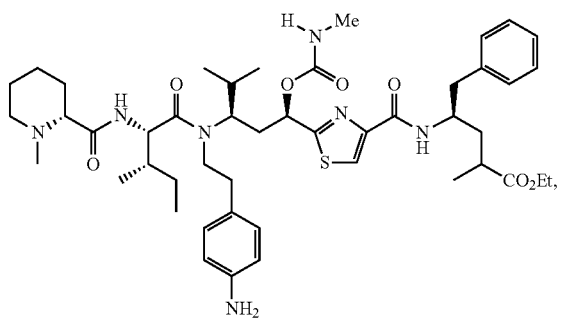
(I-5)
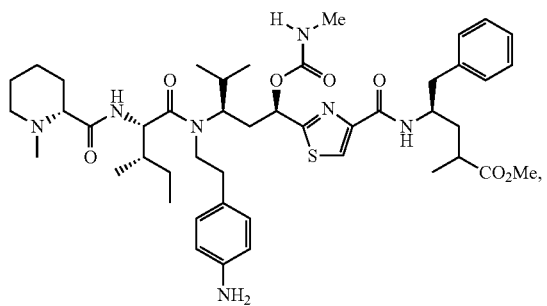
(I-6)
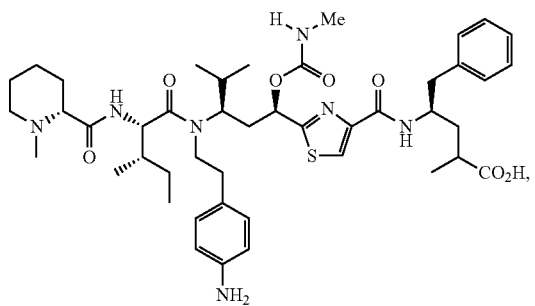
(I-7)

-continued

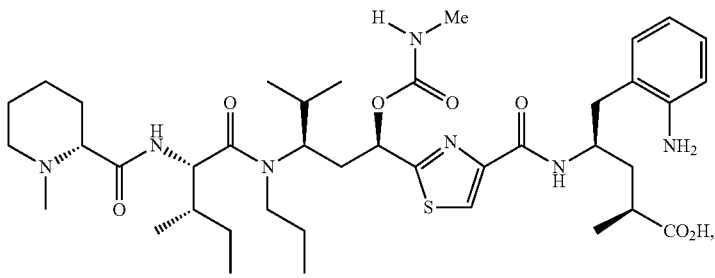
(I-8)

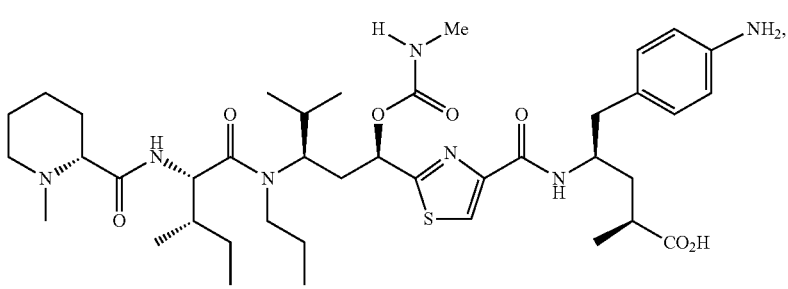
(I-9)

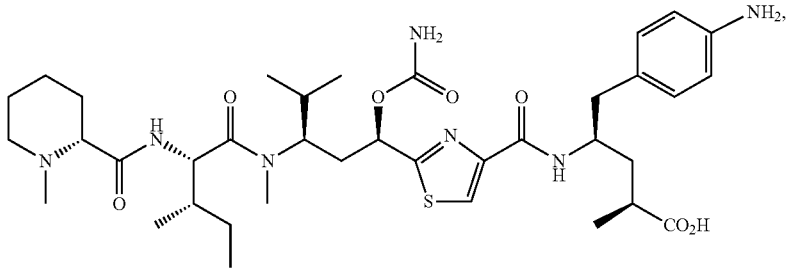
(I-10)

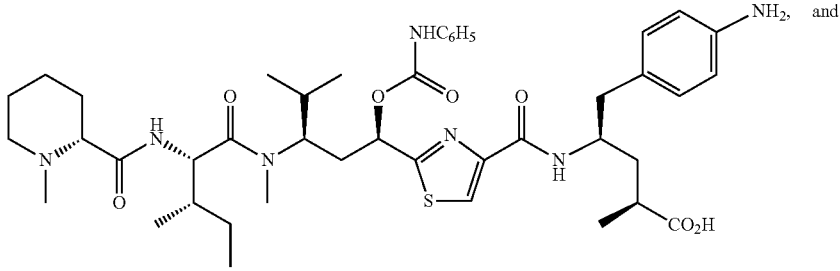
(I-11)

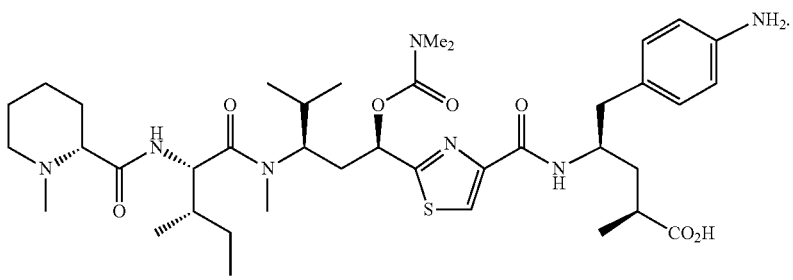
(I-12)

Compounds (I-2), (I-7), (I-8) and (I-9) are preferred.

Conjugates

Optionally, compounds of this invention may be conjugated to a targeting moiety that specifically or preferentially binds to a chemical entity on a cancer cell. Preferably, the targeting moiety is an antibody or antigen binding portion thereof and the chemical entity is a tumor associated antigen. Preferably, the conjugation is effected through a chemical bond to a functional group in the Tuv or Tup subunit, such as an amino group.

In another embodiment, there is provided a conjugate comprising cytotoxic compound according to this invention and a ligand, represented by formula (II)

$$[D(X^D)_aC(X_Z)_b]_mZ \qquad (II)$$

where Z is a ligand; D is a cytotoxic compound according to this invention (e.g., a compound according to formula (I), (Ia), (Ia'), or (Ib)); and —$(X^D)_a C(X^Z)_b$— are collectively referred to as a "linker moiety" or "linker" because they link Z and D. Within the linker, C is a cleavable group designed to be cleaved at or near the site of intended biological action of compound D; $X^D$ and $X^Z$ are referred to as spacer moieties (or "spacers") because they space apart D and C and C and Z, respectively; subscripts a and b are independently 0 or 1 (that is, the presence of $X^D$ and/or $X^Z$ are optional); and subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—serves a targeting function. By binding to a target tissue or cell where its antigen or receptor is located, ligand Z directs the conjugate there. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases compound D to exert its cytotoxic effect locally. In some instances, the conjugate is internalized into a target cell by endocytosis and cleavage takes place within the target cell. In this manner, precise delivery of compound D is achieved at the site of intended action, reducing the dosage needed. Also, compound D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one compound D, depending on the number of sites ligand Z has available for conjugation and the experimental conditions employed. Those skilled in the art will appreciate that, while each individual molecule of ligand Z is conjugated to an integer number of compounds D, a preparation of the conjugate may analyze for a non-integer ratio of compounds D to ligand Z, reflecting a statistical average. This ratio is referred to as the substitution ratio (SR) or, alternatively, in the case of antibody-drug conjugates, the drug-antibody ratio (DAR).

Ligand Z and Conjugation Thereof

Preferably, ligand Z is an antibody. For convenience and brevity and not of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Vlahov et al. 2008; Leamon et al. 2008). For the same reason, the detailed discussion below is primarily written in terms of a 1:1 ratio of antibody Z to compound D (m=1).

Preferably, ligand Z is an antibody against a tumor associated antigen, allowing a conjugate comprising such a ligand Z to selectively target cancer cells. Examples of such antigens include: mesothelin, prostate specific membrane antigen (PSMA), CD19, CD22, CD30, CD70, B7H4 (also known as O8E), protein tyrosine kinase 7 (PTK7), glypican-3, RG1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., US 2009/0074660 A1 (B7H4); Rao-Naik et al., U.S. Pat. No. 8,097,703 B2 (CD19); King et al., US 2010/0143368 A1 (CD22); Keler et al., U.S. Pat. No. 7,387,776 B2 (2008) (CD30); Terrett et al., U.S. Pat. No. 8,124,738 B2 (CD70); Korman et al., U.S. Pat. No. 6,984,720 B1 (2006) (CTLA-4); Korman et al., U.S. Pat. No. 8,008,449 B2 (2011) (PD-1); Huang et al., US 2009/0297438 A1 and Cardarelli et al., U.S. Pat. No. 7,875,278 B2 (PSMA); Terrett et al., US 2010/0034826 A1 (PTK7); Terrett et al., US 2010/0209432 (A1) (glypican-3); Harkins et al., U.S. Pat. No. 7,335,748 B2(2008) (RG1); Terrett et al., U.S. Pat. No. 8,268,970 B2 (2012) (mesothelin); and Xu et al., US 2010/0092484 A1 (CD44); the disclosures of which are incorporated herein by reference.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including ε-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple exposed lysine ε-amino groups, which can be conjugated via amide, urea, thiourea, or carbamate bonds using techniques known in the art, including modification with a heterobifunctional agent (as further described hereinbelow). However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., *Bioconjugate Chem.* 1994, 5, 504-507; Urnovitz et al., *U.S. Pat. No.* 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus. See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location away from the antigen binding site. The disclosures of the documents cited in this paragraph are all incorporated herein by reference.

In yet another embodiment, lysine e-amino groups can be modified with heterobifunctional reagents such as 2-iminothiolane or N-succinimidyl-3-(2-pyridyldithio)-propionate (SPDP), converting an e-amino group into a thiol or disulfide group—creating a cysteine surrogate, as it were. However, this method suffers from the same conjugation location and stoichiometry limitations associated with e-amino groups proper.

In yet another preferred embodiment, ligand Z is conjugated via the nucleophilic addition product of a thiol group to an acceptor moiety. A preferred acceptor moiety is a maleimide group, whose reaction with an antibody thiol group is generically illustrated below. The thiol group can be a native one, or one introduced as described above.

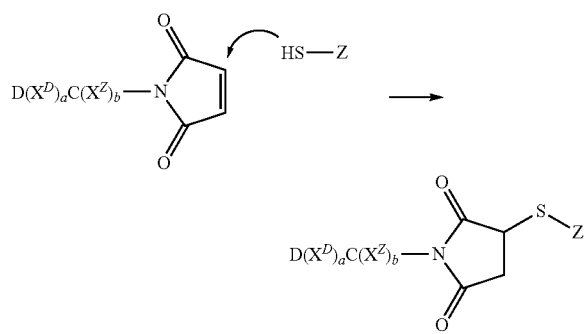

Ligand Z can also be conjugated via a functional group adapted for use with "click" chemistry, as discussed hereinbelow.

Linker —$(X^D)_a C(X^Z)_b$—

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by endocytosis by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci* (USA), 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred group C comprises a peptide bond that is cleaved, preferentially by a protease at the intended site of action, as opposed to by a protease in the serum. Typically, group C comprises from 1 to 20 amino acids, preferably from 1 to 6 amino acids, more preferably from 1 to 3 amino acids. The amino acid(s) can be natural and/or unnatural a-amino acids. Natural amino acids are those encoded by the genetic code, as well as amino acids derived therefrom, e.g., hydroxyproline, y-carboxyglutamate, citrulline, and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an a-amino acid but functions in a manner similar to one. The term "unnatural amino acid" is intended to represent the "D" stereochemical form, the natural amino acids being of the "L" form.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) For additional information regarding cathepsin-cleavable groups, see Dubowchik et al., *Biorg. Med. Chem. Lett.* 8, 3341-3346 (1998); Dubowchik et al., *Bioorg. Med. Chem. Lett.,* 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising the two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to five amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., US 2010/0113476 A1, the disclosure of which is incorporated herein by reference.

Group C can also be a photocleavable one, for example a nitrobenzyl ether that is cleaved upon exposure to light.

Group C can be bonded directly to antibody Z or compound D; that is, spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine e-amino group of antibody Z. In a preferred embodiment, compound D is directly bonded to group C via a peptidyl bond to a carboxyl or amine group in compound D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

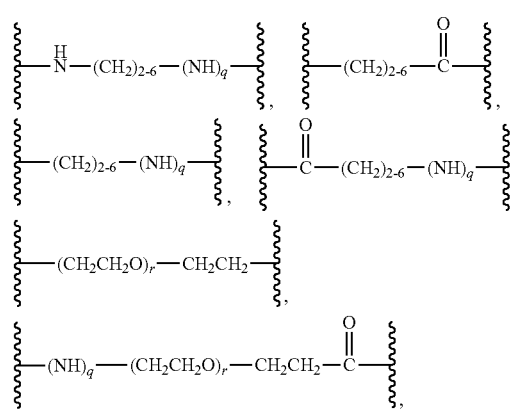

and combinations thereof, where the subscript q is 0 or 1 and the subscript r is 1 to 24, preferably 2 to 4. These segments can be combined, such as shown below:

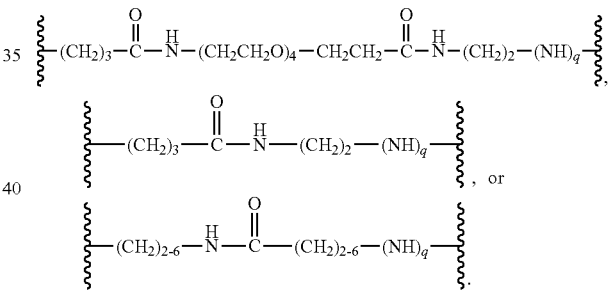

Spacer $X^D$, if present, provides spatial separation between group C and compound D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 4 to 25 atoms, more preferably from 4 to 20 atoms, between Z and C or D and C, respectively.

Either spacer $X^Z$ or $X^D$, or both, can comprise a self-immolating moiety. A self-immolating moiety is a moiety that (1) is bonded to group C and either antibody Z or cytotoxin D and (2) has a structure such that cleavage from group C initiates a reaction sequence resulting in the self-immolating moiety disbonding itself from antibody Z or cytotoxin D, as the case may be. In other words, reaction at a site distal from antibody Z or cytotoxin D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to cytotoxin D, the biological activity of the latter may be impaired. The use of a self-immolating moiety is especially desirable where cleavable group C is a polypeptide.

Exemplary self-immolating moieties (i)-(v) bonded to a hydroxyl or amino group on a partner molecule D are shown below:

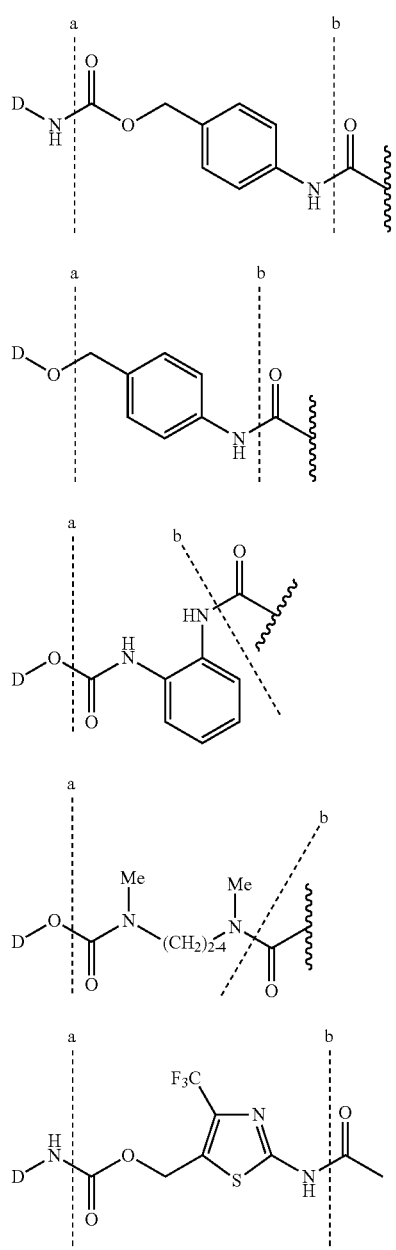

The self-immolating moiety is the structure between dotted lines a and b, with adjacent structural features shown to provide context. Self-immolating moieties (i) and (v) are bonded to a compound D-NH$_2$ (i.e., compound D is conjugated via an amino group), while self-immolating moieties (ii), (iii), and (iv) are bonded to a compound D-OH (i.e., compound D is conjugated via a hydroxyl or carboxyl group). Cleavage of the amide bond at dotted line b releases the amide nitrogen as an amine nitrogen, initiating a reaction sequence that results in the cleavage of the bond at dotted line a and the consequent release of D-OH or D-NH$_2$, as the case may be. For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; and Senter et al., US 2003/0096743 A1; the disclosures of which are incorporated by reference.

In another embodiment, an antibody targeting moiety and the cytotoxic compound D are linked by a non-cleavable linker. Degradation of the antibody eventually reduces the linker to a small appended moiety that does not interfere with the biological activity of cytotoxic compound D.

Compound D—Linker Compositions

Conjugates of this invention preferably are prepared by first joining a compound D and linker $(X^D)_aC(X^Z)_b$ (where $X^D$, C, $X^Z$, a, and b are as defined for formula (II)) to form a drug-linker composition represented by formula (III):

$$D-(X^D)_aC(X^Z)_b-R^{31} \quad (III)$$

where $R^{31}$ is a functional group suitable for reacting with a functional group on antibody Z to form the conjugate. Examples of suitable groups $R^{31}$ include amino, azide, cyclooctyne,

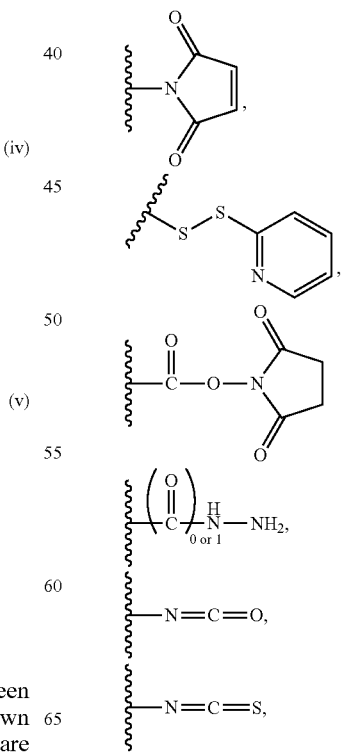

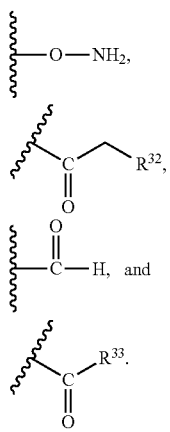

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D\text{-}(X^D)_a C(X^Z)_b\text{—}R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are selected from the group consisting of:

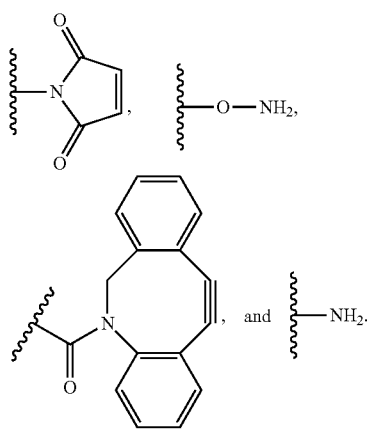

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

An —SH group is particularly useful for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

Azide and cyclooctyne are complementary functional groups that can effect conjugation via so-called copper-free "click chemistry," in which the azide adds across the strained alkyne bond of the cyclooctyne to form an 1,2,3-triazole ring. See, e.g., Agard et al., J. Amer. Chem. Soc. 2004, 126, 15046-15047; Best, Biochemistry 2009, 48, 6571-6584. The azide can be the reactive functional group $R^{31}$ in formula (III) and the cyclooctyne can be situated on the antibody or antigen binding portion thereof, or vice-versa. A cyclooctyne group can be provided by a DIBO reagent (available from Invitrogen/Molecular Probes, Eugene, Oreg.).

Techniques for introducing non-natural amino acids into antibodies can be utilized, with the non-natural amino acid providing a functionality for conjugation with the reactive functional group. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site by the formation of an oxime with a hydroxylamino reactive functional group. Alternatively, the non-natural amino acid p-azidophenylalanine can be incorporated into an antibody to provide an azide functional group for conjugation via click chemistry. Non-natural amino acids can also be incorporated into an antibody or other polypeptide using cell-free methods, as taught in Goerke et al., US 2010/0093024 A1 (2010) and Goerke et al., Biotechnol. Bioeng. 2009, 102 (2), 400-416.

An amine ($NH_2$) group can be used for conjugation using the enzyme transglutaminase, as taught in Jeger et al., Angew. Chem. Int. Ed. 2010, 49, 9995-9997.

Conjugation can also be effected using the enzyme Sortase A, as taught in Levary et al., PLoS One 2011, 6(4), e18342; Proft, Biotechnol. Lett. 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

The group D in the formulae $[D(X^D)_a C(X^Z)_b]_m Z$ and $D\text{-}(X^D)_a C(X^Z)_b\text{—}R^{31}$ preferably has a structure according to formula (D-a)

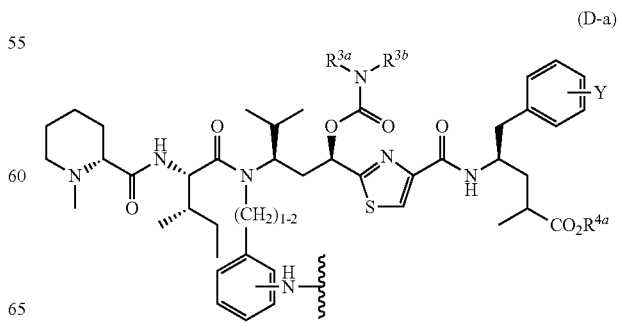

(D-a)

or formula (D-b)
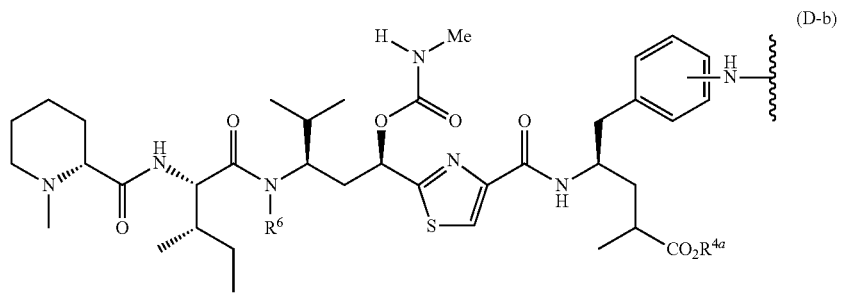
(D-b)
wherein Y is H or NO$_2$; R$^{4a}$ is H, Me, or Et; R$^{3a}$ and R$^{3b}$ are independently H, Me, or Et; and R$^6$ is C$_1$-C$_5$ alkyl, CH$_2$OC(=O)C$_1$-C$_5$ alkyl, or (CH$_2$)$_{1\text{-}2}$C$_6$H$_5$.
Examples of such groups D include:
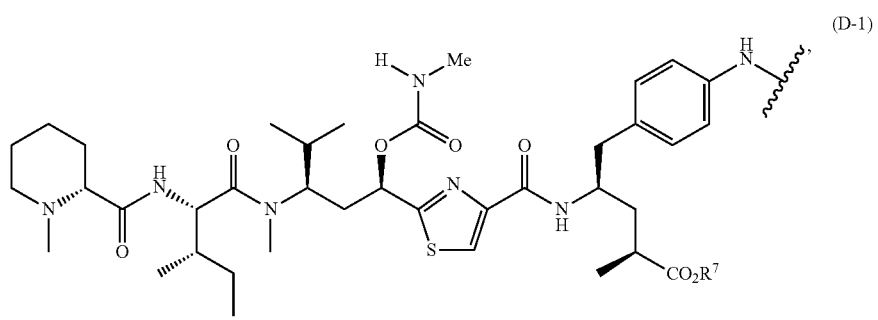
(D-1)
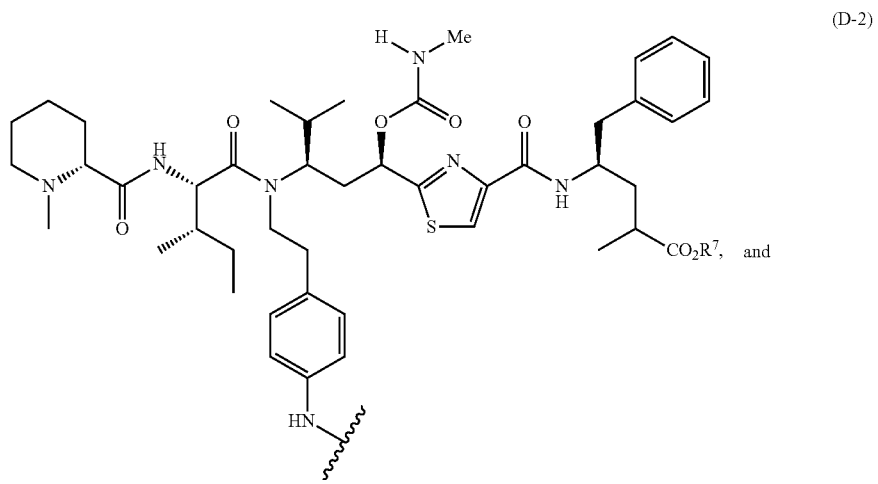
(D-2)
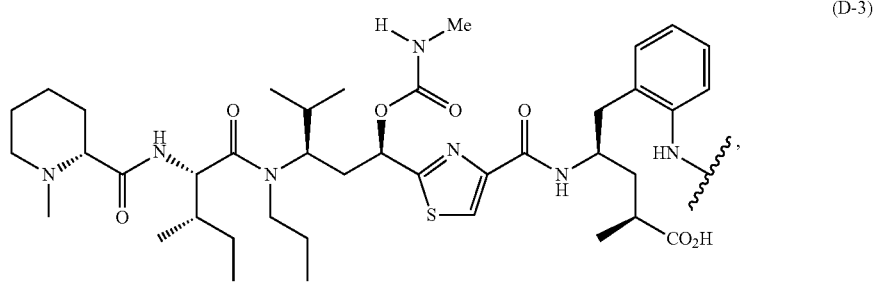
(D-3)
wherein R$^7$ is H, Me, or Et.

Examples of compositions according to formula D-($X^D$)$_a$C ($X^Z$)$_b$—$R^{31}$ include the ones shown immediately following; along with their pharmaceutically acceptable salts:
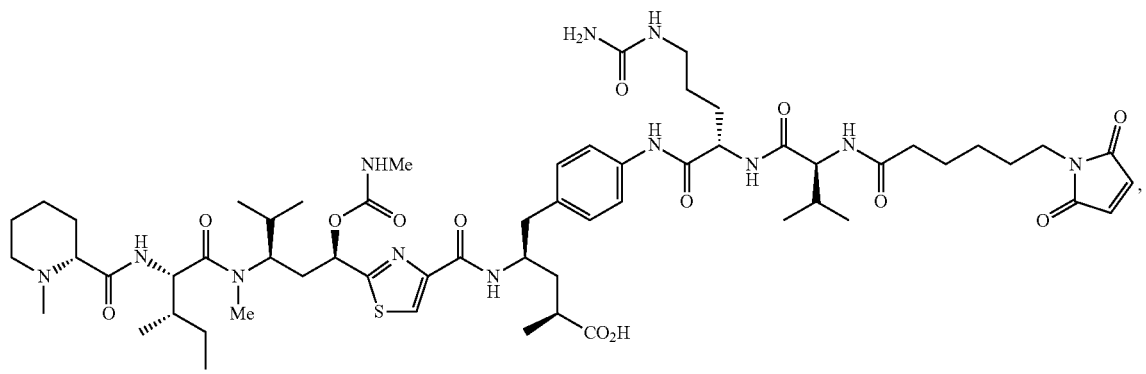
(III-1)
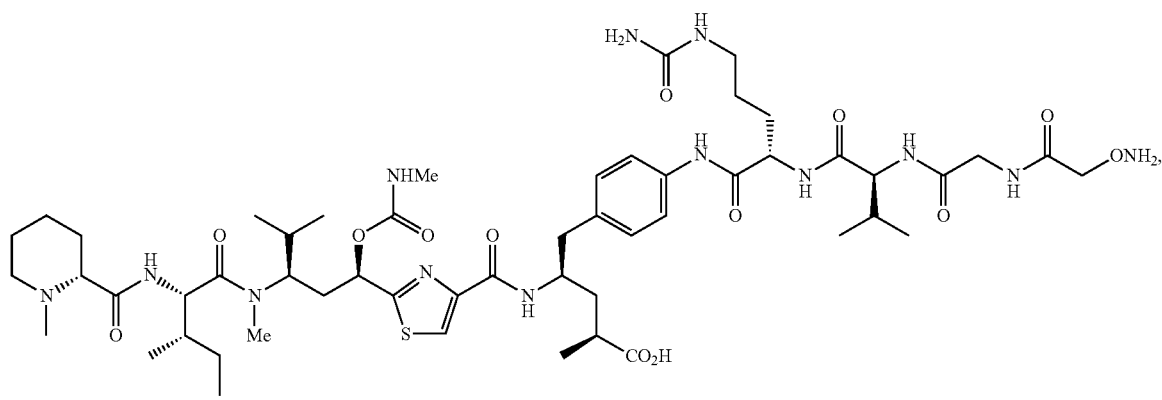
(III-2)
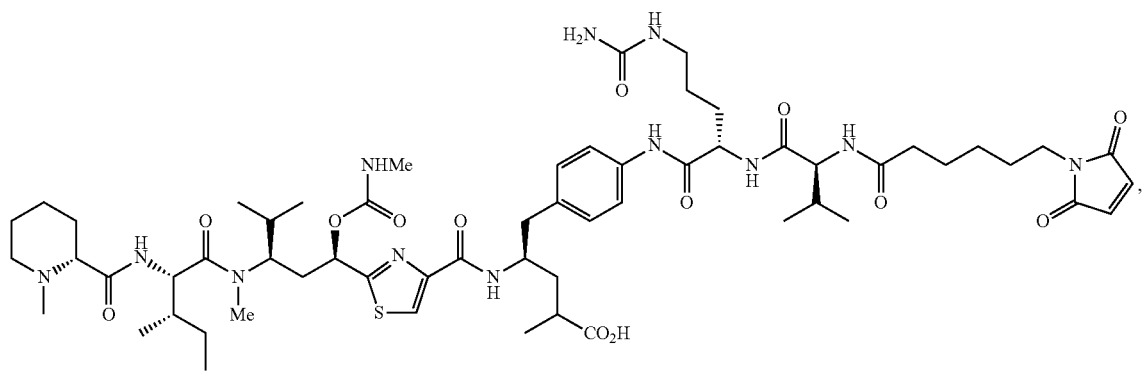
(III-3)

-continued
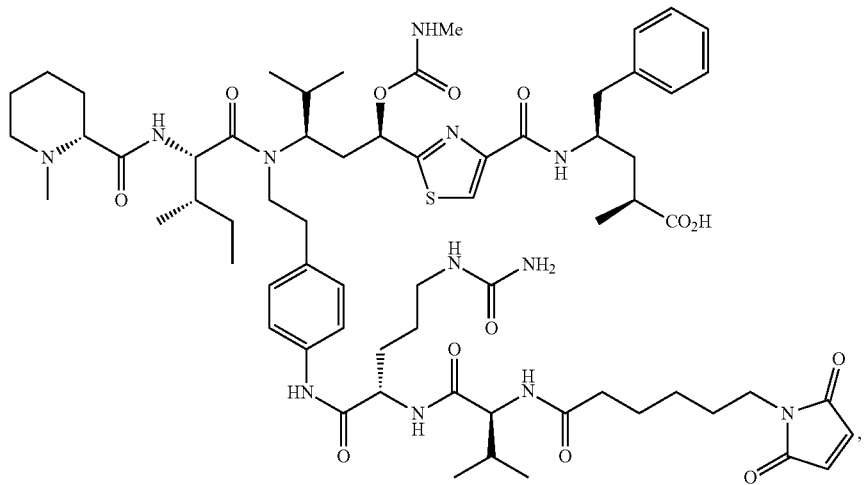
(III-4)
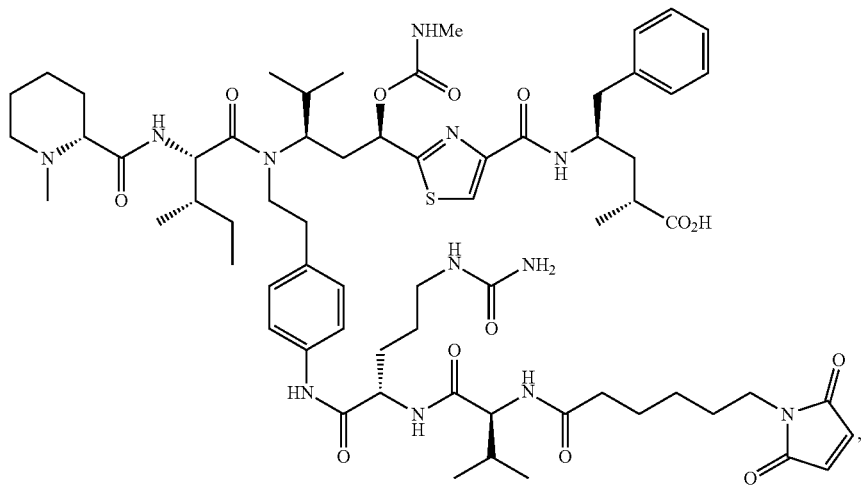
(III-5)
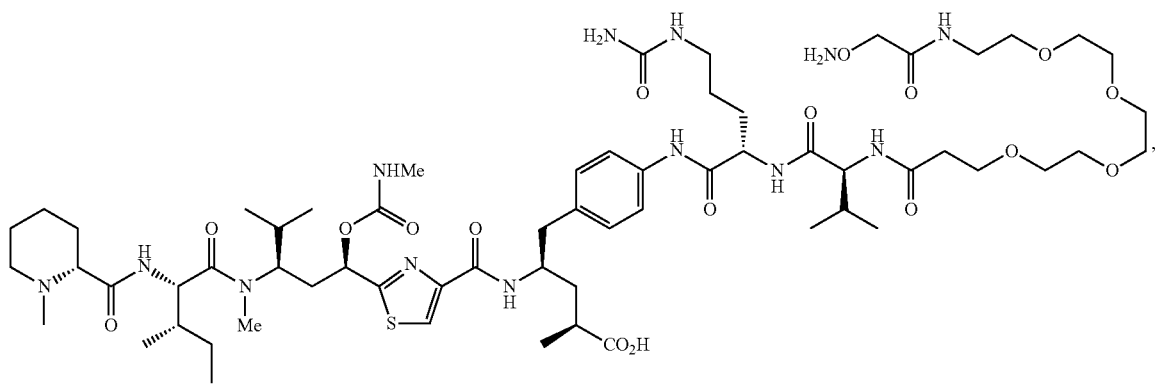
(III-6)

-continued
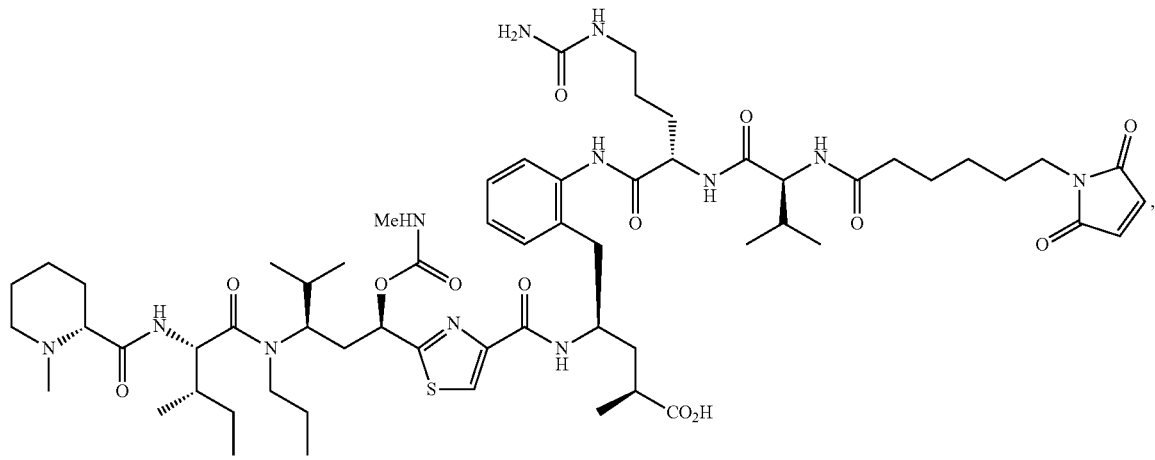
(III-7)
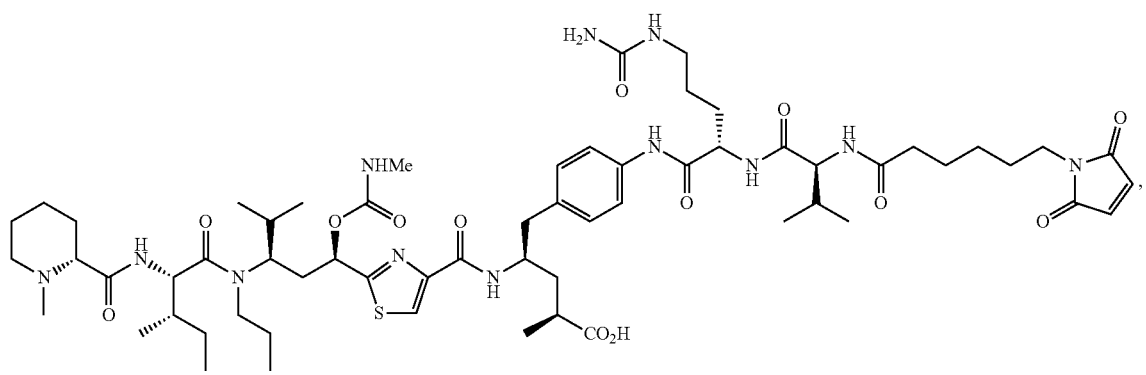
(III-8)
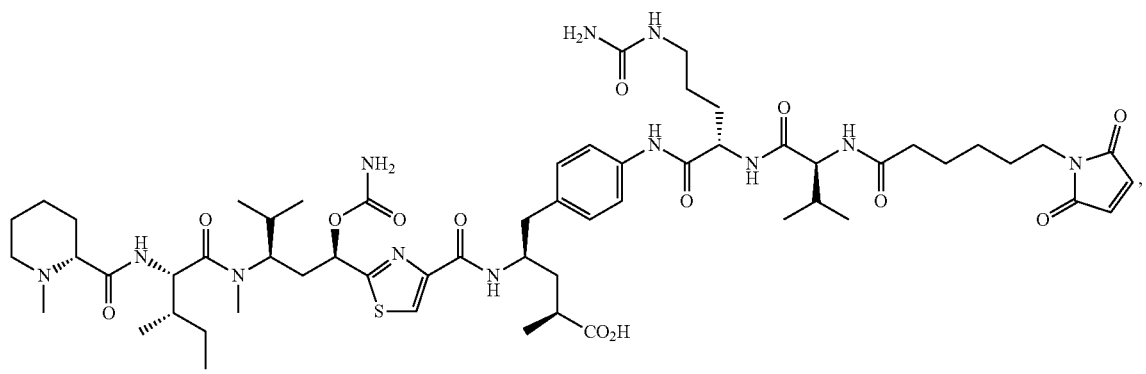
(III-9)
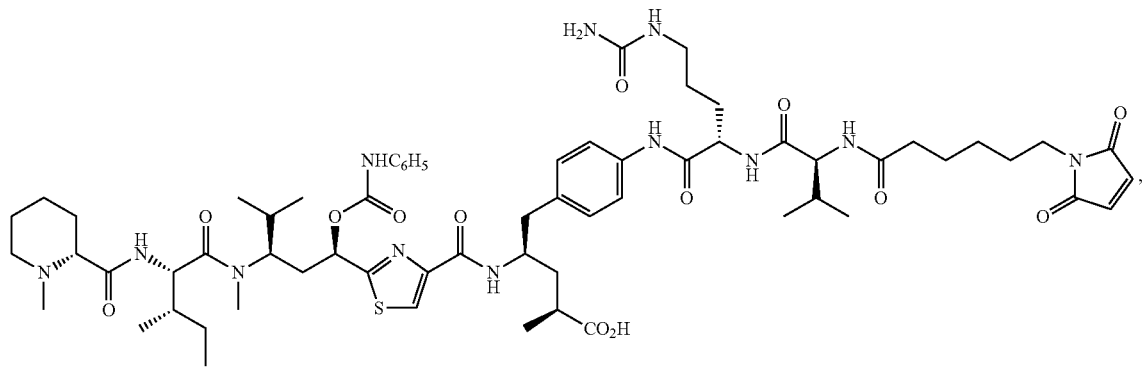
(III-10)

-continued
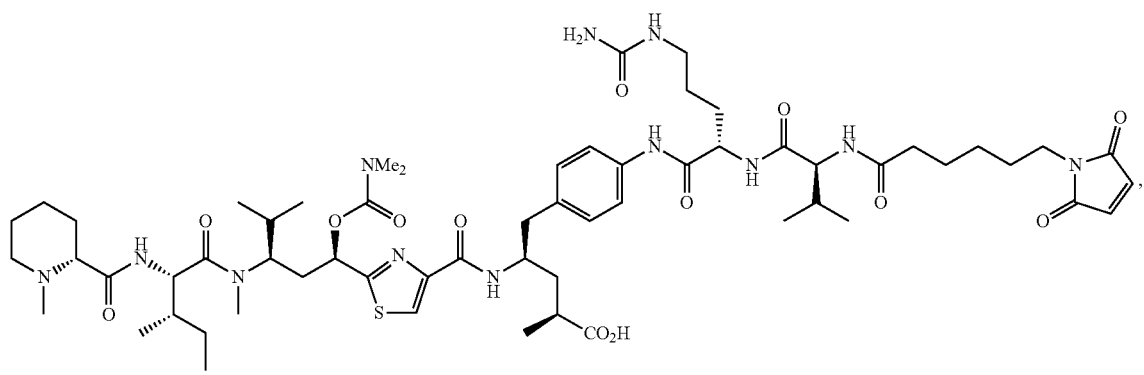
(III-11)
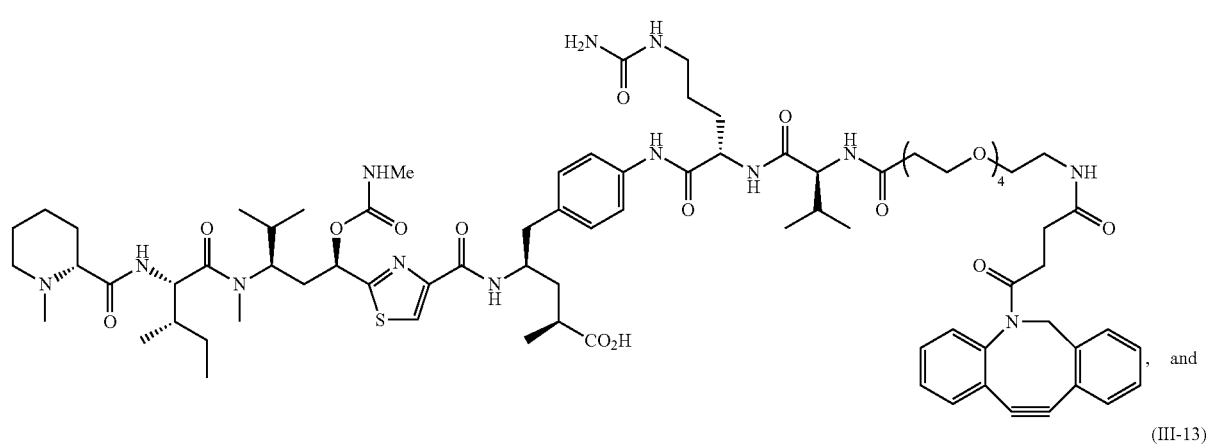
(III-12)
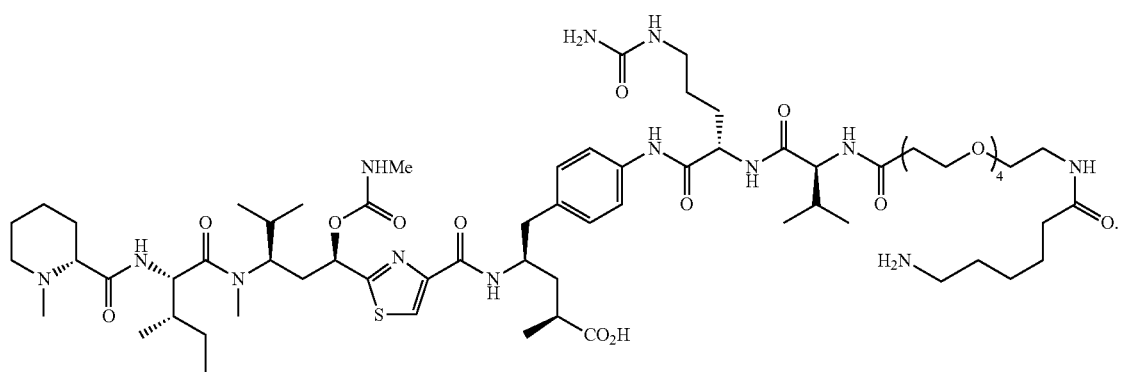
(III-13)
A preferred drug-linker compound has a structure represented by formula (III-a):
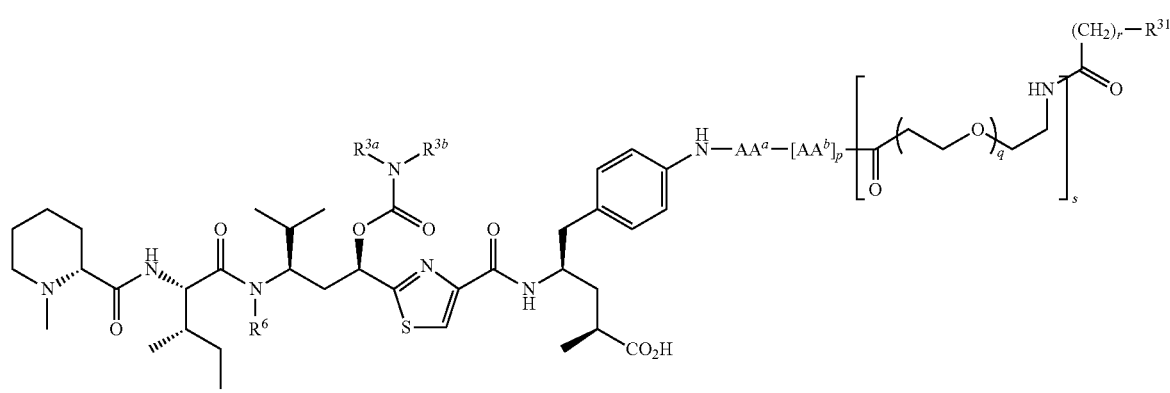
(III-a)

where
- $R^{3a}$ and $R^{3b}$ are independently H, Me, or Et;
- $R^6$ is Me, Et, or n-Pr;
- $AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
- p is 1, 2, 3, or 4;
- q is 1, 2, 3, 4, 5, 6, 7, 8, 9, or 10 (preferably 2, 3, or 4);
- r is 1, 2, 3, 4, or 5;
- s is 0 or 1; and
- $R^{31}$ is selected from the group consisting of

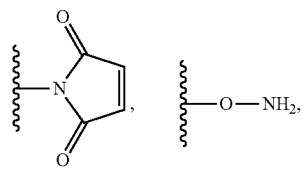

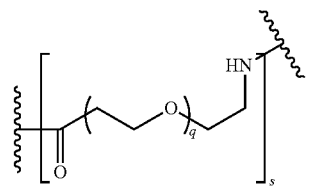

if s is 1 and with

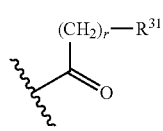

if s is 0.

A more preferred drug-linker compound has a structure represented by formula (III-b):

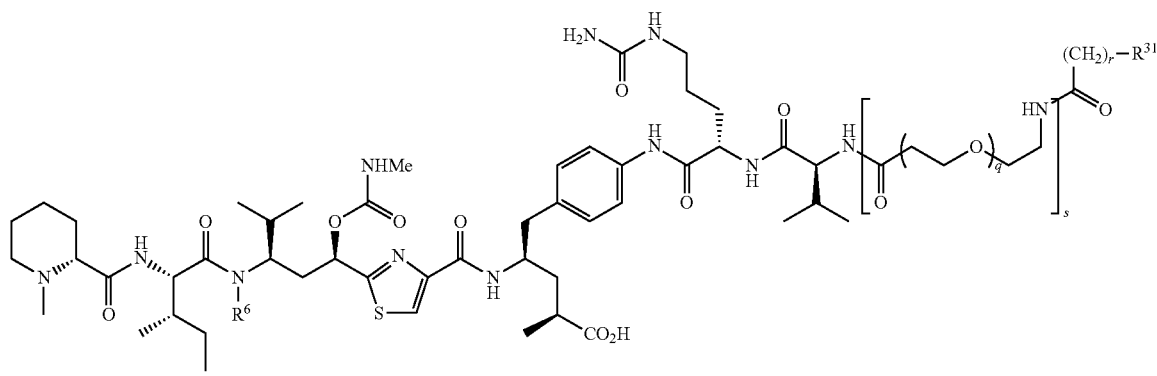

(III-b)

-continued

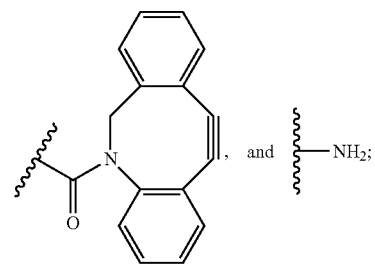

or a pharmaceutically acceptable salt thereof.

In formula (III-a), $-AA^a-[AA^b]_p-$ represents a polypeptide whose length is determined by the value of p (e.g., dipeptide if p is 1, tetrapeptide if p is 3, etc.). $AA^a$ is at the carboxy terminus of the polypeptide and its carboxyl group forms a peptide (amide) bond with the anilino nitrogen of the drug. Conversely, the last $AA^b$ is at the amino terminus of the polypeptide and its alpha-amino group forms a peptide bond with where
- $R^6$ is Me or n-Pr;
- q is 1, 2, 3, 4, 5, 6, 7, 8, 9, or 10 (preferably 2, 3, or 4);
- r is 1, 2, 3, 4, or 5;
- s is 0 or 1; and $R^{31}$ is selected from the group consisting of

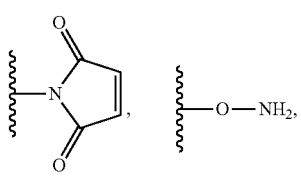

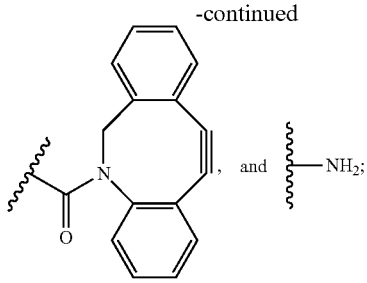

or a pharmaceutically acceptable salt thereof.

Preparation of Conjugates

The following is an illustrative procedure, based on introduction of free thiol groups into an antibody by reaction of lysine ε-amino groups with 2-iminothiolane, followed by reaction with a maleimide-containing drug-linker moiety such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM pH 6.0 HEPES buffer using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety is added at a 3-fold molar excess per thiol. The conjugation reaction is allowed to proceed in conjugation buffer also containing a final concentration of 5% dimethylsulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at RT for 2 h with stirring. Following incubation, the conjugation reaction mixture is centrifuged and filtered through a 0.2 Lm filter. Purification of the conjugate can be achieved through chromatography using a number of methods. In one method, the conjugate is purified using size-exclusion chromatography on a SEPHACRYL™ S200 column pre-equilibrated with 50 mM pH 7.2 HEPES buffer containing 5 mM glycine and 150 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should to be optimized in each case. For example, antibody-drug conjugate reaction mix is applied to an SP-SEPHAROSE™ column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the conjugate are pooled and dialyzed against formulation buffer (50 mM pH 7.2 HEPES buffer containing 5 mM glycine and 100 mM NaCl).

Those skilled in the art will understand that the above-described conditions and methodology are exemplary and non-limiting and that other approaches for conjugation are known in the art and usable in the present invention.

A conjugate prepared by the procedure described above is represented by formula (II-1). It is a conjugate of compound (III-1) and the anti-mesothelin antibody 6A4 (Terrett et al. 2012):

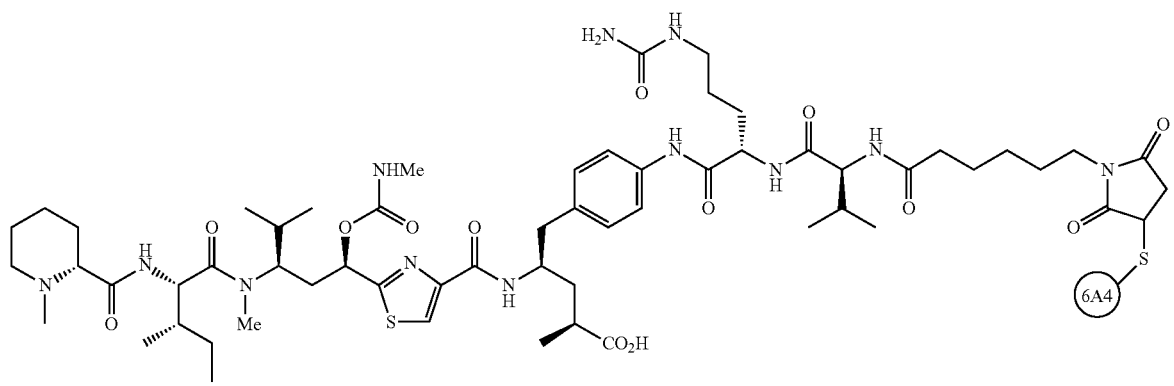

(II-1)

Those skilled in the art will appreciate that such a conjugate preparation may have moieties with different substitution ratios, typically ranging from 1 to 5, and that such preparation can be represented by formula (II-1'):

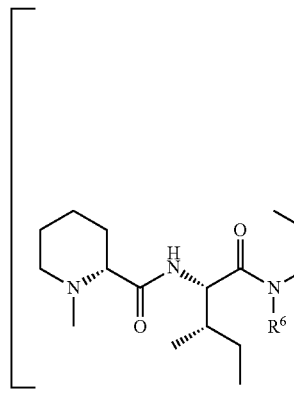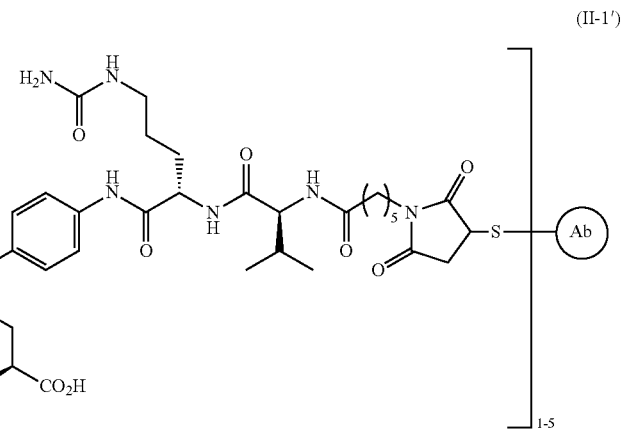

(II-1')

where $R^6$ is Me or n-Pr and Ab is an antibody. The antibody preferably is an anti-CD70, anti-mesothelin, or anti-glypican-3 antibody.

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994) *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomyosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be renal, lung, gastric, or ovarian cancer.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation.

Example 1

Compound (III-1)

This example describes the synthesis of compound (III-1), the corresponding scheme being shown in combined FIGS. 1, 2a-2b, and 3.

Compound 2.

A mixture of compound 1 (6 g, 16.6 mmol; prepared according to Peltier et al. 2006) and paraformaldehyde (9.94 g, 331 mmol) in toluene (150 mL) was heated in a sealed vessel at 70° C. for 24 h. Thin layer chromatography (TLC) showed that the reaction was complete. The reaction mixture was filtered through CELITE™ filter media and the filter cake was washed thoroughly with toluene. After evaporation of the solvent, the crude product was purified by flash chromatography eluting from silica gel with a gradient of 0-70% ethyl acetate (EtOAc) in dichloromethane (DCM) to afford 4.76 g of compound 2 as a light yellow oil. MS: (+) m/z 375.2 (M+1).

Compound 3.

Hydrochloric acid (4.0 M in 1,4-dioxane, 12.24 mL, 50.8 mmol) was added drop-wise to a solution of compound 2 (4.76 g, 12.7 mmol) in acetonitrile (62 mL) and methanol (6.8 mL), in the presence of support-bound cyanoborohydride (MP-BH$_3$CN) resin (4.85 g, 12.7 mmol). The reaction mixture was stirred at room temperature (RT) for 3 h. LCMS showed the reaction went to completion. The resin was filtered off and washed with acetonitrile-methanol mixture. After evaporation of the solvent, the crude product was purified by flash chromatography eluting from silica gel with a gradient of 0-10% methanol in DCM containing 1% NH$_4$OH to afford crude compound 3.

The product fractions were concentrated, diluted with EtOAc, and washed once with saturated aq. NaHCO$_3$ to remove excess ammonium salts. The aqueous fraction was back-extracted once with EtOAc. The combined organic phases were dried and concentrated to afford 2.82 g of compound 3 as a foamy solid. MS: (+) m/z 273.2 (M+1).

Compound 4.

Polymer-bound N-benzyl-N-cyclohexylcarbodiimide (Aldrich, 4.5 g, 5.21 mmol) was added to a solution of compound 3 (1.42 g, 5.21 mmol), t-butanol (0.72 g, 5.32 mmol) and Boc-protected isoleucine 3a (1.27 g, 5.47 mmol) in DCM (48 mL) at 0° C. The reaction mixture was stirred at RT overnight. The resin was filtered off and washed with DCM. The filtrate was concentrated, diluted with EtOAc, and washed once with saturated aq. NaHCO$_3$. The aqueous solution was extracted twice with EtOAc. The combined organic layers were dried, filtered and concentrated. The crude product was purified by flash chromatography eluting from silica gel with a gradient of 0-10% methanol in DCM containing 1% NH$_4$OH to afford fractons containing intermediate product 3b.

The product-containing fractions were combined, concentrated, diluted with EtOAc, and washed with saturated aq. NaHCO$_3$ to remove excess ammonium salts. The aqueous fraction was back-extracted once with EtOAc. The combined organic phases were dried and concentrated to afford intermediate product 3b as a white solid.

Intermediate product 3b in toluene (50 mL) was heated to 90° C. in a sealed vessel overnight, with stirring. LCMS showed the reaction went to completion. The solvent was evaporated. The crude product was purified by flash chromatography eluting from silica gel with a gradient of 0-100% EtOAc in hexanes to afford 1.3 g of compound 4 as a light yellow solid. MS: (+) m/z 486.3 (M+1).

Compound 5.

Trifluoroacetic acid (TFA, 26 mL) was added to a mixture of compound 4 in DCM (26 mL). After stirring at RT for 30 min, LCMS showed the reaction was complete. The solution was concentrated, diluted with EtOAC, and washed once with saturated aq. NaHCO$_3$. The aqueous solution was back-extracted twice with EtOAc. The combined organic layers were dried, filtered, and concentrated to afford 1.03 g of compound 5 as white solid. MS: (+) m/z 386.3 (M+1).

Compound 6.

DCC (0.664 g, 3.22 mmol) was added to a mixture of compound 5 (1.03 g, 2.68 mmol), (R)-1-methylpiperidine-2-carboxylic acid 5a (0.4 g, 2.81 mmol; prepared according to Peltier et al. 2006), and t-butanol (0.369 g, 2.73 mmol) in DCM at 0° C. The reaction mixture was allowed to warm to RT and stirred at RT overnight. The solid was filtered off, and the filtrate was concentrated. The residue was dissolved in EtOAc and washed once with saturated aq. NaHCO$_3$. The aqueous solution was back-extracted twice with EtOAc. The combined organic layers were dried, filtered, and concentrated. The crude product was purified by flash chromatography eluting from silica gel with a gradient of 0-20% methanol in DCM to afford 1.23 g of compound 6 as a light yellow solid. MS: (+) m/z 511.4 (M+1).

Compound 7.

A mixture of N,N-diisopropylethylamine (DIEA, also referred to as DIPEA, 0.972 mL, 5.58 mmol), bis(4-nitrophenyl) carbonate (BNPC, 1.698 g, 5.58 mmol) and compound 6 (0.57 g, 1.116 mmol) in N,N-dimethylformamide (DMF, 10 mL) was stirred at RT overnight. LCMS showed the reaction went to completion. The solvent was evaporated. The crude product was purified by silica gel flash chromatography with a gradient of 0-20% methanol in DCM to afford 0.68 g of compound 7 as a yellow oil. MS: (+) m/z 676.4 (M+1).

Compound 8.

Methylamine in methanol (2.0 M, 0.089 mL, 0.178 mmol) was added to compound 7 (0.1 g, 0.148 mmol) in methanol (1 mL). After the reaction mixture was stirred at RT for 10 min, LCMS showed the reaction was complete. The solvent was evaporated to afford 0.084 g of compound 8. MS: (+) m/z 568.4 (M+1).

Compound 9.

Lithium hydroxide (7.09 mg, 0.296 mmol) in water (0.5 mL) was added to a solution of compound 8 (0.084 g, 0.148 mmol) in 1,4-dioxane (0.5 mL) at RT. After the reaction mixture was stirred at RT for 2 h, LCMS showed the reaction was complete. The solvent was evaporated. The crude product was purified by flash chromatography eluting from silica gel with a gradient of 0-30% methanol in DCM to afford 0.075 g of compound 9 as a white solid. MS: (+) m/z 554.4 (M+1).

Compound 10.

Triethylamine (11.73 mL, 84 mmol) was added to a mixture of di-t-butyldicarbonate (BOC$_2$O, 10.57 mL, 46.0 mmol) and (S)-methyl 2-amino-3-(4-nitrophenyl)propanoate hydrochloride 9a (10 g, 38.4 mmol) in acetonitrile (300 mL) at 0° C. The reaction mixture was allowed to warm to RT, and stirred at RT overnight. LCMS showed the reaction went to completion. The reaction mixture was concentrated, and the product was re-dissolved in 200 mL of diethyl ether. The solid was filtered off, and the filtrate was concentrated. The crude product was purified by flash chromatography eluting from silica gel with a gradient of 0-50% EtOAc in hexanes to afford 11.3 g of a Boc protected intermediate as a white solid.

Pd/C catalyst (10 wt. %, 0.85 g, 7.99 mmol) was added to a solution of the Boc protected intermediate (15 g, 46.2 mmol) in MeOH (200 mL). The reaction mixture was stirred under a hydrogen atmosphere overnight. The Pd/C catalyst was filtered, and the filtrate was concentrated to afford 13.6 g of compound 10 as a white solid. MS: (+) m/z 195.2 (M+1-Boc).

Compound 11.

Pyridine (5.77 mL, 71.3 mmol) was added to a solution of benzyl chloroformate (10.18 mL, 71.3 mmol) and compound 10 (17.5 g, 59.5 mmol) in DCM (185 mL) at 0° C. The reaction mixture was allowed to warm to RT and was stirred at RT overnight. The reaction was quenched by addition of saturated aq. NaHCO$_3$, and washed with brine. The organic layer was dried, filtered, and concentrated. The crude product was purified by flash chromatography eluting from silica gel with a gradient of 0-50% EtOAc in hexanes to afford 22.6 g of compound 11 as a colorless oil. MS: (+) m/z 329.2 (M+1-Boc).

Compound 12.

Diisobutylaluminum hydride (DIBAL-H) in hexanes (1M, 26.5 mL, 26.5 mmol) was added to a solution of compound 11 (5.17 g, 12.07 mmol) in DCM (39 mL) at −78° C. The reaction mixture was stirred at −78° C. for 2 h. Acetic acid (24 mL) and toluene (36 mL) were added at −78° C. The reaction mixture was warmed to RT. Tartaric acid (10% aq., 69 mL) was added to the reaction mixture. The aqueous solution was extracted with hexanes and EtOAc (v/v 1:1) mixture. The combined organic layers were dried, filtered, and concentrated. The crude product was purified by flash chromatography eluting from silica gel with a gradient of 0-50% EtOAc in hexanes to afford 3.12 g of compound 12 as a white solid. MS: (+) m/z 299.2 (M+1-Boc).

Compound 13.

Dibutyl(((trifluoromethyl)sulfonyl)oxy)borane (Bu2BOTf, 1M in DCM, 8.61 mL, 8.61 mmol) and DIEA (1.637 mL, 9.40 mmol) were added to a solution of (S)-4-isopropyl-3-propionyloxazolidin-2-one 12a (1.450 g, 7.83 mmol) in DCM (7.8 mL) at 0° C. The reaction mixture was stirred at 0° C. for 45 min. A solution of compound 12 (3.12 g, 7.83 mmol) in DCM (7.8 mL) was added to the reaction mixture at −78° C. The reaction mixture was allowed to warm up to RT overnight. Sodium phosphate buffer (pH 7, 29 mL) was added. The aqueous solution was extracted with DCM. The combined organic layers were washed with brine, dried, filtered, and concentrated.

The residue was re-dissolved in methanol (130 mL) and cooled to 0° C. Aqueous $H_2O_2$ (30%, 39.7 mL) was added to the reaction mixture at 0° C. The reaction mixture was stirred at 0° C. for 4 h. Water (39 mL) was added. Some of the solvent (MeOH) was evaporated. The aqueous solution was extracted with EtOAc. The combined organic layers were washed with 5% $NaHCO_3$ solution and brine, dried, filtered, and concentrated. The crude product was purified by flash chromatography eluting from silica gel with a gradient of 0-50% EtOAc in hexanes to afford 4.23 g of compound 13 as a colorless oil. MS: (+) m/z 484.3 (M+1-Boc).

Compound 14.

Di(1H-imidazol-1-yl)methanethione (1.5 g, 8.42 mmol) was added to a solution of compound 13 (2.46 g, 4.21 mmol) in THF (20 mL). The reaction mixture was refluxed overnight. LCMS showed the reaction went to completion. The solvent was evaporated. The crude product was purified by silica gel flash chromatography with a gradient of 0-50% EtOAc in hexanes to afford 1.25 g of compound 14 as a white solid. MS: (+) m/z 694.3 (M+1).

Compound 15.

(E)-2,2'-(diazene-1,2-diyl)bis(2-methylpropanenitrile) (AIBN, 0.016 g, 0.095 mmol) was added to a solution of compound 14 (1.78 g, 2.57 mmol) and tributylstannane (Bu3SnH, 1.380 mL, 5.13 mmol). The reaction mixture was refluxed for 30 min (oil bath temperature at 142° C.). The solvent was evaporated. The crude product was purified by flash chromatography eluting from silica gel with a gradient of 0-33% EtOAc in hexanes to afford 0.84 g of compound 15 as a light yellow oil. MS: (+) m/z 468.3 (M+1-Boc).

Compound 16.

LiOH (0.071 g, 2.96 mmol) in water (3.7 mL) was added to a solution of compound 15 (0.84 g, 1.480 mmol) in tetrahydrofuran (THF, 11.4 mL), followed by addition of 30% aq. $H_2O_2$ (0.271 mL, 8.88 mmol) at 0° C. After the reaction mixture was stirred at 0° C. for 4 h, 20 mL of 1.33 M aq. $Na_2SO_3$ was added to quench the reaction. Hydrochloric acid (1 M) was added to adjust the pH to 2-3. The resulting aqueous solution was extracted with DCM. The combined organic layers were dried, filtered, and concentrated. The crude product was purified by flash chromatography eluting from silica gel with a gradient of 0-75% EtOAc in hexanes to afford 0.53 g of compound 16 as a colorless oil. MS: (+) m/z 357.3 (M+1-Boc).

Compound 17.

Concentrated hydrochloric acid (4 drops) was added to a solution of 2,2-dimethoxypropane (3.53 mL, 28.7 mmol) and compound 16 (0.53 g, 1.161 mmol) in methanol (17.7 mL). The reaction mixture was stirred at RT overnight. LCMS showed the reaction went to completion. LCMS also showed the formation of some deprotected byproduct 16a. The solvent was evaporated.

Triethylamine (2.2 eq., 0.36 mL) was added to a solution of the above residue and $BOC_2O$ (1.2 eq., 304.3 mg) in acetonitrile at RT, to re-protect by-product 16a. The reaction mixture was stirred at RT for 2 h. LCMS showed the reaction went to completion. The solvent was evaporated. Water (7 mL) was added, and the aqueous solution was extracted with EtOAc. The combined organic layers were dried, filtered, and concentrated. The crude product was purified by flash chromatography eluting from silica gel with a gradient of 0-50% EtOAc in hexanes to afford 0.3 g of compound 17 as a colorless oil. MS: (+) m/z 371.3 (M+1-Boc).

Compound 18.

A mixture of compound 17 (0.223 g, 0.474 mmol) and Pd/C 10 wt % (20 mg, 0.474 mmol) in methanol (6 mL) was stirred under $H_2$ overnight. The Pd/C catalyst was filtered off, and the filtrate concentrated. The crude product was purified by flash chromatography eluting from silica gel with a gradient of 0-50% EtOAc in hexanes to afford 0.112 g of compound 18 as a white solid. MS: (+) m/z 237.2 (M+1-Boc).

Compound 19.

A mixture of compound 18 (0.204 g, 0.606 mmol), N-Ethyl-N'-(3-dimethylaminopropyl)carbodiimide hydrochloride (EDC, 0.174 g, 0.910 mmol), and Fmoc-protected citrulline 18a (0.361 g, 0.910 mmol) in DMF (12.4 mL) was stirred at RT overnight. Saturated $NH_4C_1$ solution (20 mL) was added to quench the reaction. The aqueous solution was extracted with EtOAc. The combined organic layers were dried, filtered, and concentrated. The crude product was purified by silica gel flash chromatography with a gradient of 0-30% MeOH in DCM to afford 0.25 g of compound 19 as a white solid. MS: (+) m/z 716.4 (M+1).

Compound 20.

Piperidine (0.5 mL, 5.06 mmol) was added to a solution of compound 19 (0.25 g, 0.349 mmol) in DMF (5 mL). After the reaction mixture was stirred at RT for 20 min, the solvent was evaporated to afford the Fmoc-deprotected intermediate as a residue.

DIEA was added to a solution of (S)-2-((((9H-fluoren-9-yl)methoxy)carbonyl)-amino)-3-methylbutanoic acid 19a (0.142 g, 0.418 mmol) and N,N,N',N'-tetramethyl-O-(7-azabenzotriazol-1-yl)uronium hexafluorophosphate (HATU, 0.146 g, 0.383 mmol) in DMF (2 mL), adjusting the pH to 8-9. After the reaction mixture was stirred at RT for 5 min, the above residue in DMF (1 mL) and DIEA were added to the reaction mixture, adjusting the pH to 8-9. After the reaction mixture was stirred at RT for 15 min, 20 mL of water containing 8 mL of 0.1% TFA water was added. The aqueous solution was extracted with EtOAc. The combined organic layers were dried, filtered, and concentrated. The crude product was purified by flash chromatography eluting from silica gel with a gradient of 0-20% MeOH in DCM to afford 0.24 g of compound 20 as a white solid. MS: (+) m/z 815.4 (M+1).

Compound 21.

Piperidine (0.3 mL) was added to a solution of compound 20 in DMF (3 mL). The reaction mixture was stirred at RT for 1 h. LCMS showed the reaction went to completion. The solvent was evaporated.

Lithium hydroxide (0.028 g, 1.176 mmol) in water (2 mL) was added to a solution of the above residue in THF (4 mL). After the reaction mixture was stirred at RT for 4 h, aq. HCl (0.1N) was added to acidify the reaction mixture (pH 2-3). The solvent was partially evaporated, and lyophilized to afford compound 21 as a white solid. MS: (+) m/z 579.4 (M+1).

Compound 22.

DIEA was added to a mixture of e-maleimidocaproic acid N-hydroxysuccinimide ester 21a (Tokyo Chemical Industry, 64.7 mg, 0.210 mmol) and compound 21 (81 mg, 0.14 mmol) in DMF (3 mL), adjusting pH 8-9. After the reaction mixture was stirred at RT for 2 h, 10 mL of 1:1 (v/v) mixture of acetonitrile and water containing 0.1% TFA was added. The product 22 was purified by preparative high performance liquid chromatography (HPLC). MS: (+) m/z 772.5 (M+1).

Compound 23.

2,2,2-Trifluoroacetic acid (0.7 mL, 0.013 mmol) was added to a mixture of compound 22 (30 mg, 0.039 mmol) in DCM (1 mL) at RT. After the reaction mixture was stirred at RT for 10 min, LCMS showed the reaction went to completion. The solvent was evaporated, affording compound 23. MS: (+) m/z 672.4 (M+1).

Compound (III-1).

DIEA was added to a solution of compound 9 (23.66 mg, 0.043 mmol) and HATU (14.77 mg, 0.039 mmol) in DMF (1 mL). The pH of the reaction mixture was adjusted to 8-9. After the reaction mixture was stirred at RT for 10 min, compound 23 (26.1 mg, 0.039 mmol) in DMF (1 mL) and DIEA were added. The pH of the reaction solution was adjusted to 8-9. After the reaction mixture was stirred at RT for 10 min, LCMS showed the reaction was complete. The reaction was quenched by addition of 10 mL 1:1 (v/v) mixture of water containing 0.1% TFA and acetonitrile. The product compound (III-1) was purified by prep HPLC. MS: (+) m/z 1207.7 (M+1).

Compounds such as (III-1), having a maleimido group, can be used to prepare conjugates by reaction with a sulfhydryl group on an antibody or other ligand. The sulfhydryl group can be one from a cysteine residue or one obtained by derivatization of a lysine residue with 2-iminothiolane.

Example 2

Compound (III-2)

Figure 1:
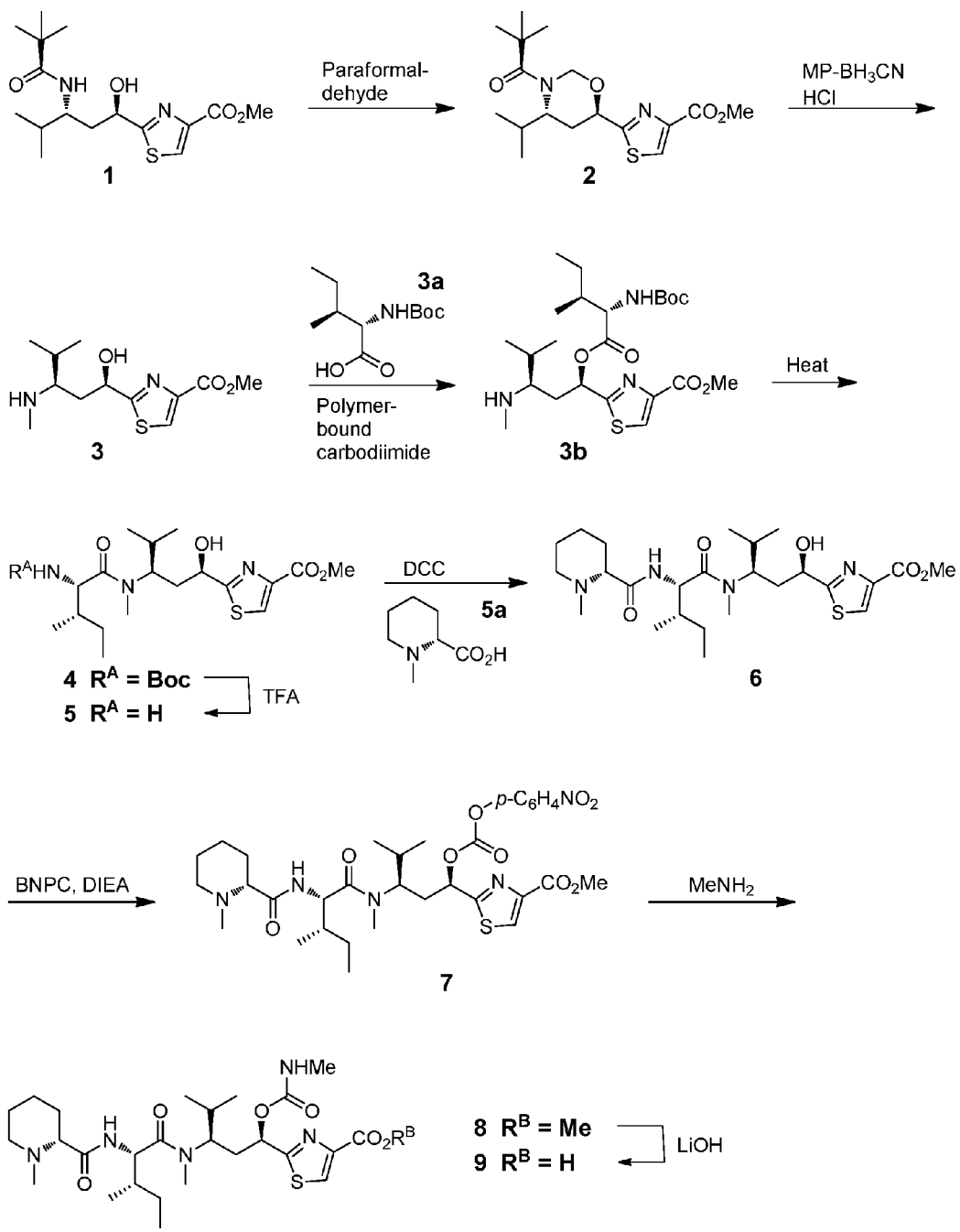
Figure 2A:
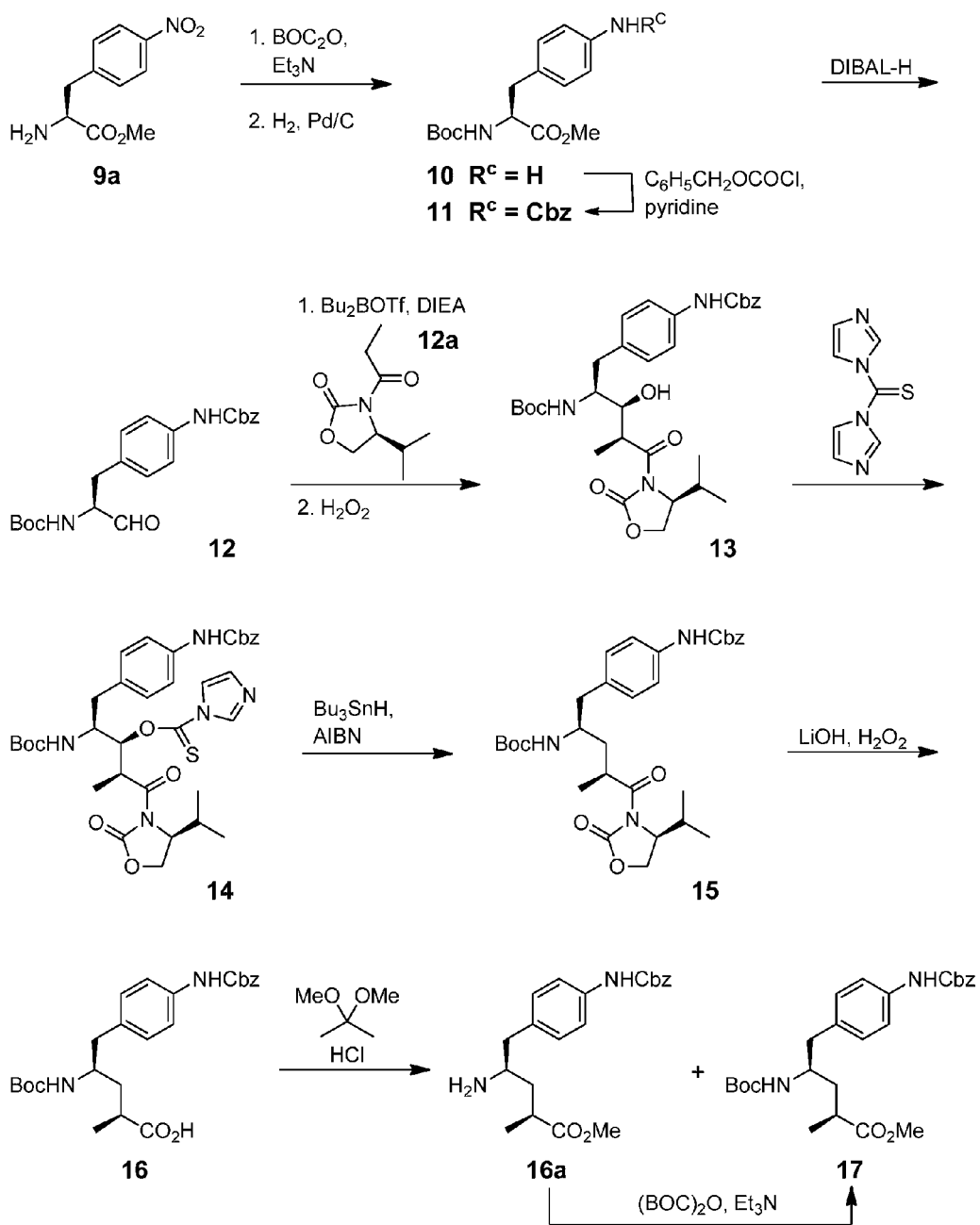
Figure 2B:
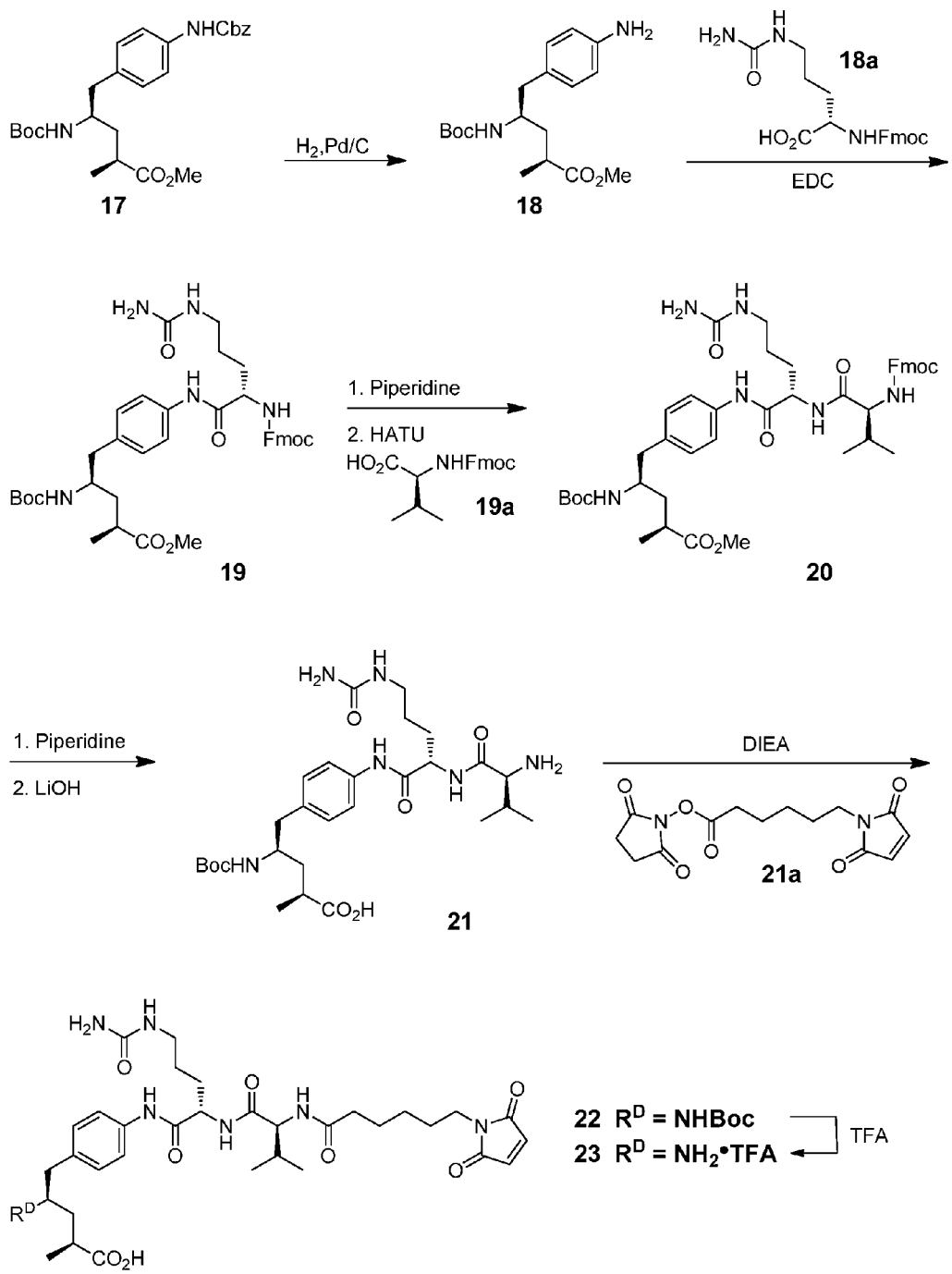
Figure 3:
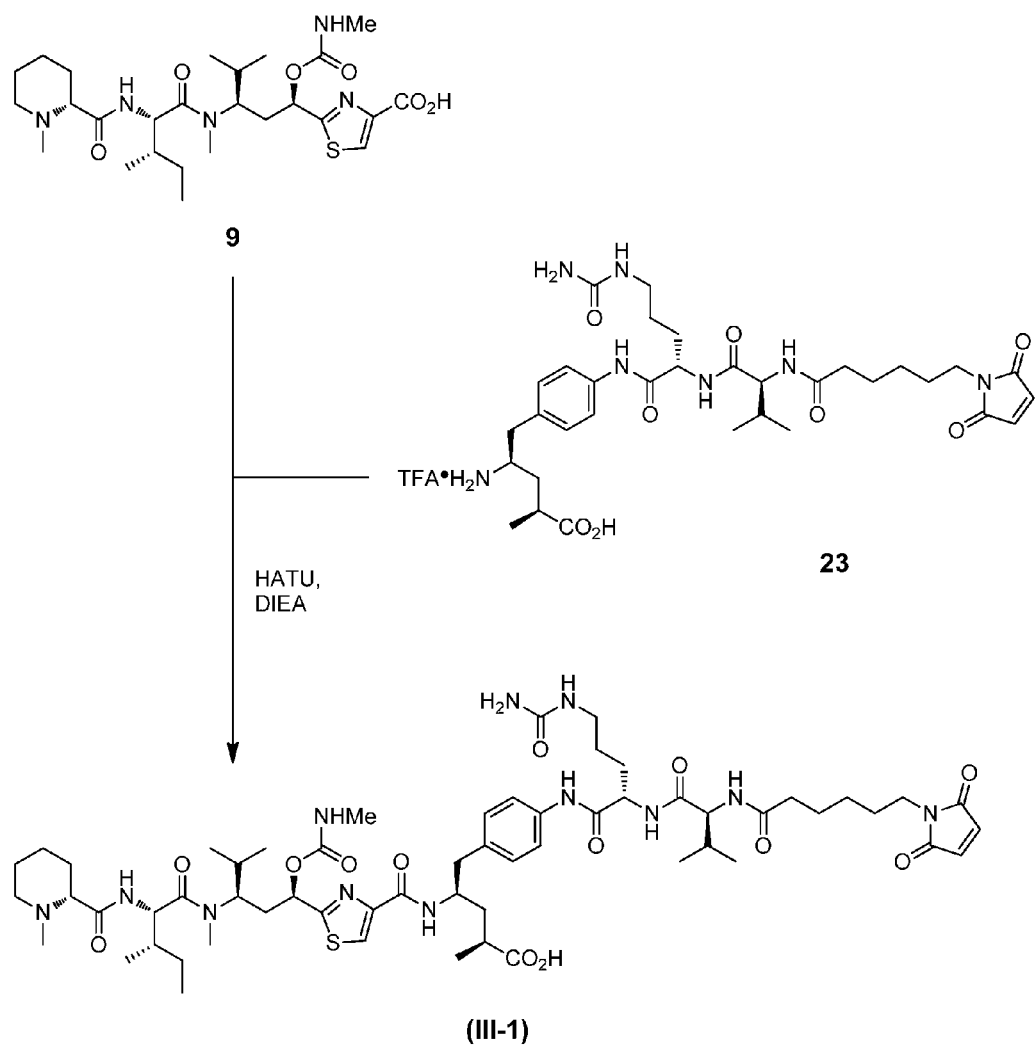
Figure 4:
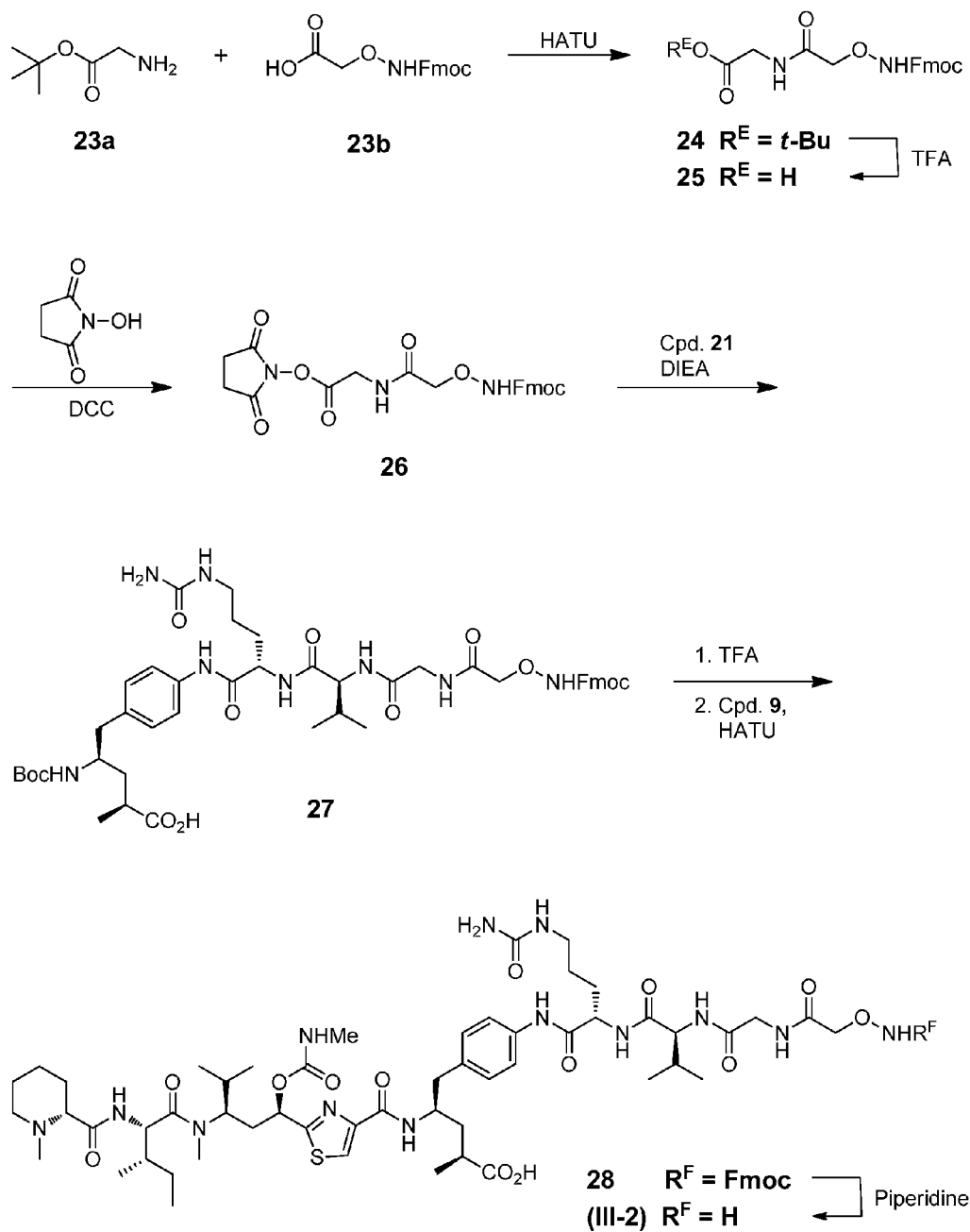
FIG. 4 shows a scheme for the synthesis of compound (III-2).

This example describes a synthesis of compound (III-2), the corresponding scheme being shown in FIG. 4.

Compound 24.

N-Ethyl-N-isopropylpropan-2-amine (0.556 mL, 3.19 mmol) was added to a solution of glycine tert-butyl ester hydrochloride 23a (0.209 g, 1.596 mmol), Fmoc-aminoxyacetic acid 23b (0.5 g, 1.596 mmol) and HATU (0.607 g, 1.596 mmol) in DMF (5 mL) at RT. After the reaction mixture was stirred at RT for 1 h, 0.1% aq. TFA (20 mL) was added. The aqueous solution was extracted with EtOAc, and the combined organic layers were dried, filtered, and concentrated. The crude product was purified by flash chromatography eluting from silica gel with a gradient of 0-70% EtOAc in hexanes to afford 0.45 g of compound 24 as a colorless oil. MS: (+) m/z 449.2 (M+23).

Compound 25.

TFA (3 mL, 1.437 mmol) was added to a solution of compound 24 (0.45 g, 1.055 mmol) in DCM (0.5 mL) at RT. The reaction mixture was stirred at RT overnight. The solvent was evaporated. The crude product was purified by flash chromatography eluting from silica gel with a gradient of 0-30% MeOH in DCM to afford 0.39 g of compound 25 as a white solid. MS: (+) m/z 371.1 (M+1).

Compound 26.

N,N'-methanediylidenedicyclohexanamine (DCC, 0.261 g, 1.267 mmol) was added to a solution of compound 25 and 1-hydroxypyrrolidine-2,5-dione (0.146 g, 1.267 mmol) in DCM (6 mL) at RT. After the reaction mixture was stirred at RT overnight, the solid was filtered off. The filtrate was then concentrated. The crude product was purified by flash chromatography eluting from silica gel with a gradient of 0-100% EtOAc in hexanes to afford 0.43 g of compound 26 as a colorless oil.

Compound 27.

DIEA was added to a solution of compound 21 (50 mg, 0.086 mmol) and compound 26 (60.6 mg, 0.130 mmol) in DMF at RT, adjusting the pH to 8-9. After the reaction mixture was stirred at RT for 4 h, the reaction was quenched by addition of 10 mL of 1:1 mixture of 0.1% aq. TFA and acetonitrile. Preparative HPLC purification afforded 55 mg of compound 27 as a white solid, MS: (+) m/z 931.4 (M+1).

Compound 28.

TFA (1 mL, 0.059 mmol) was added to a solution of compound 27 (55 mg, 0.059 mmol) in DCM (2 mL) at RT. The reaction mixture was stirred at RT for 10 min. The solvent was evaporated.

DIEA was added to a solution of compound 9 (32.7 mg, 0.059 mmol) and HATU (22.47 mg, 0.059 mmol) in DMF (1 mL). The pH of the reaction mixture was adjusted to 8-9. After the reaction mixture was stirred at RT for 10 min, DMF (2 mL) and DIEA were added. The pH of the reaction solution was adjusted to 8-9. After the reaction mixture was stirred at RT for 10 min, LCMS showed the reaction was complete. The reaction was quenched by addition of 20 mL 1:1 (v/v) mixture of water containing 0.1% TFA and acetonitrile. Preparative HPLC purification afforded 70 mg of compound 28 as a white solid. MS: (+) m/z 684.1 (M/2+1).

Compound (III-2).

Piperidine was added to a solution of compound 28 (70 mg, 0.051 mmol) in DMF (4 mL). After the reaction mixture was stirred at RT for 20 min, a 1:1 mixture of acetonitrile and 0.1% aq. TFA (40 mL) was added. Preparative HPLC purification afforded 46 mg of compound (III-2) as a white solid. MS: (+) m/z 1144.6 (M+1).

Compounds such as (III-2), having a hydroxylamine group, can be used to form conjugates with an antibody or other ligand having an aldehyde or ketone functionality, for example by incorporation of the unnatural amino acid 4-acetylphenylalanine.

Example 3

Compounds (I-2) and (I-3)

Figure 5:
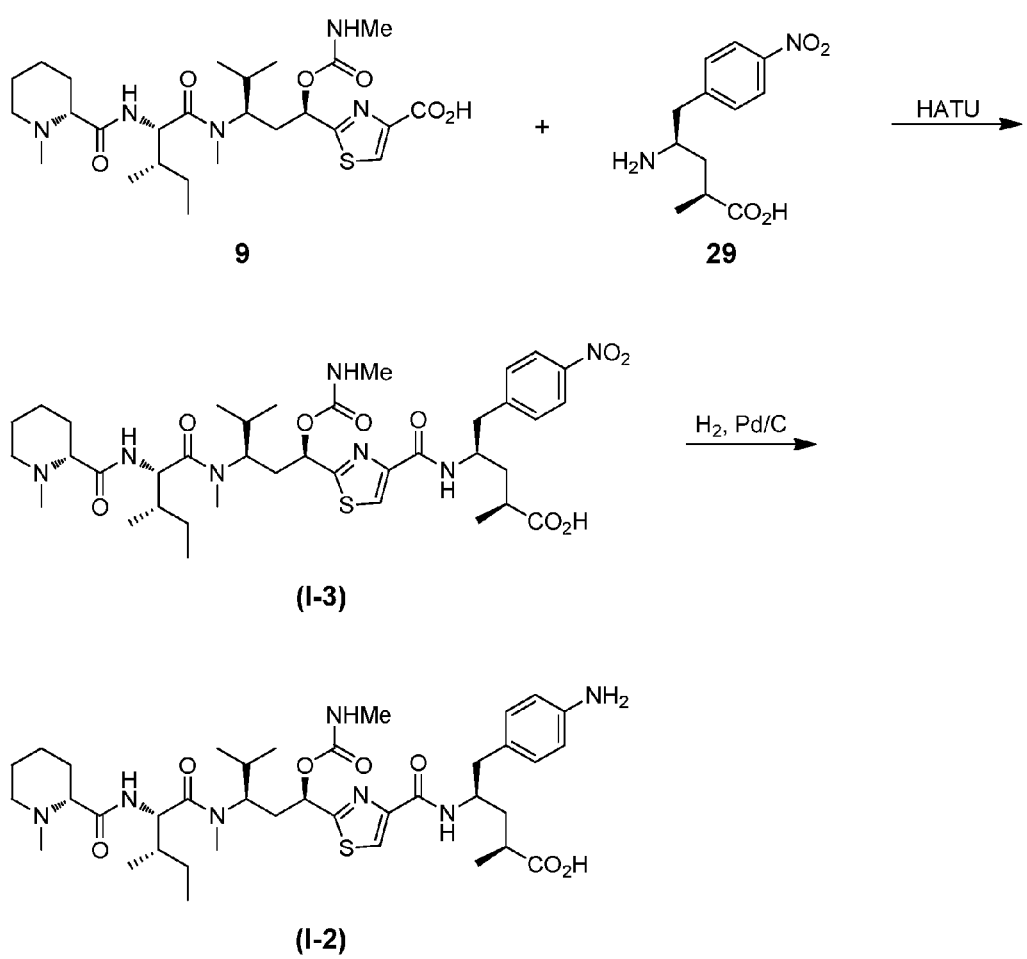
FIG. 5 shows a scheme for the synthesis of compounds (I-2) and (I-3).

The synthesis of compounds (I-2) and (I-3) is shown schematically in FIG. 5.

Compound (I-3).

DIEA was added to a solution of compound 9 (10 mg, 0.018 mmol) and HATU (6.87 mg, 0.018 mmol) in DMF (0.3 mL), adjusting the pH to 8-9. After the reaction mixture was stirred at RT for 10 min, compound 29 (prepared according to Cheng et al. 2011, Example 17; 4.56 mg, 0.018 mmol) in DMF (0.5 mL) and DIEA were added, adjusting pH to 8-9. After the reaction mixture was stirred at RT for 20 min, the reaction was quenched by addition of 4 mL of 1:1 mixture of acetonitrile and 0.1% aq. TFA. Preparative HPLC purification afforded 12 mg of compound (I-3) (I-2) as a white solid. MS: (+) m/z 788.4 (M+1).

Compound (I-2).

A mixture of compound (I-3) (12 mg, 0.015 mmol) and Pd/C, 10 wt % (4 mg, 0.015 mmol) in methanol (0.5 mL) was stirred under an $H_2$ atmosphere overnight. The catalyst was filtered off, and the filtrate concentrated. Preparative HPLC purification afforded 8.1 mg of compound (I-2) as a white solid. MS: (+) m/z 758.4 (M+1).

Compound (I-1) can be analogously prepared by replacing compound 29 with the compound having mixed stereochemistry at the alpha-methyl position (Cheng et al. 2011).

Example 4

Compound (III-4)

Figure 6A:
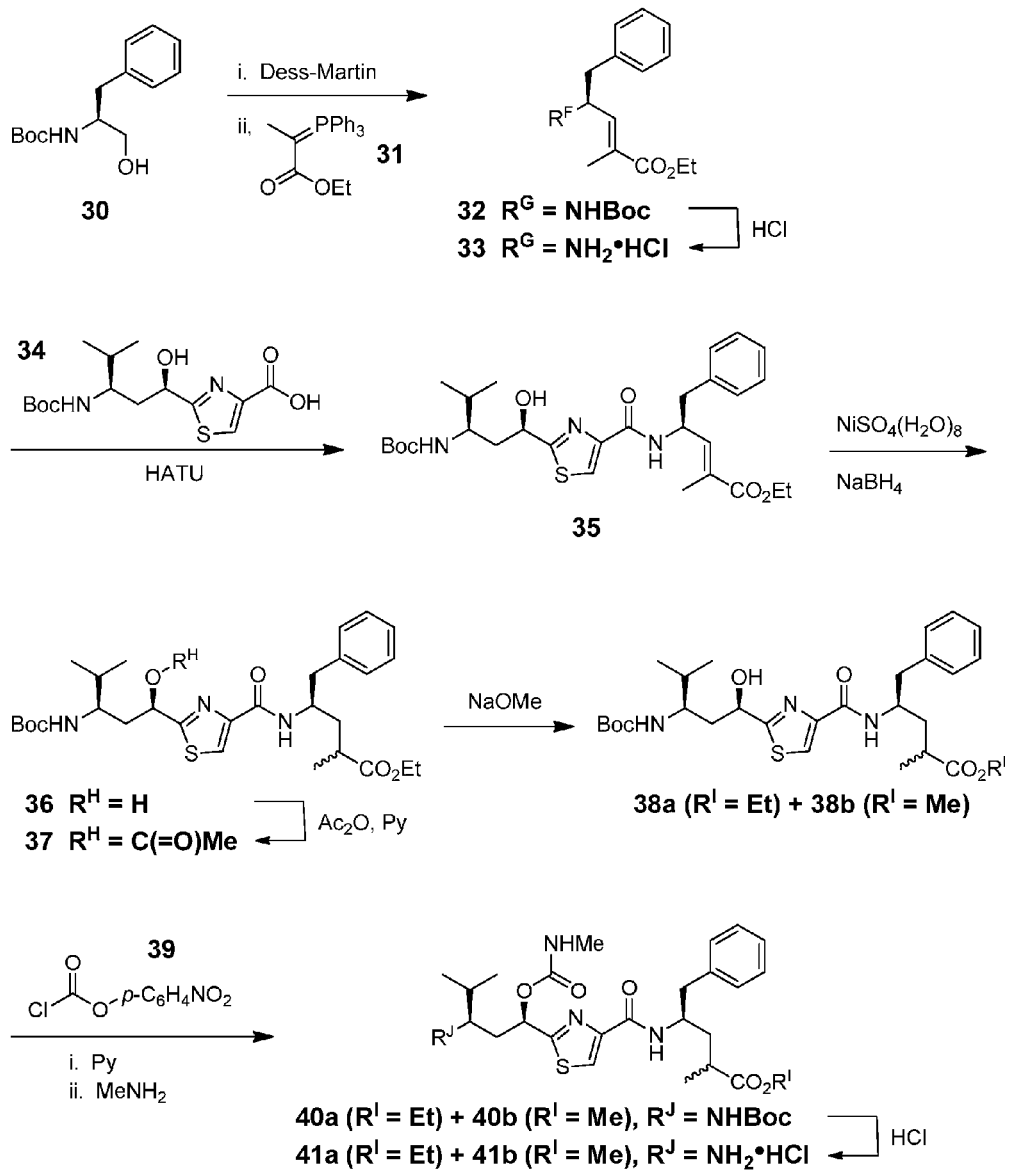
FIGS. 6a-6c show in combination a scheme for the synthesis of compounds (III-4) and (III-5).
Figure 6B:
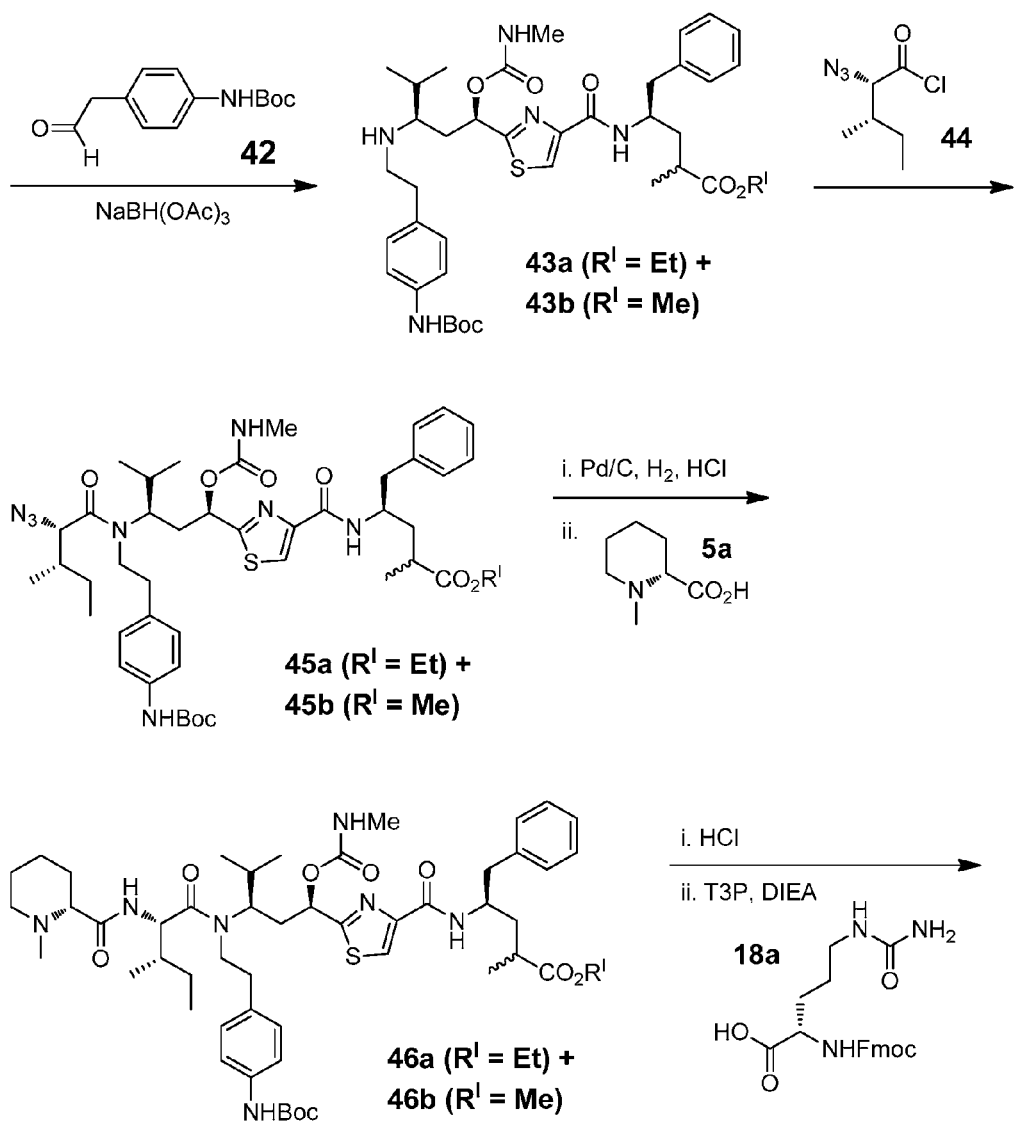
Figure 6C:
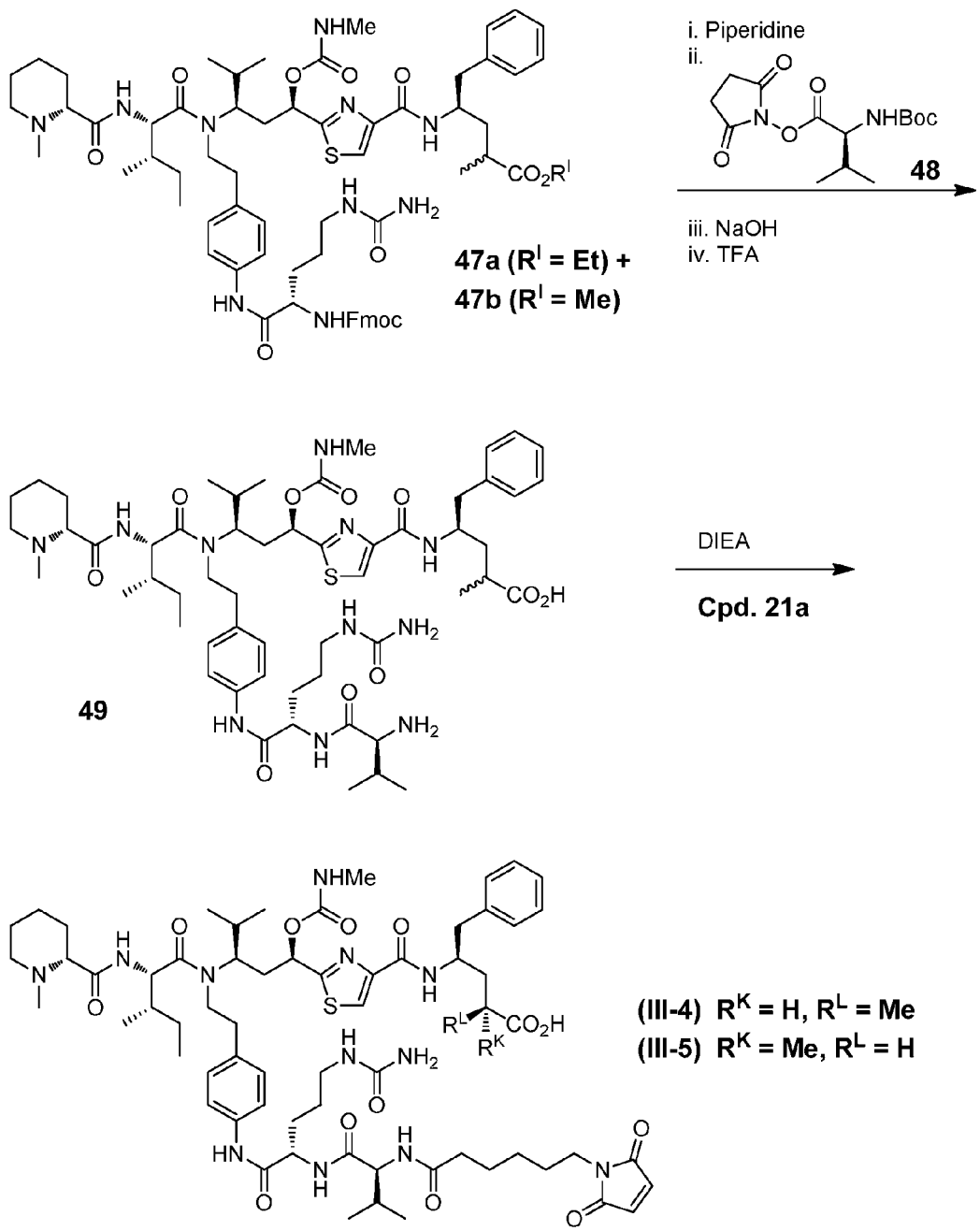

FIGS. 6a through 6c in combination show schematically the synthesis of compound (III-4).

Compound 32.

Compound 30 (Aldrich, 3.5 g, 13.9 mmol) was dissolved in 50 mL DCM. To this solution was added Dess-Martin periodinane (11.8 g, 27.9 mmol) at 5° C. After 10 min the mixture was warmed to RT. After another hour the reaction was quenched with saturated aq. $NaHCO_3$ and saturated aq. $NaS_2O_3$. After extraction with ether, the ether extract was washed with aq. $NaHCO_3$ and then brine and dried and evaporated down to a sticky oil. The oil was dissolved in 50 mL of DCM, to which was added the commercially available compound 31 (5.05 g, 13.93 mmol). After 10 min the reaction mixture was taken up in EtOAc, washed with aq. $NaHCO_3$ and then brine and dried, filtered and the solvent evaporated. After column chromatography (EtOAc: hexane, 0-20% gradient) compound 32 (2.3 g, 6.90 mmol, 49.5% yield) was obtained as a white solid. It had an NMR spectrum consistent with literature (Wipf et al. 2004a).

Compound 33.

Hydrochloric acid (7.80 mL, 31.2 mmol, 4M in dioxane) was added at 5° C. to a DCM solution of compound 32 (5.2 g, 15.60 mmol). After the deprotective reaction was complete, the reaction mixture was evaporated and compound 33 (4.21 g, 15.60 mmol, 100% yield, hydrochloride) was obtained as a white solid, which is used for next step without further purification.

Compound 35.

To a solution of compound 34 (prepared per Sani et al. 2007, 4.00 g, 11.6 mmol) in 20 mL DMF at 5° C. were added HATU (4.61 g, 12.12 mmol) and DIPEA (6 ml, 34.4 mmol). After 10 min compound 33 (2.71 g, 11.60 mmol) was added. After another half hour the mixture was taken up in EtOAc, which was washed with 10% aq. citric acid, saturated aq.$NaHCO_3$ and brine. After drying and filtration, the organic phase was evaporated down to give compound 35 (6.49 g, 11.60 mmol, 100% yield, [M+Na]$^+$, calculated 582.3. found 582.3) as an oil, which was used for next step without further purification.

Compound 36.

$NaBH_4$ (4.66 g, 123 mmol) was added, in portions, to a 100 mL methanol solution of compound 35 (6.49 g, 11.6 mmol) and $NiSO_4(H_2O)_6$ (6.48 g, 24.66 mmol) at 5° C. (Caution: Hydrogen was generated.) After 30 min, saturated aq. $NaHCO_3$ was added, followed by EtOAc. After filtration through CELITE™, the organic phase was separated from the aqueous phase, washed with brine, dried, filtered and evaporated down to give compound 36 (5.6 g, 9.97 mmol, 81% yield, [M+1]$^+$, calculated 562.3. found 562.4), which was used for next step without further purification.

Compound 37.

Compound 36 (5.6 g, 9.97 mmol) was dissolved in 30 mL pyridine at 5° C. Acetic anhydride (4 g, 39.2 mmol) was added to this solution. After 10 min the mixture was warmed to RT. After about an hour the reaction mixture was concentrated down. The resulting residue was taken up in EtOAC and the organic phase was washed with 10% aq. citric acid, saturated aq. $NaHCO_3$, and brine, sequentially. The organic phase was dried, filtered and concentrated to give compound 37 (5.8 g, 9.61 mmol, 100% yield, [M+1]$^+$, calculated 604.3. found 604.4), which was used for next step without further purification.

Compounds 38a and 38b.

Compound 37 (0.8 g, 1.3 mmol) was dissolved in 5 mL methanol at −78° C. To this solution was added NaOMe (331 uL, 1.33 mmol, 4M in MeOH). The mixture was allowed to warm up to RT over 1 hr. The mixture was taken up in EtOAc, washed with 10% aq. citric acid, saturated aq. $NaHCO_3$ solution, and brine. The separated organic phase was dried, filtered and evaporated to give a mixture of ethyl and methyl esters (compounds 38a and 38b, respectively). The mixture of esters was not separated during the next few steps, until both were hydrolyzed to the carboxylic acid at a later step.

Compounds 40a and 40b.

The mixture of compounds 38a and 38b from the above reaction was dissolved in 20 mL DCM. To this solution was added 4-nitrophenyl carbonochloridate 39 (524 mg, 2.6 mmol) and pyridine (210 μl, 2.6 mmol) at 5° C. The temperature was allowed to rise to room temperature after 1 h and methylamine (1.950 mL, 3.9 mmol, 2M in THF) was added. After 10 min the solvent was evaporated and the residue was passed through a chromatography column to give a mixture of compounds 40a and 40b (ethyl and methyl esters, respectively; 420 mg, 40a/40b ratio 3:1 from HPLC, about 53% yield for two steps, [M+1]$^+$: calculated 603.3. found 603.4 for 40a; calculated 589.3. found 589.4 for 40b).

Compounds 41a and 41b.

The mixture of compounds 40a and 49b (420 mg, about 0.68 mmol) was dissolved in 3 mL DCM, to which was added HCl (4.8 mmol, 1.2 mL, 4N in dioxane). After 1 h at 5° C. the solvent was evaporated and the mixture of compounds 41a (ethyl ester) and 41b (methyl ester), ratio about 3:1, was used for next step without further purification.

Compounds 43a and 43b.

A mixture of compounds 41a and 41b (400 mg, ≈0.72 mmol), compound 42 (commercially available from Anichem, 170 mg, 0.721 mmol) and acetic acid (0.041 mL, 0.721 mmol) were mixed in DCM at 5° C. Sodium triacetoxyborohydride (306 mg, 1.44 mmol) was added. The mixture was taken up in EtOAc after 30 min. After washed with 7% aq. $K_2CO_3$ and brine, the organic phase was dried, filtered and evaporated down to give a residue. After column chromatography purification (MeOH: DCM, 0-7% gradient), compounds 43a (ethyl ester) and 43b (methyl ester) were obtained (310 mg, approximately 0.42 mmol, approximately 58.3% yield, 43a:43b ratio about 3:1, [M+1]$^+$, calculated 738.4. found 738 for 43a; calculated 724.4. found 724 for 43b).

Compounds 45a and 45b.

A mixture of compounds 43a and 43b (310 mg, approximately 0.42 mmol) was dissolved in 5 mL DCM at RT. To this solution were added 2,6-di-tert-butylpyridine (161 mg, 0.840 mmol) and a 2 mL DCM solution of compound 44 (prepared per Peltier et al. 2006, 73.8 mg, 0.420 mmol). After half an hour Et$_3$N (58.6 µl, 0.420 mmol) was added. The mixture was then taken up in EtOAc, which was washed with 10% aq. citric acid, saturated aq. NaHCO$_3$ solution and brine. The organic phase was dried, filtered and evaporated down to a residue. After column chromatography purification, compounds 45a and 45b were obtained (294 mg, approximately 0.334 mmol, 80% yield, 45a:45b ratio 3:1, [M+1]$^+$, calculated 877.5. found 877 for 45a; calculated 863.5 found 863 for 45b) as a sticky oil.

Compounds 46a and 46b.

A mixture of compounds 45a and 45b (100 mg, approximately 0.114 mmol) was added to a suspension of Pd/C (65 mg, 10%) in 20 mL MeOH. HCl (28.5 µL, 0.114 mmol, 4M in dioxane) was added. The flask was evacuated and refilled with H$_2$, this process being repeated three times. After 2 h the suspension was filtered and the solvent was evaporated to give a residue. A suspension of compound 5a (19.59 mg, 0.137 mmol) in 500 uL DMF, HATU (43.4 mg, 0.114 mmol) and DIPEA (49.8 µl, 0.285 mmol) were added at 5° C. After the suspension became homogeneous the above residue was added as a DMF (1 mL) solution. More DIPEA was added to adjust the pH to about 12. After 10 min the mixture was taken up in EtOAc, which was washed with 10% aq. citric acid, saturated aq. NaHCO$_3$ and brine. The separated organic phase was dried, filtered and evaporated. The resulting residue was passed through a chromatographic column to give a mixture of compounds 46a and 46b (ethyl and methyl esters, respectively, 80 mg, about 0.082 mmol, 71.9% yield, 46a:46b ratio 3:1, [M+1]$^+$, calculated 976.5. found 976.5 for 46a; calculated 962.5. found 962.5 for 46b).

Compounds 47a and 47b.

HCl (256 µl, 1.024 mmol, 4M in dioxane) was added to a 2 mL MeOH solution of compounds 46a and 46b (200 mg, 0.205 mmol) at 5° C. After 1 h the solution was evaporated down and dried on high vacuum overnight to give a sticky oil. This sticky oil, Fmoc-protected citrulline 18a (81 mg, 0.205 mmol), and DIPEA (179 µl, 1.024 mmol) were dissolved in 2 mL DMF at RT. Propylphosphonic acid anhydride (T3P, 178 µL, 0.410 mmol, 2.3 M in EtOAc) was added. After 1 h the reaction mixture was taken up in EtOAc, which was washed with saturated aq. NaHCO$_3$ solution and brine. After separation, drying and evaporation, the resulting residue was passed through a chromatography column (MeOH: DCM, 0-10% gradient) to give a mixture of compounds 47a and 47b (ethyl and methyl esters, respectively, 150 mg, approximately 0.119 mmol, about 58.3% yield, 47a:47b ratio 3:1, [M+1]$^+$, calculated 1255.6. found 1255.6 for 47a; calculated 1241.6. found 1241.6 for 47b).

Compound 49.

A mixture of compounds 47a and 47b (200 mg, about 0.165 mmol) was dissolved in 5 mL of DMF (with 5% piperidine) at room temperature. The solution was evaporated to dryness after 30 min. The resulting residue was mixed with Boc-protected valine N-hydroxysuccinimide ester 48 (61.9 mg, 0.198 mmol), 5 mL DMF and DIPEA (87 µL, 0.496 mmol). After allowing reaction to proceed overnight, the reaction mixture was evaporated to dryness. The resulting mixture was dissolved in a 5 mL mixture of MeOH, THF and water (1:1:1). NaOH was added and the pH of the final solution was 14. After allowing reaction to proceed overnight at RT, the mixture was acidified with HCl to a pH of 3 and evaporated under high vacuum. The obtained solid was treated with TFA and the mixture was evaporated after 10 min, affording compound 49 (80 mg, 0.072 mmol, 43.8% yield, [M+1]$^+$, calculated 1104.6. found 1104.6) after preparative HPLC purification.

Compound (III-4).

Compound 49 (80 mg, 0.072 mmol), commercially available compound 21a (Aldrich, 26.6 mg, 0.087 mmol) and DIPEA (38.0 µl, 0.217 mmol) were dissolved in 2 mL of DMF. After reaction was allowed to proceed overnight, the mixture was evaporated down and the residue was purified by preparative HPLC to give a major isomer (15 mg, 16% yield, ½[M+2]$^{2+}$, calculated 649.3. found 649.5) and a minor isomer (3.7 mg, 4% yield, ½[M+2]$^{2+}$, calculated 649.3. found 649.5)). The major isomer was tentatively assigned as (III-4), having the natural tubulysin stereochemistry at the alpha-methyl of the Tup subunit and the minor isomer was assigned as compound (III-5), having the inverted stereochemistry there.

Example 5

Compounds (I-5), (I-6), and (I-7)

A small portion of the sticky oil described above from the treatment of compounds 46a and 46b with HCl was not coupled to compound 18a but was instead dissolved in a mixture of THF, MeOH and water (1:1:1). The pH of the reaction mixture was adjusted to 14. After allowing the reaction to proceed overnight, half of the reaction mixture was evaporated and purified by preparative chromatography to give compounds (I-5) (1 m; M+1, 876.6), (I-6) (1 mg; M+1, 862.5) and (I-7) (1 mg; M+1, 848.5).

Example 6

Compound (I-1)

Figure 7:
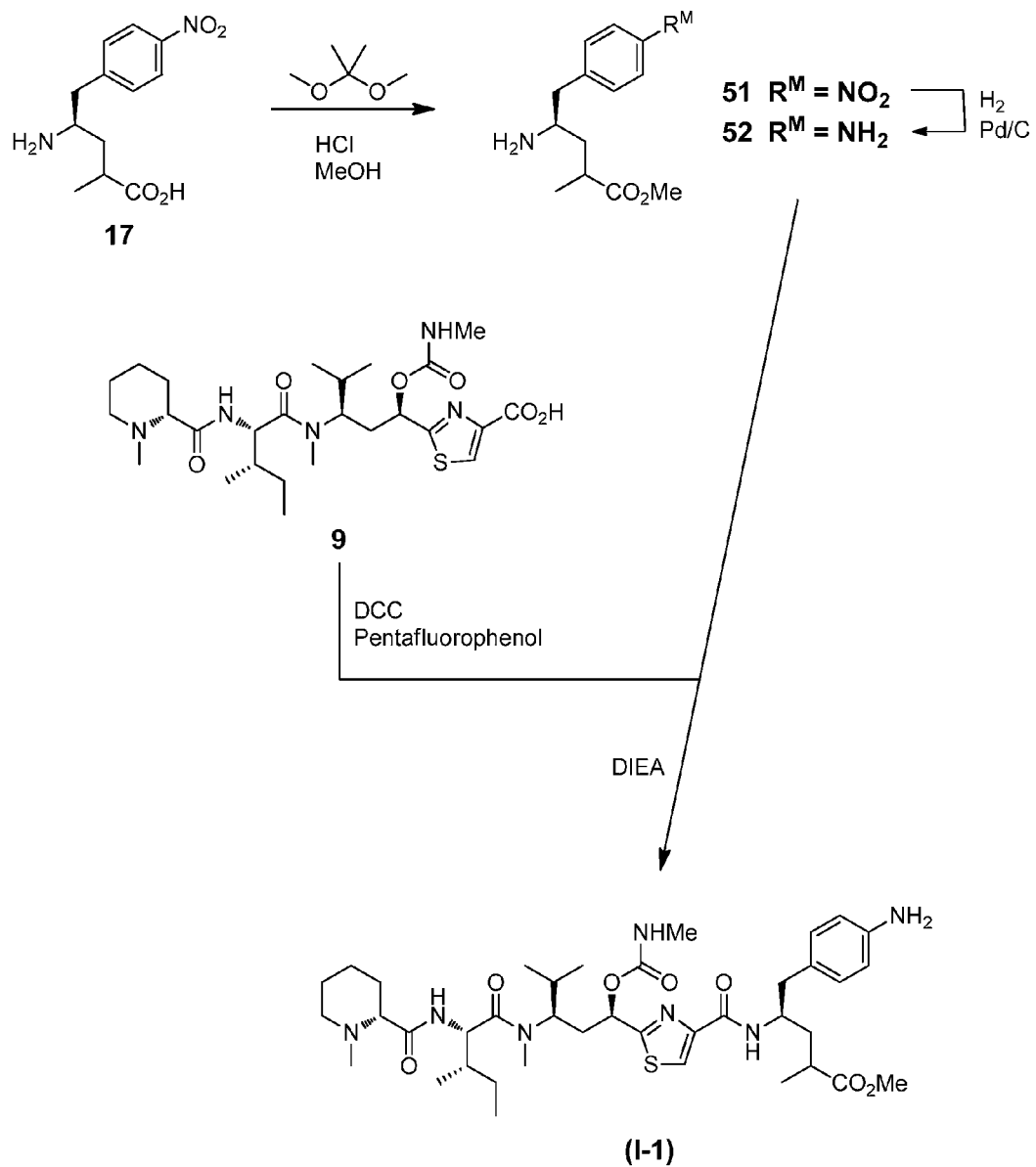
FIG. 7 shows a scheme for the synthesis of compound (I-1).

A scheme for the synthesis of compound (I-1) is shown in FIG. 7.

Compound 51.

HCl (6 N, 0.2 mL) was added to a solution of compound 50 (Cheng et al. 2011; 50 mg, 0.198 mmol) and 2,2-dimethoxypropane (0.244 mL, 1.982 mmol) in MeOH (1 mL). After the reaction mixture was stirred at RT overnight, the solvent was evaporated to afford 52.8 mg of compound 51. MS: (+) m/z 267.2 (M+1).

Compound 52.

A mixture of compound 51 (52.8 mg, 0.198 mmol) and palladium on carbon (10 wt %, 8 mg) in MeOH (1 mL) was stirred under an H$_2$ atmosphere overnight. The catalyst was then filtered off and the solvent evaporated to afford 46.9 mg of compound 52. MS: (+) m/z 237.3 (M+1).

Compound (I-1). A mixture of pentafluorophenol (2.493 mg, 0.014 mmol), 1,3-dicyclohexylcarbodiimide (2.049 mg, 9.93 µmol), and compound 9 (5 mg, 9.03 µmol) in DCM (0.5 mL) was stirred at RT overnight. The solvent was then evaporated.

To a solution of the resulting residue (6.50 mg, 9.03 µmol) and compound 52 (4.27 mg, 18.06 µmol) in DMF (0.2 mL) was added DIEA (1 drop). After the reaction mixture was stirred at RT for 10 min, the reaction was quenched by addition of a 1:1 mixture of acetonitrile and water containing 0.1% TFA (4 mL). Preparative HPLC purification afforded 2.5 mg of compound (I-1) as a white solid. MS: (+) m/z 772.5 (M+1).

Example 6

Compound (I-4)

Figure 8:
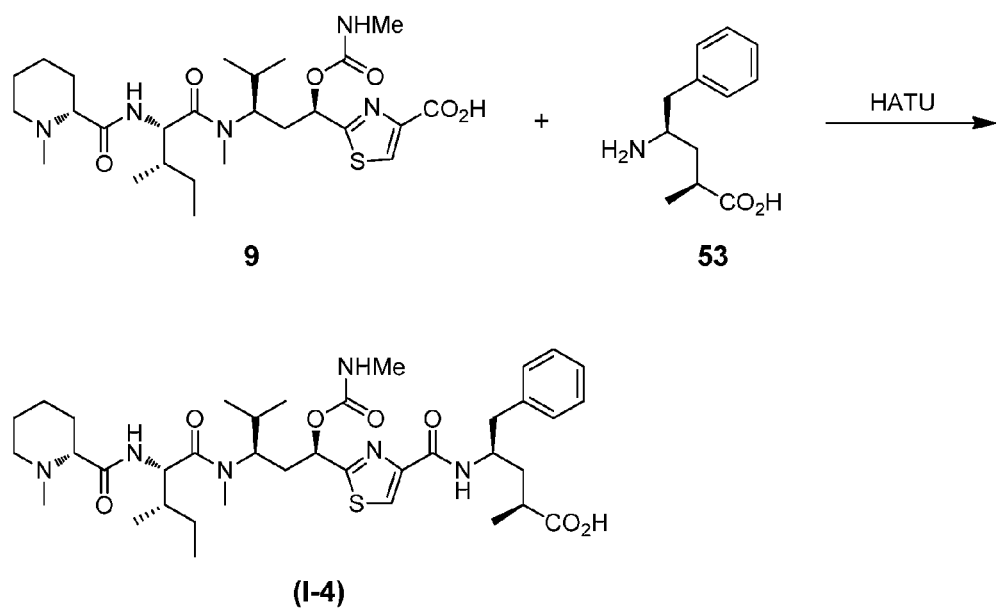
FIG. 8 shows a scheme for the synthesis of compound (I-4).

FIG. 8 shows a scheme for the synthesis of compound (I-4).

DIEA was added to a solution of compound 9 (10.69 mg, 0.019 mmol) and HATU (7.34 mg, 0.019 mmol) in DMF (0.3 mL), adjusting pH to 8-9. After the reaction mixture was stirred at rt for 10 min, compound 53 (4 mg, 0.019 mmol; prepared according to Sani et al. 2007) in DMF (0.5 mL) and DIEA were added, adjusting the pH to 8-9. After the reaction mixture was stirred at RT for 20 min, the reaction was quenched by addition of a 1:1 mixture of acetonitrile and water containing 0.1% TFA (4 mL). Preparative HPLC purification afforded 12.5 mg of compound (I-4) as a white solid. MS: (+) m/z 743.4 (M+1).

Example 7

Thiocarbamates

Compounds according to formula (I) in which W is S (that is, thiocarbamates) can be made by treating a suitable precursor such as compound 6 (FIG. 1) with sodium hydride and then a thioisocyanate, as illustrated below:

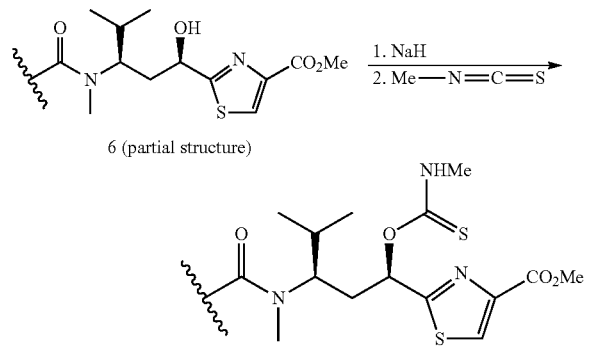

Example 8

Compound (III-6)

Figure 9A:
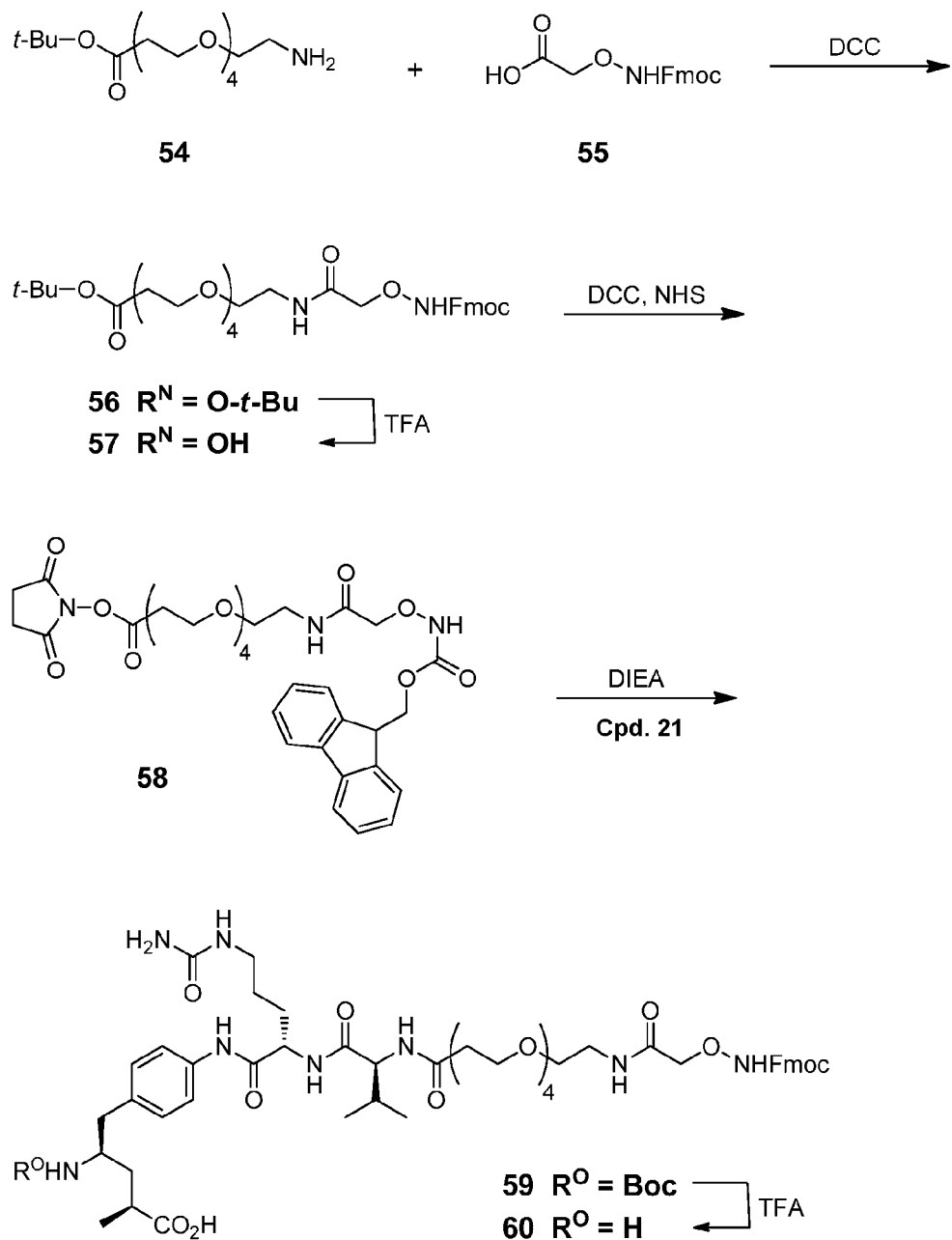
FIGS. 9a and 9b show in combination a scheme for the synthesis of compound (III-6).
Figure 9B:
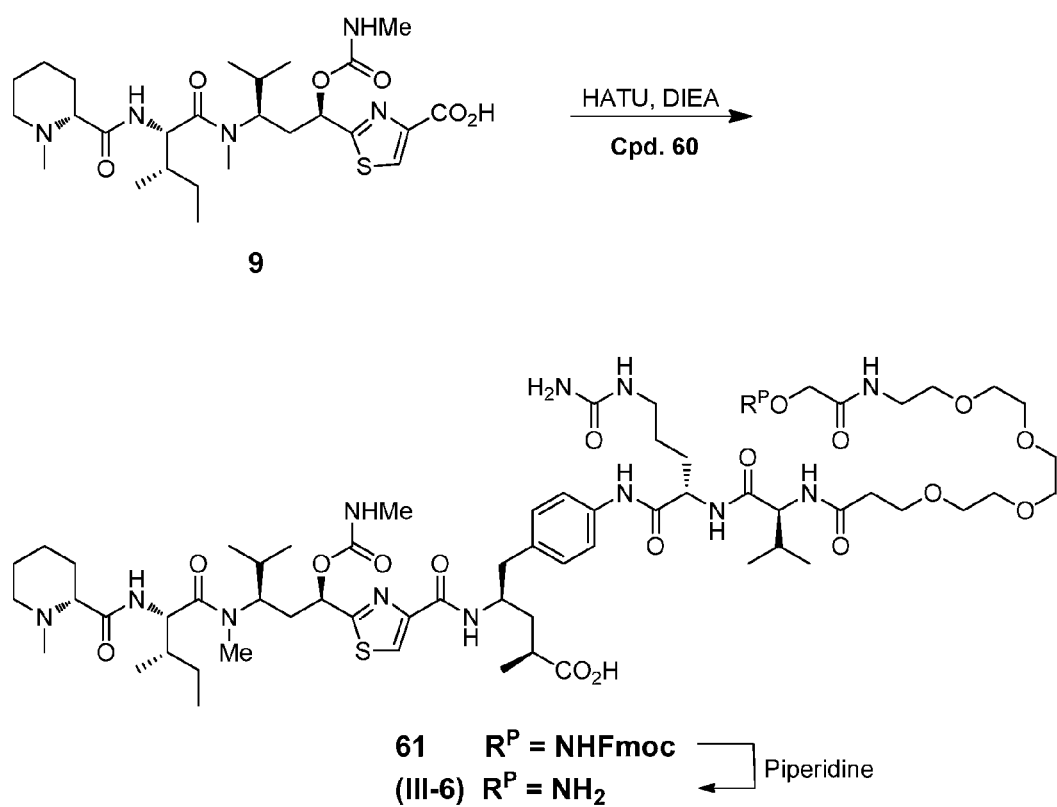

A scheme for the synthesis of compound 56 is shown in FIGS. 9a and 9b.

Compound 56.

1,3-Dicyclohexylcarbodiimide (DCC, 0.160 g, 0.778 mmol) was added to a solution of tert-butyl 1-amino-3,6,9,12-tetraoxapentadecan-15-oate 54 (Quanta Biosciences, 0.25 g, 0.778 mmol) and 2-(((((9H-fluoren-9-yl)methoxy)carbonyl)amino)-oxy)acetic acid 55 (Chem-Impex, 0.244 g, 0.778 mmol) in DCM (5 mL) at RT. After the reaction mixture was stirred at RT overnight, the precipitate was filtered off. The filtrate was then concentrated. The crude product was purified by flash chromatography eluting from silica gel with a gradient of 0-10% methanol in DCM to afford 0.30 g of compound 56 as a colorless oil. MS: (+) m/z 617.4 (M+1).

Compound 57.

A solution of compound 56 (0.303 g, 0.491 mmol) in TFA (2 mL, 0.662 mmol) was stirred at RT for 2 h. After the solution was concentrated, the residue was washed with hexanes to afford 0.28 g of compound 57. MS: (+) m/z 561.3 (M+1).

Compound 58.

DCC (0.199 g, 0.963 mmol) was added to a solution of compound 57 (0.27 g, 0.482 mmol) and 1-hydroxypyrrolidine-2,5-dione (also known as N-hydroxysuccinimide or NHS, 0.111 g, 0.963 mmol) in DCM (5 mL) at RT. After the reaction mixture was stirred at RT overnight, the solid was filtered off. The filtrate was then concentrated. The crude product was purified by flash chromatography eluting from silica gel with a gradient of 0-100% ethyl acetate in hexanes to afford 0.12 g of compound 58 as a colorless oil. MS: (+) m/z 658.3 (M+1).

Compound 59.

DIEA (2 drops) was added to a solution of compound 58 (0.12 g, 0.182 mmol) and compound 21 (0.106 g, 0.182 mmol) in DMF (2 mL) at RT. After the reaction mixture was stirred at RT for 1 h, the reaction was quenched by addition of a mixture of acetonitrile and water containing 0.1% TFA. The crude product was purified by prep HPLC to afford 0.12 g of compound 59 as a white solid. MS: (+) m/z 1121.6 (M+1).

Compound 60.

TFA (0.5 mL) was added to a solution of compound 59 (20 mg, 0.018 mmol) in DCM (1 mL) at RT. After the reaction mixture was stirred at RT for 20 min, the solution was concentrated to afford 18.2 mg of compound 60. MS: (+) m/z 1021.6 (M+1).

Compound 61.

DIEA was added to a solution of compound 9 (9.87 mg, 0.018 mmol) and HATU (6.78 mg, 0.018 mmol) in DMF (0.4 mL). The pH of the reaction mixture was adjusted to 8-9. After the reaction mixture was stirred at RT for 10 min, compound 60 (18.2 mg, 0.018 mmol) in DMF (1 mL) and DIEA were added. The pH of the reaction mixture was adjusted to 8-9. After the reaction mixture was stirred at RT for 10 min, the reaction was quenched by addition of 10 mL 1:1 (v/v) mixture of water containing 0.1% TFA and acetonitrile. The crude product was purified by prep HPLC to afford 25 mg of compound 61 as a white solid. MS: (+) m/z 779.0 (M/2+1).

Compound (III-6).

One drop of piperidine was added to a solution of compound 61 (25 mg, 0.016 mmol) in DMF (1 mL) at RT. After the reaction mixture was stirred at RT for 1 h, the reaction was quenched by addition of a mixture of acetonitrile and water containing 0.1% TFA. The crude product was purified by prep HPLC to afford 20 mg of compound (III-6) as a white solid. MS: (+) m/z 668.0 (M/2+1). Compound (III-6) has a hydroxylamine group, which can be use for conjugation via oxime formation, for instance with the ketone group of a p-acetylphenyalanine residue that has been introduced into a protein, as discussed above.

A conjugate of compound (III-6) and an anti-mesothelin antibody modified to contain a p-acetylphenylalanine residue exhibited an $EC_{50}$ of 0.14 against N87 gastric cancer cells, using a $^3H$ thymidine incorporation assay.

In one embodiment, this invention provides a conjugate of compound (III-6) and an anti-mesothelin antibody modified to contain a ketone group. Preferably, the modification is by the incorporation of a p-acetylphenylalanine residue into the antibody polypeptide chain. Also preferably, the antibody so modified is 6A4.

Example 9

Intermediate Compound 69

Figure 10:
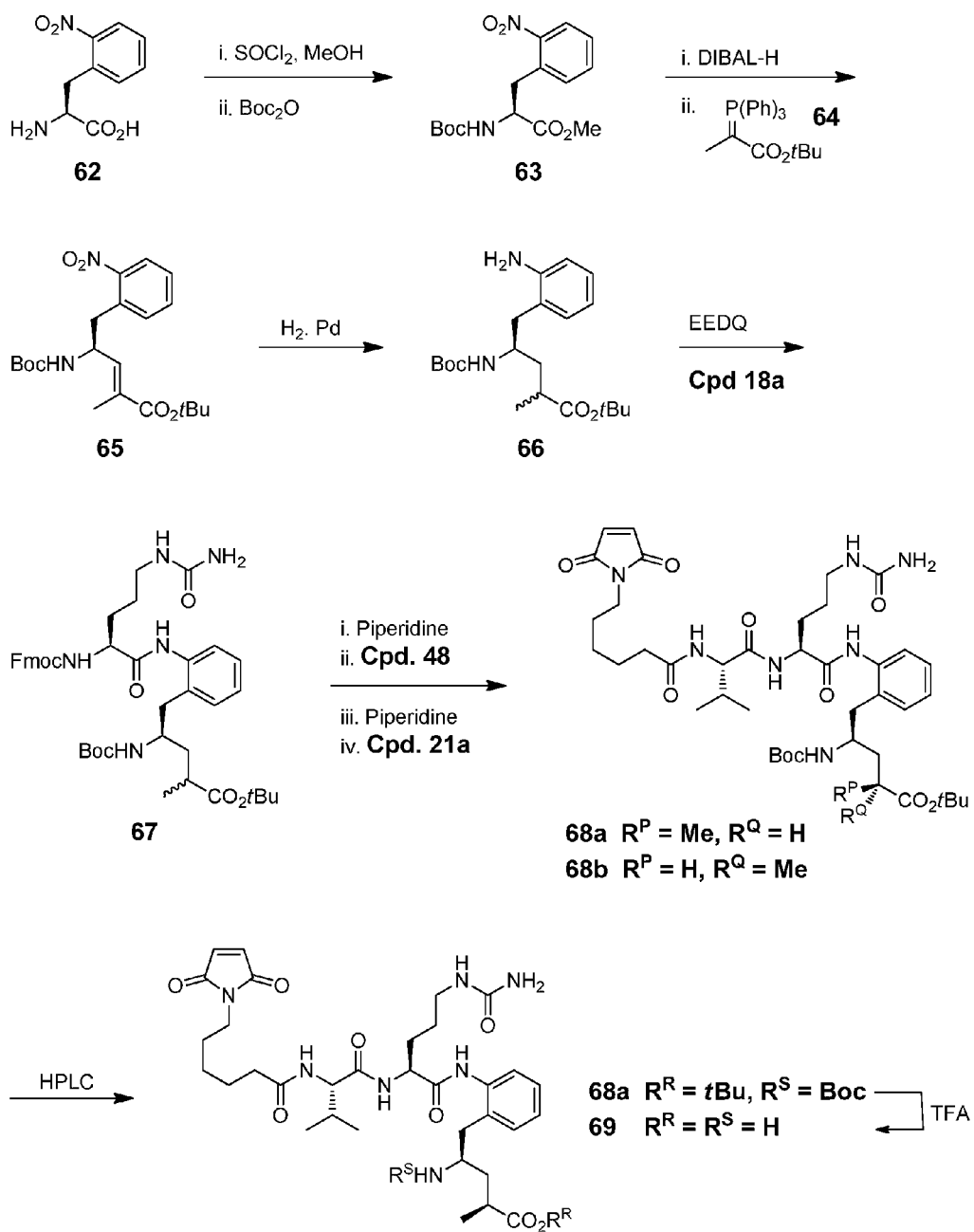
FIGS. 10 and 11 show schemes for the synthesis of intermediates useful for making compounds of this invention.

FIG. 10 shows a scheme for the synthesis of compound 69, which can be used as an intermediate for the synthesis of compounds of this invention.

Compound 63.

Compound 62 (Chem-Impex, 5 g, 23.8 mmol) was added into a solution of $SOCl_2$ (3.47 mL, 47.6 mmol) in 20 mL MeOH at 5° C. After allowing reaction to proceed overnight, the reaction mixture was heated for half an hour at 45° C. The volatile materials were evaporated and the residue was dissolved in 20 mL DCM. $Boc_2O$ (7.8 g, 35.7 mmol) was added. $Et_3N$ was used to adjust the pH of the solution to 9 (tested with moistened pH paper). After a few hours the reaction mixture was taken up in EtOAc. The EtOAc solution was washed with 10% citric acid solution, sat. aq. $NaHCO_3$ solution and brine. The organic phase was dried, separated and evaporated down. The final residue from the evaporation of the dried organic phase was passed through a column to give compound 63 (5 g, 65% yield, [M+1-Boc]$^+$, calculated 225.1. found 225.2).

Compound 65.

To a 20 mL DCM solution of compound 63 (2 g, 6.2 mmol) was added DIBAL-H (12.4 mL, 12.4 mmol, 1M in DCM) at −78° C. After half an hour, MeOH was used to quench the reaction. HCl was used to adjust the pH of the solution to around 2. The mixture was taken up in EtOAc, which was washed with 10% citric acid, brine, dried, separated and evaporated. The residue was dissolved in 30 mL of DCM. Compound 64 (2.4 g, 6.2 mmol, U.S. Pat. No. 4,894,386) was added at 0° C. The mixture was evaporated after 1 h at RT, the residue was passed through a column to give compound 65 (2 g, 79% yield, [M+1-Boc]$^+$, calculated 307.2. found 307.1).

Compound 66.

Compound 65 (600 mg, 1.48 mmol) was dissolved in 75 mL EtOAc at RT. The solution was transferred a flask filled with $N_2$ and Pd/C (600 mg, 10%). The flask was evacuated and refilled with $H_2$; the cycle was repeated three times. After 1 h the solution was filtered and evaporated to give compound 66 (560 mg, 100% yield, [M+1]$^+$, calculated 379.3. found 379.3) as a mixture of epimers. This mixture was not separated until later.

Compound 67.

Compound 66 (1.30 g, 3.43 mmol), Fmoc-protected citrulline 18a (1.6 g, 4.12 mmol) and 2-ethoxy-1-ethoxycarbonyl-1,2-dihydroquinoline (EEDQ, 1.06 g, 4.3 mmol) were dissolved in a mixture of DCM and MeOH (22 mL, 10:1). After allowing reaction to proceed overnight, the mixture was evaporated and the residue was passed through a column (MeOH:DCM, 0-5% gradient) to give compound 67 ([M+1]+, 7 calculated 758.4. found 758.4) as a mixture of epimers (=4:1 from HPLC analysis). It was used for next step without further purification.

Compound 68a.

The mixture of compound 67 from the above reaction was dissolved in 10 mL of DMF (with 5% piperidine) at RT. After 30 min, the mixture was evaporated and dried with a high vacuum pump overnight. The residue was mixed with compound 48 (1.5 g, 3.45 mmol) in 5 mL DMF. $Et_3N$ was used to adjust the pH of the solution to 12. After 1 h the reaction mixture was taken up in EtOAc, which was washed with 10% citric acid, sat. aq. $NaHCO_3$ solution and brine. The organic phase was dried, filtered and evaporated to dryness. The residue was deprotected with 5% piperidine in DMF in the same way as the deprotection of compound 67. The amine obtained in this step and compound 21a (1 g, 3.27 mmol) were mixed in 10 mL of DMF. $Et_3N$ was used to adjust the pH of the solution to 12 at RT. After allowing the reaction to proceed overnight, the mixture was taken up in EtOAc, which was washed with 10% citric acid, sat. aq. $NaHCO_3$ and brine. The organic phase was dried, filtered and evaporated to give a residue. The residue was passed through a regular silica column to give a mixture of compounds 68a and 68b (1 g, 35% yield from compound 66, [M+1]$^+$, calculated 828.5. found 828.5). After separation on a preparative HPLC column, 600 mg of the major epimer was obtained (structure tentatively assigned as compound 68a, with compound 68b assigned as the minor one).

Compound 69.

Compound 68a (600 mg, 0.72 mmol) was dissolved in a 5 mL mixture of DCM and TFA (1:1). After 2 h, the reaction mixture was evaporated to give compound 69 (quantitative yield, [M+1], calculated 672.4. found 672.4).

Example 10

Intermediate Compound 75

Figure 11:
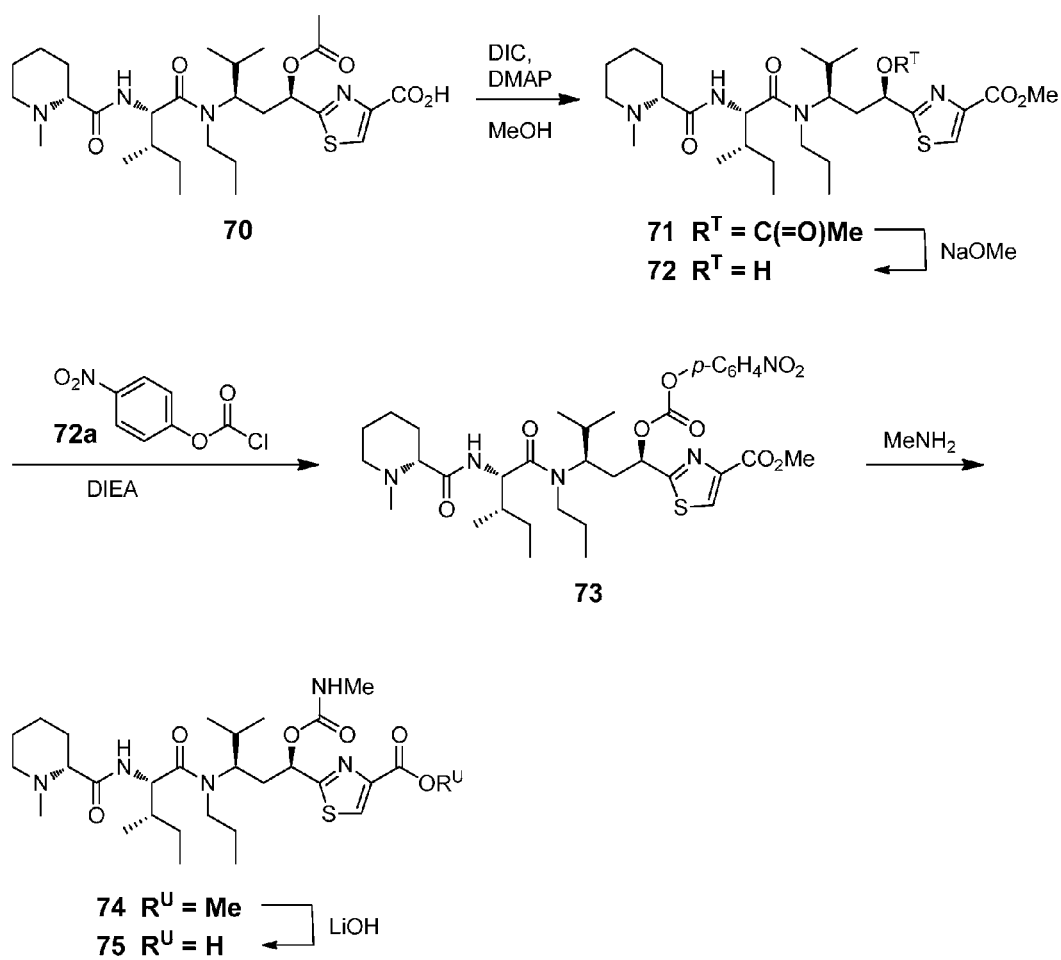

FIG. 11 shows a scheme for the synthesis of intermediate compound 75, which can be used for the synthesis of compounds of this invention.

Compound 71.

Compound 70 (Cheng et al. 2011, 25 mg, 0.044 mmol), N,N'-diisopropylcarbodiimide (DIC, 0.014 mL, 0.088 mmol), 4-(dimethylamino)pyridine (DMAP, 10.78 mg, 0.088 mmol) and MeOH (0.036 mL, 0.882 mmol) were mixed at RT. After an hour, the reaction mixture was evaporated and passed through a column to give compound 71 (10 mg, 39% yield, M+1, 581.4).

Compound 72.

Compound 71 (122 mg, 0.210 mmol, from another synthetic batch) was dissolved in MeOH (2 mL) at 5° C. NaOMe (0.441 mL, 0.221 mmol) was added. After 0.5 h the mixture was neutralized with HCl (4M in dioxane) and evaporated to give compound 72 (m+1, 539.4), which was used for next step without further purification.

Compound 73.

Compound 72 (60 mg, 0.111 mmol) was dissolved in DCM (1.5 mL) at 5° C. Pyridine (0.045 mL, 0.557 mmol). 4-Nitrophenylcarbonochloridate 72a (67.3 mg, 0.334 mmol, Aldrich) in 0.5 mL DCM was added slowly. After allowing reaction to proceed overnight, the mixture was evaporated and purified by column chromatography to give compound 73 (42 mg, 0.060 mmol, 53.6% yield) (m+1, 704.4).

Compound 74.

Compound 73 (42 mg, 0.060 mmol) was dissolved in DCM (1 mL) at 5° C. Methylamine (1.853 mg, 0.060 mmol) was added. After 0.5 h the mixture was evaporated and the residue was passed through a chromatographic column (MeOH:DCM, 0-15% gradient, product eluting out at 7-10%) to give compound 74 (35 mg, 0.059 mmol, 98% yield) (m+1, 596.4).

Compound 75.

Compound 74 (93 mg, 0.156 mmol) was dissolved in THF (1 mL) at 5° C. LiOH (7.47 mg, 0.94 mmol) in 0.34 mL water was added. After the reaction finished, the reaction mixture was neutralized with HCl (4M in dioxane) and dried on high vacuum to give compound 75 (m+1, 582.3), which was used for next step without further purification.

Example 11

Compounds (III-7) and (III-8)

Figure 12:
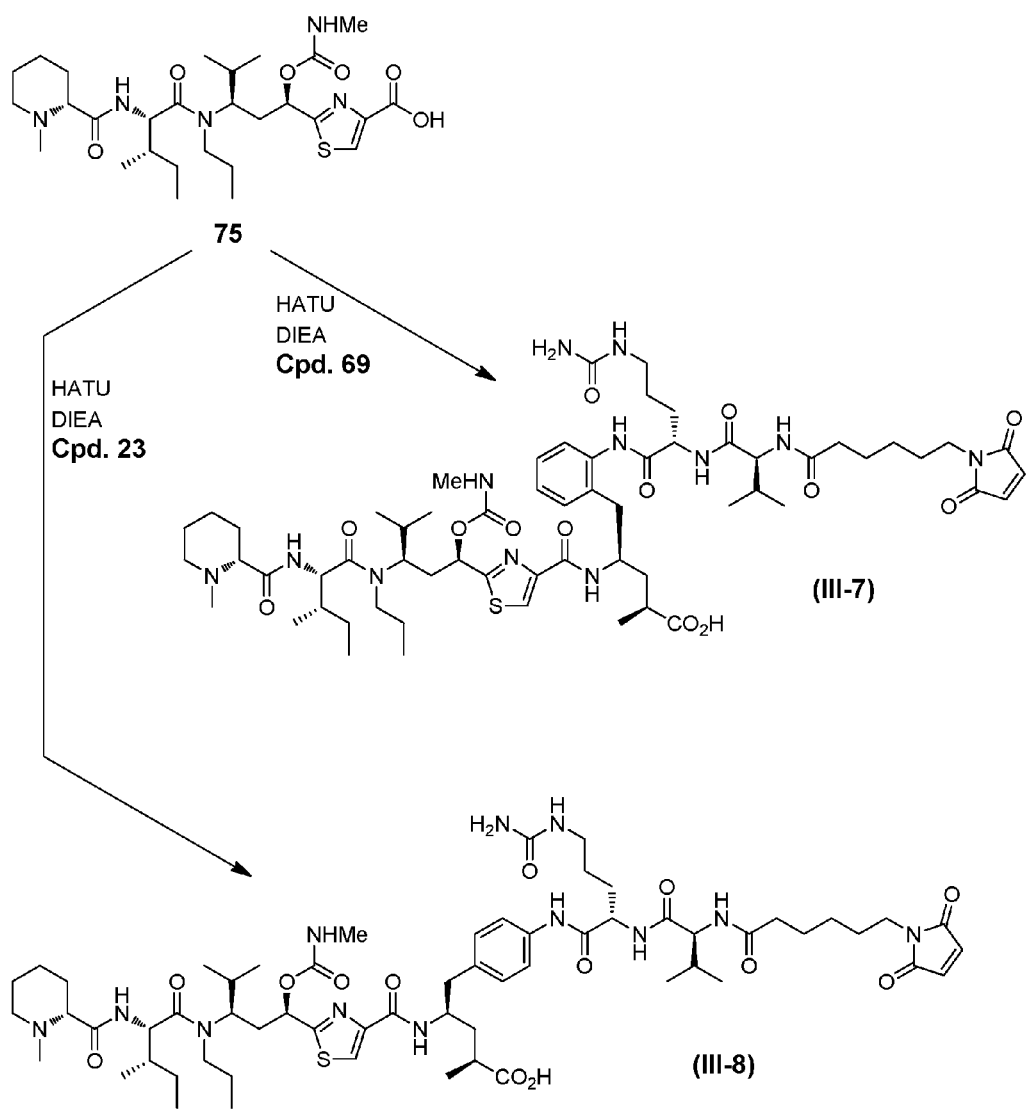
FIG. 12 shows schemes for synthesis of additional compounds of this invention.

FIG. 12 shows schemes for the synthesis of compounds (III-7) and (III-8).

Compound (III-7).

Compound 75 (11 mg, 0.019 mmol) was activated in DMF (0.5 mL) with HATU (6.83 mg, 0.018 mmol) and DIEA (14.86 µl, 0.085 mmol). Compound 69 (15.24 mg, 0.023 mmol) was then added. After 10 min the reaction mixture was taken up in DMSO and purified by preparative chromatography to give compound (III-7) (12 mg, 9.71 µmol, 51.4% yield) (m+1, 1235.7).

Compound (III-8).

Compound 75 (10 mg, 0.017 mmol) was activated in DMF (0.5 mL) with HATU (6.21 mg, 0.016 mmol) and DIEA (0.014 mL, 0.077 mmol). Compound 23 (13.86 mg, 0.021 mmol) was then added. After 10 min the reaction mixture was taken up in DMSO and purified by preparative chromatography to give compound (III-8) (13 mg, 10.52 µmol, 61.2% yield) (m+1, 1235.7).

Example 12

Compounds (I-8) and (I-9)

In principle, compounds (I-8) and (I-9) can be obtained by treatment of compounds (III-7) and (III-8), respectively, with the protease cathepsin B, for which the dipeptide Val-Cit is a substrate motif. Compound (III-7), with its ortho-amino group, may be subject to more steric hindrance against cleavage.

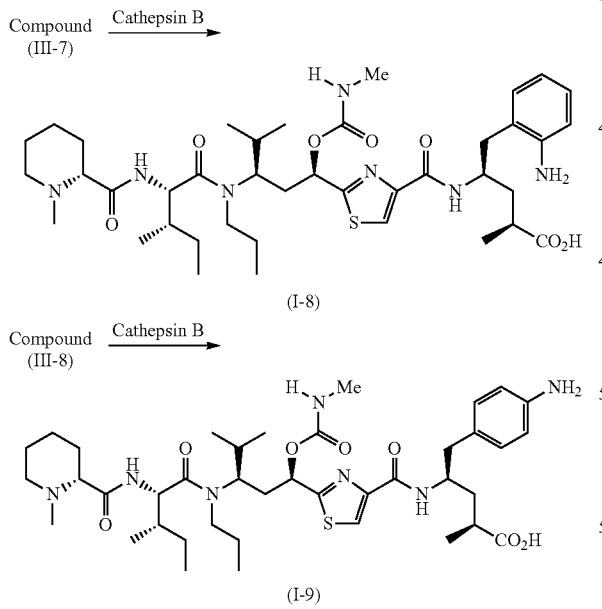

Example 13

Biological Activity of Compounds

Figure 13A:
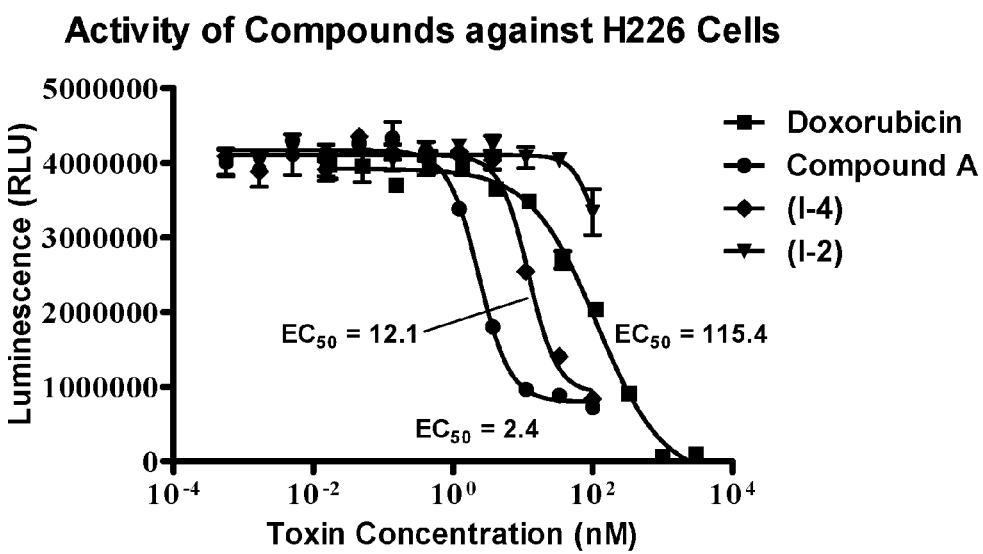
FIGS. 13a-13d show the biological activity of some compounds of this invention.
Figure 13B:
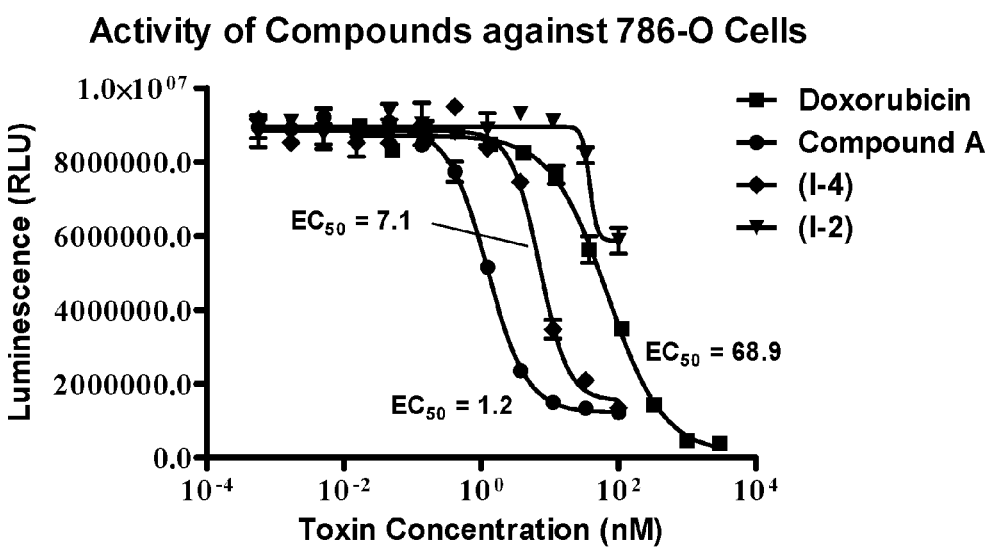

FIGS. 13a and 13b show the biological activity of compounds (I-4) and (I-2) of this invention against H226 lung cancer and 786-O renal cancer cells, respectively, using an ATP luminescence assay. As controls, doxorubicin and the tubulysin analog Compound A, which contains an acetate group instead of a carbamate group at the Tuv subunit, were used. Compound A can be prepared according to the teachings of Cheng et al. 2011.

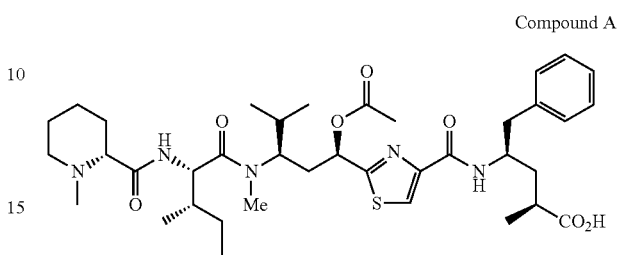

Compound A

Against H226 cells, the $EC_{50}$ values were: doxorubicin, 115.4 nM; Compound A, 2.4 nM; and compound (I-4), 12.1 nM. Against 786-0 cells, the $EC_{50}$ values were: doxorubicin, 68.9 nM; Compound A, 1.2 nM, and compound (I-4), 7.1 nM.

Figure 13C:
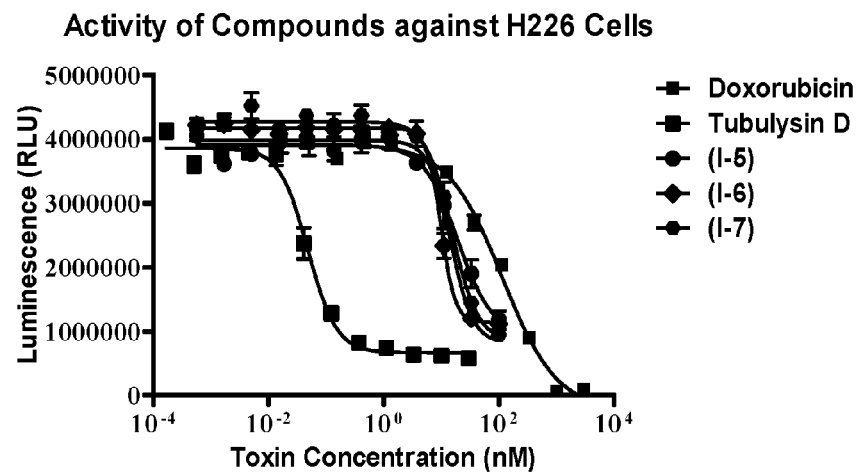
Figure 13D:
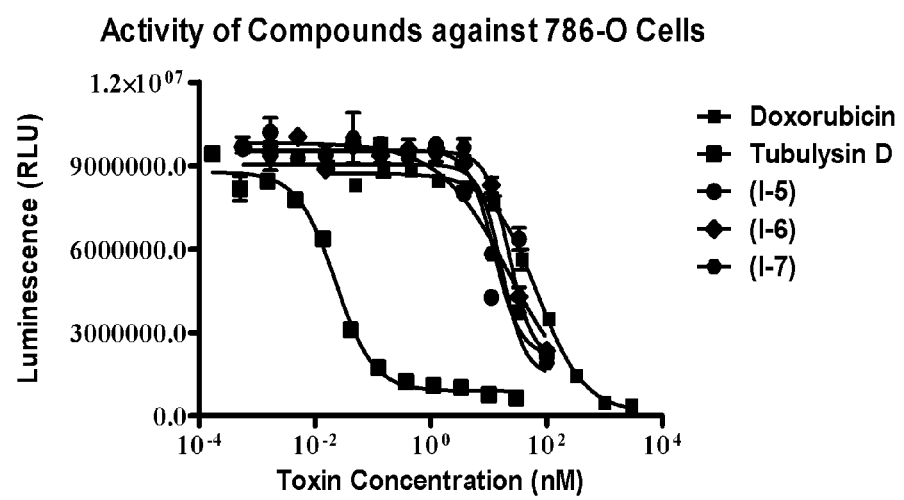

FIGS. 13c and 13d present the similar type of data for compounds (I-5), (I-6), and (I-7). The comparison compounds were doxorubicin and tubulysin D. The $EC_{50}$ values against H226 cells were: doxorubicin, 115.4 nM; tubulysin D, 0.05 nM; compound (I-5), 19.5 nM; compound (I-6), 9.9 nM; and compound (I-7), 15.4 nM. Against 786-0 cells, the $EC_{50}$ values were: doxorubicin, 68.9 nM; tubulysin D, 0.02 nM; compound (I-5), 22.9 nM; compound (I-6), 22.8 nM; and compound (I-7), 12.5 nM.

Tumor cell lines were obtained from the American Type Culture Collection (ATCC), P.O. Box 1549, Manassas, Va. 20108, USA, and cultured according to ATCC instructions. Cells were seeded at $1.0 \times 10^3$ cells/well in 96-well plates for 3 h for the ATP assays. 1:3 serial dilutions of the compounds were added to the wells. Plates were allowed to incubate for 24 to 72 h. ATP levels in the ATP plates were measured using the CELLTITER-GLO® Luminescent Cell Viability kit following the manufacturer's manual and read on a GLO-MAX® 20/20 luminometer (both from Promega, Madison, Wis., USA). The $EC_{50}$ values—the concentration at which an agent inhibits or reduces cell proliferation by 50%—were determined using PRISM™ software, version 4.0 (Graph-Pad Software, La Jolla, Calif., USA).

Example 14

In Vitro Activity of a Conjugate

Figure 14:
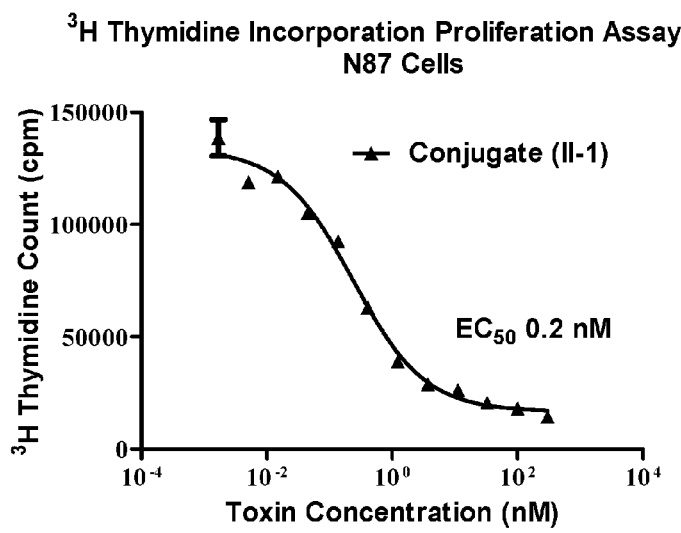
FIG. 14 shows the in vitro activity of a conjugate of this invention.

FIG. 14 shows the in vitro activity of conjugate (II-1), against N87 gastric cancer cells (American Type Culture Collection (ATCC), P.O. Box 1549, Manassas, Va. 20108, USA).

Cells were seeded at $1.0 \times 10^4$ cells/well in 96-well plates for 3 h for $^3H$ thymidine assays, respectively. Serial dilutions (1:3) of conjugate (II-1) were added to the wells. Plates were allowed to incubate for 120 h. The plates were pulsed with 1.0 µCi of $^3H$-thymidine per well for the last 24 h of the total incubation period, harvested, and read on a Top Count Scintillation Counter (Packard Instruments, Meriden, Conn.). The $EC_{50}$ value—the concentration at which an agent inhibits or reduces cell proliferation by 50% of the maximum inhibition—was determined using PRISM™ software, version 4.0 (GraphPad Software, La Jolla, Calif., USA) to be 0.2 nM A comparison of the $EC_{50}$ values from FIGS. 13a-13d and FIG. 14 illustrates two points. First is the potency enhancement associated with the targeted delivery of a cytotoxin via a conjugate and then the active internalization mechanism triggered by binding of the antibody component of the conjugate to its antigen (Schrama et al. 2006). Second, the unconjugated toxins are relatively polar compounds and, in the absence of an active internalization mechanism, have difficulty diffusing across a cell membrane, thus resulting in higher (lower potency) measured $EC_{50}$ values.

Example 15

In Vivo Activity of a Conjugate

In this example, the in vivo activity of conjugate (II-1) was compared against that of Conjugate B (Cheng et al. 2011), which is structurally identical to conjugate (II-1), except that it has an acetate in the Tuv subunit instead of a carbamate:

$V_H$ CDR1, CDR2, and CDR3 and $V_K$ CDR1, CDR2, and CDR3 sequences for antibody 6A4 are given in SEQ ID NO:1, SEQ ID NO:2, SEQ ID NO:3, SEQ ID NO:4, SEQ ID NO:5, and SEQ ID NO:6, respectively. The variable region $V_H$ and $V_K$ sequences of antibody 6A4 are provided in SEQ ID NO:7 and SEQ ID NO:8, respectively.

The preparation and characterization of human monoclonal antibody 1F4 is described in Coccia et al. 2010, the disclosure of which is incorporated herein by reference. The $V_H$ CDR1, CDR2, and CDR3 and $V_K$ CDR1, CDR2, and CDR3 sequences for antibody 1F4 are given in SEQ ID NO:9, SEQ ID NO: 10, SEQ ID NO: 11, SEQ ID NO: 12, SEQ ID NO:13, and SEQ ID NO:14, respectively. The variable region $V_H$ and $V_K$ sequences of antibody 1F4 are provided in SEQ ID NO:15 and SEQ ID NO:16, respectively.

Figure 17A:
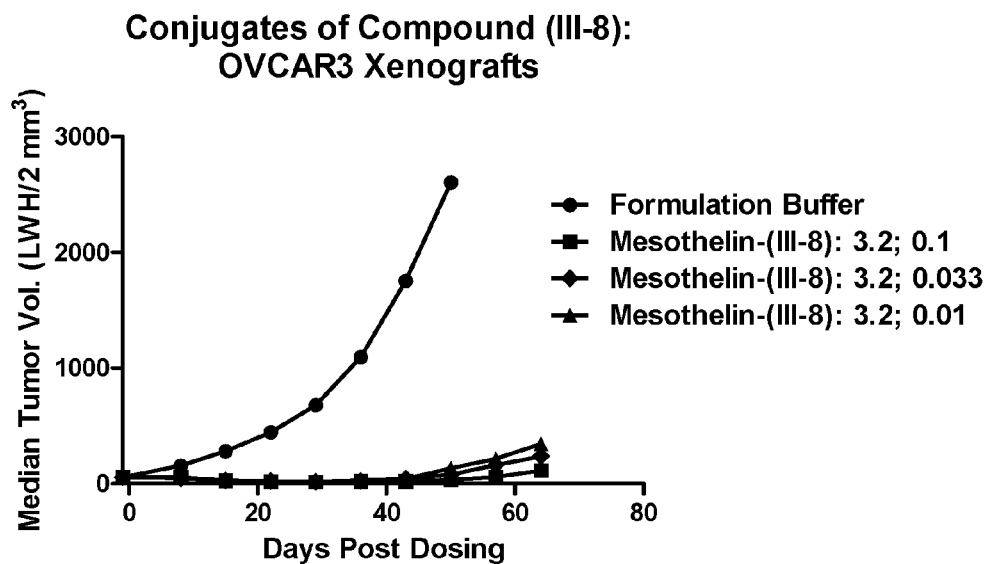
Figure 17B:
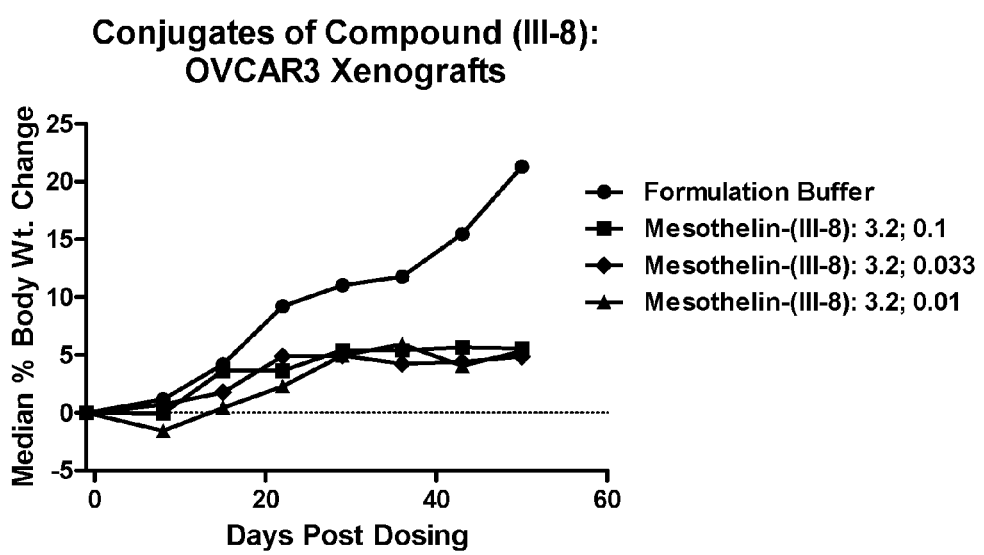
Figure 18A:
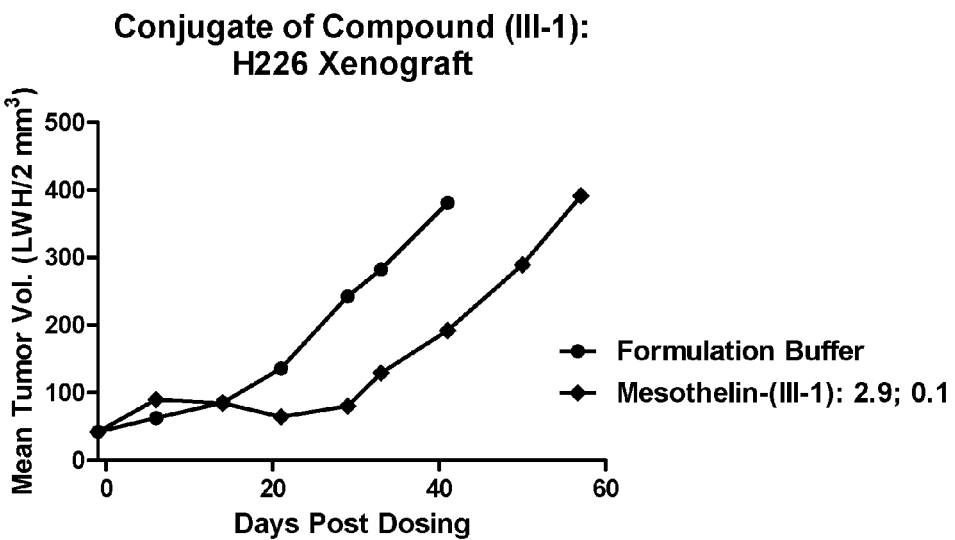
Figure 18B:
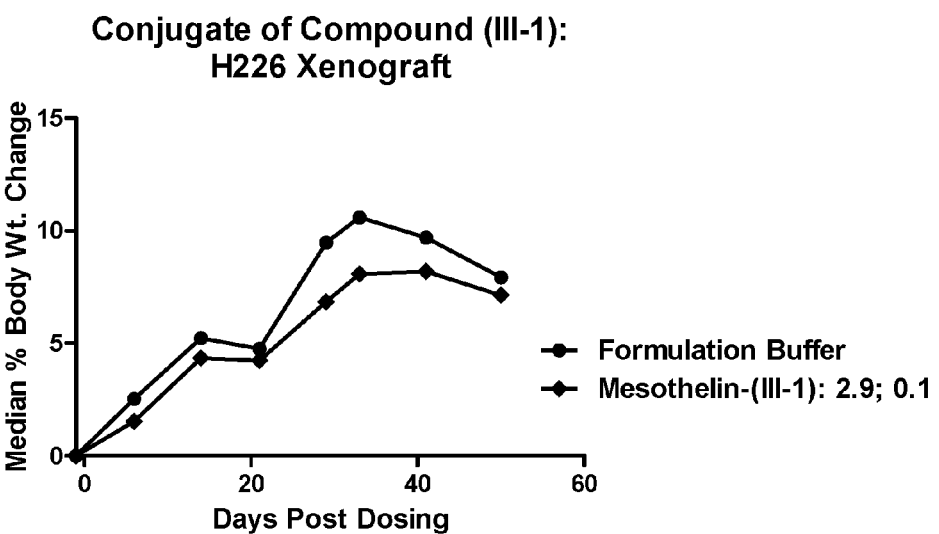

FIGS. 17a and 17b present the results for a similar experiment, but with conjugates of compound (III-8) and anti-mesothelin antibody 6A4. In each instance, a single dose was administered intraperitoneally.

Conjugate B

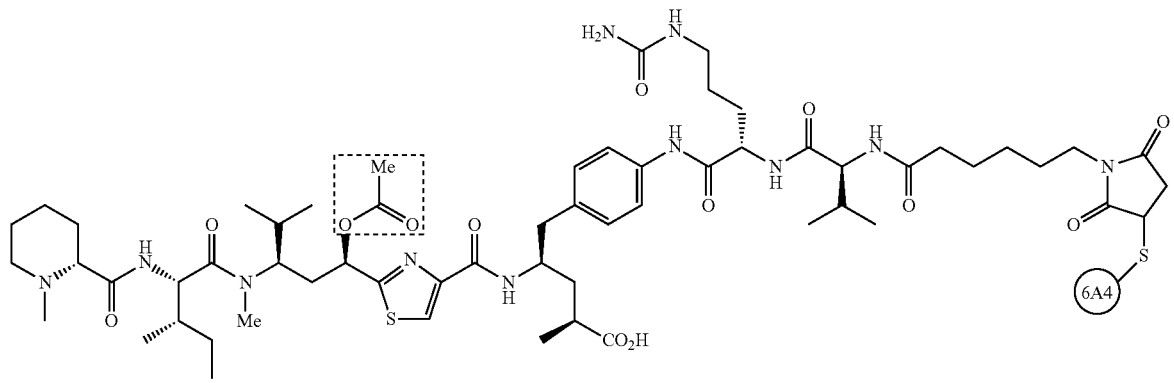

Figure 15:
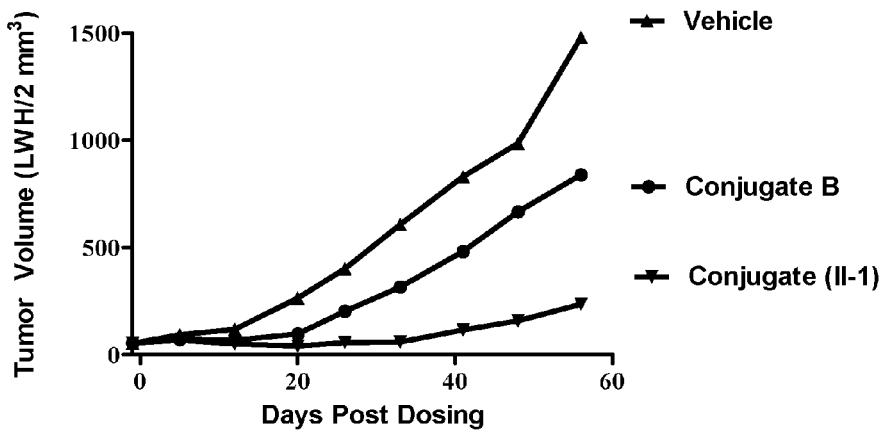
FIG. 15 shows the in vivo activity of a conjugate of this invention.

Five million OVCAR3 ovarian cancer cells, resuspended in 0.1 mL phosphate buffered saline ("PBS") plus 0.1 mL matrigel, were implanted subcutaneously at the flank region of SCID mice. Tumor measurements started 28 days later, and mice were randomized into groups of 7 mice each with average tumor sizes of 60 mm³ estimated by LWH/2 of tumors. At 29 days post tumor implantation, mice were dosed intraperitoneally singly with testing compounds. FIG. 15 shows that, against OVCAR3 xenografts, conjugate (II-1) suppressed tumor growth more effectively than conjugate B. The differential is especially notable after 20 days.

FIGS. 16a, 16b, 17a, 17b, 18a, 18b, 19a, 19b, and 20 present additional in vivo efficacy data for conjugates of this invention, generated per the protocol described above, mutatis mutandis.

Figure 16A:
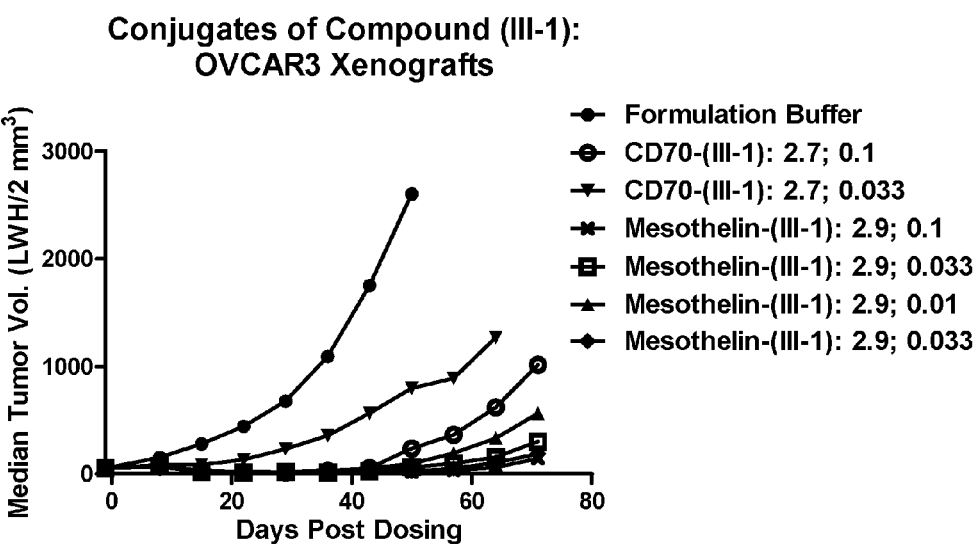
Figure 16B:
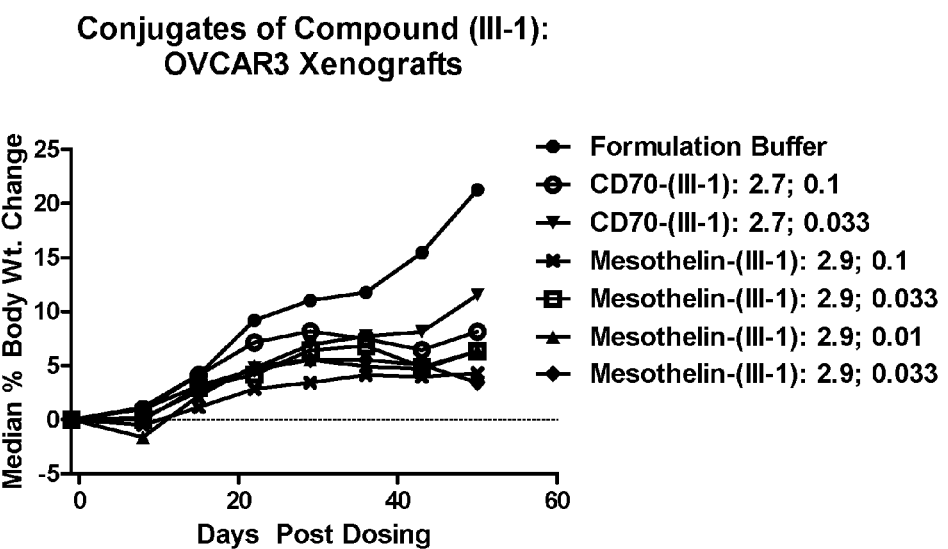

FIG. 16a shows the data for OVCAR3 (ovarian cancer) tumor volume versus time for a series of conjugates of compound (III-1) with anti-CD70 antibody 1F4 or anti-mesothelin antibody 6A4. The legend provides, in order, the DAR (e.g., "2.7") and dosage in mol/kg (e.g., "0.1"). In each instance the mode of administration was intraperitoneal, in a single dose (SD), except for last data set (♦), for which the conjugate was administered Q7Dx3. FIG. 16b shows the body weight change for the same experiment.

The preparation and characterization of human monoclonal antibody 6A4 is described in Terrett et al. 2012, the disclosure of which is incorporated herein by reference. The The efficacy of a conjugate of compound (III-1) and anti-mesothelin antibody 6A4 against H226 (lung cancer) tumors is presented in FIGS. 18a and 18b, with DAR and dosage information found again in the legends. In each instance the conjugate was administered intraperitoneally in a single dose.

Figure 19A:
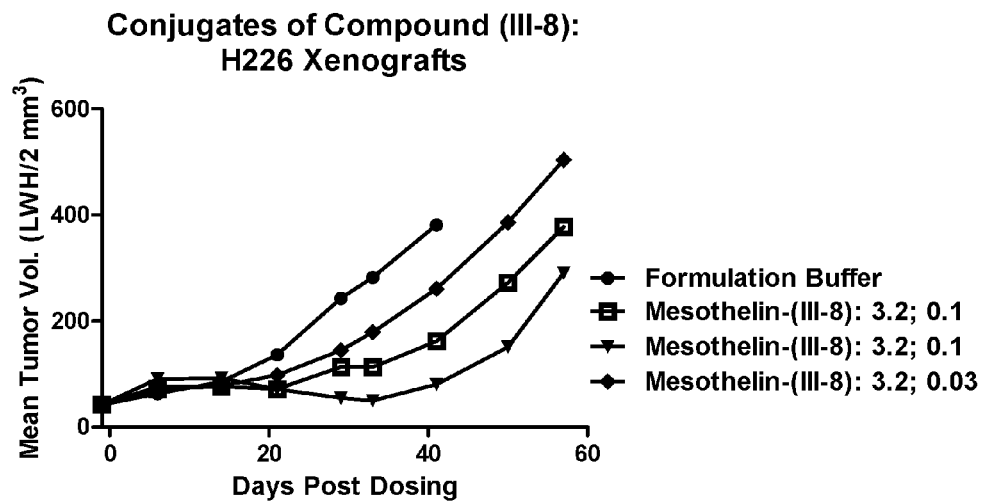
Figure 19B:
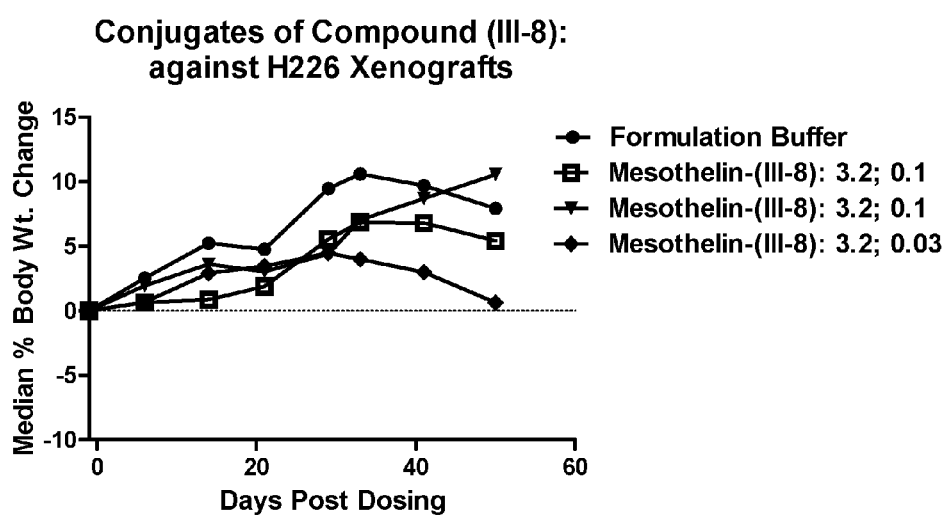

FIGS. 19a and 19b present H226 data for a conjugate of compound (III-8) and anti-mesothelin antibody 6A4. In the first data set (●) the administration was a single dose, while for the last two data sets (▼ and ♦) the administration regimen was Q7Dx3.

Figure 20:
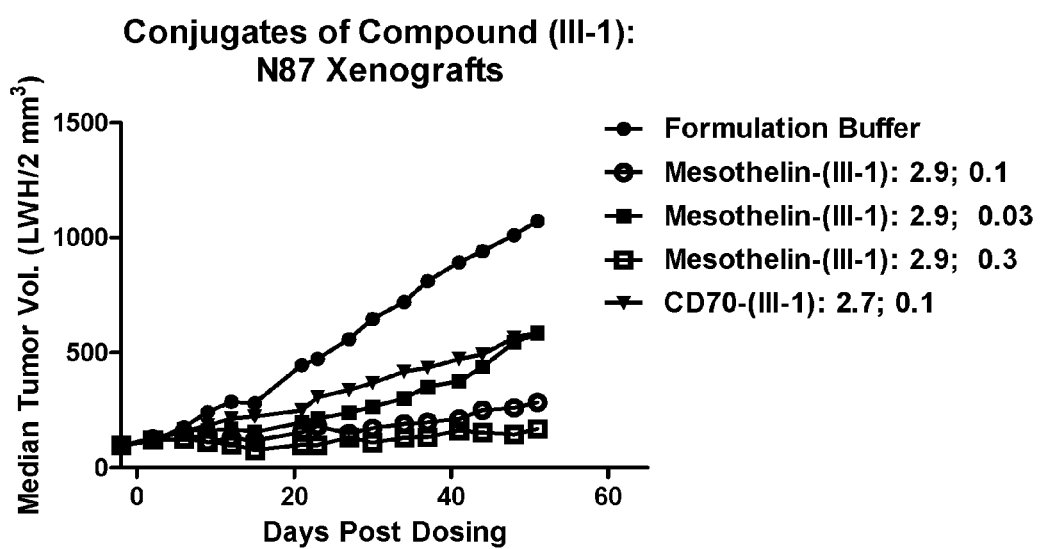

FIG. 20 shows the efficacy data for conjugates of compound (III-1) with anti-mesothelin antibody 6A4 or anti-CD70 antibody 1F4 against N87 gastric cancer tumors.

Antibodies, especially when used in conjugates, may have either a natural constant region or an engineered (modified) one, designed to reduce or eliminate effector functions such as ADCC. Examples of such modified antibody constant regions are provided by the polypeptides of SEQ ID NO:25 and SEQ ID NO:26. SEQ ID NO:25 is a constant region of the IgG4 isotype modified with certain amino acid substitutions. SEQ ID NO:26 is a hybrid IgG1/IgG4 constant region. In both SEQ ID NO:25 and SEQ ID NO:26 the presence of the C-terminal lysine is optional.

Example 16

Stability Studies

In this example, the mouse serum stability of Conjugate (II-1) and Conjugate B, with their respective carbamate and acetate groups, were compared.

The conjugate was injected into mice at a dose of 0.1 μmol/kg. In the case of conjugate (II-1) the administration concentration was 3.4 mg/mL and the conjugate had a substitution ratio (SR) of 4.2. In the case of conjugate B the administration concentration was 1.2 mg/mL and the SR was 2.3. Approximately 100 uL of serum from each of 3 animals at each time point was taken for analysis.

Serum samples from the different animals were pooled, giving 200-300 uL at each time point. The pooled volume was centrifuged to remove solids and the supernatant was used for analysis. The conjugate was isolated from serum by immuno-affinity capture using an anti-idiotypic monoclonal antibody coupled to SEPHAROSE™ beads. After capture, the conjugate was eluted by exposure to low pH followed by neutralization with Tris base. Cytotoxin present on the conjugate was released by addition of activated cathepsin B to cleave the Cit-Val peptide linker. Cathepsin B digestion was done at 37° C. for 3 h, followed by addition of 1 volume of cold methanol. The solvent-extracted cytotoxin was analyzed by LC-MS using an ESI-TOF MS in-line to a UPLC with reverse phase chromatography (Acquity HSS T3 2.1× 50 mm).

For conjugate (II-1), the presence of the hydroxyl compound from hydrolysis of the carbamate group was not detected at any time, through time points up to 240 h. Only the carbamate compound was detected.

Conversely, for conjugate B, the hydrolysis product was detectable after 6 hours and about 50 percent hydrolysis had occurred by 72 h. Table 2 below shows the relative amounts of the acetate and hydroxyl compounds, based on mass spectrum intensities for the respective doubly charged ions (M[H$^{2+}$]372.2 Da and 351.2 Da):

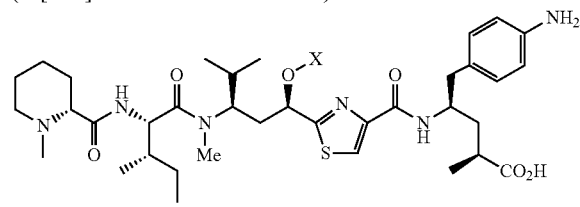

Carbamate X = C(=O)NHMe
Acetate: X = C(=O)Me
Hydroxyl: X = H

TABLE 2

| Time (h) | Relative Peak Intensity | | Hydroxyl Ion |
|---|---|---|---|
| | Acetate Ion | Hydroxyl Ion | (% of total) |
| 0.25 | 360,587 | — | 0 |
| 2 | 649,982 | — | 0 |
| 6 | 165,680 | 11,779 | 7 |
| 24 | 77,110 | 14,619 | 16 |
| 48 | 26,760 | 16,312 | 38 |
| 72 | 18,243 | 17,124 | 48 |
| 168 | 7,978 | 18,330 | 70 |
| 240 | 4,268 | 15,654 | 79 |

These results show that while replacement of the acetate group in the Tuv subunit 5 leads to a much more stable compound, which however still retains substantial biological activity.

Example 17

Compounds 72a, 72b, and 72c

This example describes the preparation and properties of compounds of this invention having structural variations at the carbamate group. Reference is made to FIG. 21 for the synthetic scheme.

Compound 70a.

Ammonia in MeOH (2M, 0.089 mL, 0.178 mmol) was added to compound 7 (0.1 g, 0.148 mmol) in MeOH (2 mL). After the reaction mixture was stirred at RT for 20 min, LCMS showed the reaction went to completion. The solvent was evaporated. The crude product was purified by flash chromatography eluting from silica gel with a gradient of 0-15% MeOH in DCM to afford 55 mg of compound 70a as a white solid. MS: (+) m/z 554.3 (M+1).

Compound 71a

LiOH (4.41 mg, 0.184 mmol) in water (0.5 mL) was added to a solution of compound 70a (51 mg, 0.092 mmol) in THF (1 mL) at RT. After the reaction mixture was stirred at RT for 2 h, LCMS showed the reaction had gone to completion. The solvent was evaporated. The crude product was purified by flash chromatography eluting from silica gel with a gradient of 0-30% MeOH in DCM to afford 47 mg of compound 71a as a white solid. MS: (+) m/z 540.3 (M+1).

Compound 72a.

DIEA (6.45 μL, 0.037 mmol) was added to a solution of compound 71a (20 mg, 0.037 mmol) and HATU (14.09 mg, 0.037 mmol) in DMF (0.5 mL). The pH of the reaction mixture was adjusted to 8-9. After the reaction mixture was stirred at RT for 20 min, compound 23 (24.9 mg, 0.037 mmol) in DMF (1 mL) and DIEA (6.45 μL, 0.037 mmol) were added. The pH of the reaction solution was adjusted to 8-9. After the reaction mixture was stirred at RT for another 20 min, LCMS showed the reaction went to completion. The reaction was quenched by the addition of 10 mL 1:1 (v/v) mixture of water containing 0.1% TFA and acetonitrile containing 0.1% TFA. The crude product was purified by preparative HPLC to afford 35.2 mg of compound 72a as a white solid. MS: (+) m/z 1193.6 (M+1). Compound 72a is also referred to herein above as compound (III-9).

A conjugate of compound 72a and anti-CD70 antibody 1F4 had an EC$_{50}$ of 0.19 nM against 786-0 renal cancer cells. A conjugate of compound 72a and anti-mesothelin antibody 6A4 had an EC$_{50}$ of 0.16 nM against N87 gastric cancer cells. In both instances, an $^3$H-thymidine incorporation assay was used.

Compound 70b.

A solution of compound 7 (0.1 g, 0.148 mmol) and aniline (0.041 mL, 0.444 mmol) in DMF (1.8 mL) was heated at 50° C. overnight. The solvent was evaporated. The crude product was purified by flash chromatography eluting from silica gel with a gradient of 0-15% MeOH in DCM to afford 58 mg of compound 5 as a white solid. MS: (+) m/z 630.4 (M+1).

Compound 71b.

LiOH (4.03 mg, 0.168 mmol) in water (0.5 mL) was added to a solution of compound 70b (53 mg, 0.084 mmol) in THF (1 mL) at RT. After the reaction mixture was stirred at RT for 2 h, LCMS showed the reaction went to completion. The solvent was evaporated. The crude product was purified by flash chromatography eluting from silica gel with a gradient of 0-30% MeOH in DCM to afford 43 mg of compound 71b as a white solid. MS: (+) m/z 616.3 (M+1).

Compound 72b.

DIEA (5.66 µL, 0.032 mmol) was added to a solution of compound 71b (20 mg, 0.032 mmol) and HATU (12.35 mg, 0.032 mmol) in DMF (0.5 mL). The pH of the reaction mixture was adjusted to 8-9. After the reaction mixture was stirred at RT for 20 min, compound 23 (21.82 mg, 0.032 mmol) in DMF (1 mL) and DIEA (5.66 µL, 0.032 mmol) were added. The pH of the reaction solution was adjusted to 8-9. After the reaction mixture was stirred at RT for another 20 min, LCMS showed the reaction went to completion. The reaction was quenched by the addition of 10 mL 1:1 (v/v) mixture of water containing 0.1% TFA and acetonitrile containing 0.1% TFA. The crude product was purified by preparative HPLC to afford 35 mg of compound 72b as a white solid. MS: (+) m/z 1269.7 (M+1). Compound 72b is also referred to hereinabove as compound (III-10).

A conjugate of compound 72b and anti-CD70 antibody 1F4 had an $EC_{50}$ of 0.58 nM against 786-O renal cancer cells. A conjugate of compound 72b and anti-mesothelin antibody 6A4 had an $EC_{50}$ of 0.47 against N87 gastric cancer cells. In both instances a $^3$H thymidine incorporation assay was used.

Compound 70c.

Dimethylamine in DMF (1 mL, 0.148 mmol) was added dropwise to a solution of compound 7 (0.1 g, 0.148 mmol) in DMF (1 mL) at RT, until the reaction went to completion. The solvent was evaporated. The crude product was purified by flash chromatography eluting from silica gel with a gradient of 0-15% MeOH in DCM to afford 56 mg of compound 70c as a white solid. MS: (+) m/z 582.3 (M+1).

Compound 71c.

LiOH (8.23 mg, 0.344 mmol) in water (0.5 mL) was added to a solution of compound 70c (0.1 g, 0.172 mmol) in THF (1 mL) at RT. After the reaction mixture was stirred at RT for 2 h, LCMS showed the reaction went to completion. The solvent was evaporated. The crude product was purified by flash chromatography eluting from silica gel with a gradient of 0-30% MeOH in DCM to afford 50.8 mg of compound 71c as a white solid. MS: (+) m/z 568.3 (M+1).

Compound 72c.

DIEA (6.14 µL, 0.035 mmol) was added to a solution of compound 71c (20 mg, 0.035 mmol) and HATU (13.39 mg, 0.035 mmol) in DMF (0.5 mL). The pH of the reaction mixture was adjusted to 8-9. After the reaction mixture was stirred at RT for 20 min, compound 23 (23.67 mg, 0.035 mmol) in DMF (1 mL) and DIEA (6.14 µL, 0.035 mmol) were added. The pH of the reaction solution was adjusted to 8-9. After the reaction mixture was stirred at RT for another 20 min, LCMS showed the reaction went to completion. The reaction was quenched by the addition of 10 mL 1:1 (v/v) mixture of water containing 0.1% TFA and acetonitrile containing 0.1% TFA. The crude product was purified by preparative HPLC to afford 23.8 mg of compound 72c as a white solid. MS: (+) m/z 1221.6 (M+1). Compound 72c is also referred to hereinabove as compound (III-11).

A conjugate of compound 72c and anti-CD70 antibody 1F4 had an $EC_{50}$ of 0.32 nM against 786-0 renal cancer cells. A conjugate of compound 72c and anti-mesothelin antibody 6A4 had an $EC_{50}$ of 0.34 nM against N87 gastric cancer cells. In both instances a $^3$H thymidine incorporation assay was used.

Example 18

Compounds 75a, 75b, and 75c

This example describes the preparation of the tubulysin analogs of the previous example, but without the linker moieties attached. Reference is made to FIG. 22 for the synthetic scheme.

Compound 73.

LiOH (0.071 g, 2.97 mmol) in water (5 mL) was added to a solution of compound 18 (0.25 g, 0.743 mmol) in THF (5 mL) at RT. After the reaction mixture was stirred at RT for 2 h, the solvent was evaporated. The crude product was purified by flash chromatography eluting from silica gel with a gradient of 0-20% MeOH in DCM to afford 0.22 g of compound 73 as a white solid. MS: (+) m/z 223.3 (M+1-Boc).

Compound 74.

A mixture of compound 73 (0.2 g, 0.620 mmol) and 4N HCl in 1,4-dioxane (4 mL, 0.620 mmol) was stirred at RT for 1 h. The solvent was evaporated. The white solid compound 74 was washed with hexanes twice. MS: (+) m/z 223.3 (M+1).

Compound 75a.

DIEA (3.23 µL, 0.019 mmol) was added to a solution of compound 71a (10 mg, 0.019 mmol) and HATU (7.05 mg, 0.019 mmol) in DMF (0.5 mL), adjusting pH to 8-9. After the reaction mixture was stirred at RT for 20 min, DIEA (3.23 µL, 0.019 mmol) and compound 74 (5.35 mg, 0.024 mmol) in DMF (0.5 mL) were added, adjusting the pH to 8-9. After the reaction mixture was stirred at RT for 1 h, LCMS showed the reaction went to completion. The reaction was quenched by addition of 10 mL of 1:1 (v/v) mixture of acetonitrile and water containing 0.1% TFA. The crude product was purified by preparative HPLC to afford 6.0 mg of compound 75a as a white solid. MS: (+) m/z 744.4 (M+1). Compound 75a is also referred to hereinabove as compound (I-10).

Compound 75a had an $EC_{50}$ of 75.8 nM against N87 gastric cancer cells, using an ATP luminescence assay.

Compound 75b.

DIEA (2.83 µL, 0.016 mmol) was added to a solution of compound 71b (10 mg, 0.016 mmol) and HATU (6.17 mg, 0.016 mmol) in DMF (0.5 mL), adjusting pH to 8-9. After the reaction mixture was stirred at RT for 20 min, DIEA (2.83 µL, 0.016 mmol) and compound 74 (4.69 mg, 0.021 mmol) in DMF (0.5 mL) were added, adjusting the pH to 8-9. After the reaction mixture was stirred at RT for 1 h, LCMS showed the reaction went to completion. The reaction was quenched by addition of 10 mL of 1:1 (v/v) mixture of acetonitrile and water containing 0.1% TFA. The crude product was purified by preparative HPLC to afford 7.6 mg of compound 75b as a white solid. MS: (+) m/z 820.4 (M+1). Compound 75b is also referred to hereinabove as compound (I-11).

Compound 75b had an $EC_{50}$ of 0.39 nM against N87 gastric cancer cells, using an ATP luminescence assay.

Compound 75c.

DIEA (3.07 µL, 0.018 mmol) was added to a solution of compound 71c (10 mg, 0.018 mmol) and HATU (6.70 mg, 0.018 mmol) in DMF (0.5 mL), adjusting the pH to 8-9. After the reaction mixture was stirred at RT for 20 min, DIEA (3.07 µL, 0.018 mmol) and compound 74 (5.09 mg, 0.023 mmol) in DMF (0.5 mL) were added, adjusting the pH to 8-9. After the reaction mixture was stirred at RT for 1 h, LCMS showed the reaction went to completion. The reaction was quenched by addition of 10 mL of 1:1 (v/v) mixture of acetonitrile and water containing 0.1% TFA. The crude product was purified by preparative HPLC to afford 7.6 mg of compound 75c as a white solid. MS: (+) m/z 772.5 (M+1). Compound 75c is also referred to hereinabove as compound (I-12).

Compound 75c had an $EC_{50}$ of 5.4 nM against N87 gastric cancer cells, using an ATP luminescence assay.

Example 19

Compound 80

This example describes the synthesis of a compound 80 suitable for conjugation via "click" chemistry, having a cyclooctyne group that can react with an azide group in a partner molecule. The corresponding synthetic scheme is shown in FIG. 23.

Compound 77.

DCC (22.40 mg, 0.109 mmol) was added to a solution of DBCO-PEG4-Acid 76 (50 mg, 0.090 mmol, purchased from Click Chemistry Tools, Scottsdale, Ariz.) and N-hydroxysuccinimide (NHS, 20.83 mg, 0.181 mmol) in DCM (1 mL) at RT. The reaction mixture was stirred at RT overnight. The solid was filtered off, and the filtrate concentrated to afford compound 77. MS: (+) m/z 650.3 (M+1).

Compound 78.

DIEA was added to a solution of compound 77 (58.8 mg, 0.091 mmol) and compound 21 (57.6 mg, 0.100 mmol) in DMF (1 mL) at RT, adjusting the pH to 8-9. After the reaction mixture was stirred at RT for 1 h, LCMS showed the reaction went to completion. The solvent was evaporated. The crude product was purified by preparative HPLC to afford 20 mg of compound 78 as a white solid. MS: (+) m/z 1113.6 (M+1).

Compound 79.

TFA (0.5 mL, 6.53 mmol) was added to a mixture of compound 78 (17.2 mg, 0.015 mmol) in DCM (1 mL) at RT. After the reaction mixture was stirred at RT for 1 h, LCMS showed the reaction went to completion. The solvent was evaporated to afford compound 79. MS: (+) m/z 1013.5 (M+1).

Compound 80.

DIEA (2.96 µL, 0.017 mmol) was added to a solution of compound 9 (8.55 mg, 0.015 mmol) and HATU (5.87 mg, 0.015 mmol) in DMF (0.4 mL). The pH of the reaction mixture was adjusted to 8-9. After the reaction mixture was stirred at RT for 20 min, compound 79 (15.65 mg, 0.015 mmol) in DMF (1 mL) and DIEA (2.96 µL, 0.017 mmol) were added. The pH of the reaction mixture was adjusted to 8-9. After the reaction mixture was stirred at RT for another 20 min, LCMS showed the reaction went to completion. The solvent was evaporated. The crude product was redissolved in 1 mL of DMSO, and purified by preparative HPLC to afford compound 80 as a white solid. MS: (+) m/z 775.0 (M/2+1). Compound 80 is also referred to hereinabove as compound (III-12).

A conjugate of compound 80 and seven variants of anti-glypican 3 antibody 4A6 modified to have an azide group at various locations exhibited $EC_{50}$'s of 1.4, 0.17, 0.13, 0.22, 0.14, 0.064, and 0.25 nM against N87 gastric cancer cells, using a $^3H$ thymidine incorporation assay.

The preparation and characterization of antibody 4A6 is described in Terrette et al. 2010, the disclosure of which is incorporated herein by reference. The $V_H$ CDR1, CDR2, and CDR3 and $V_K$ CDR1, CDR2, and CDR3 sequences for antibody 4A6 are given in SEQ ID NO:17, SEQ ID NO:18, SEQ ID NO:19, SEQ ID NO:20, SEQ ID NO:21, and SEQ ID NO:22, respectively. The variable region $V_H$ and $V_K$ sequences are provided in SEQ ID NO:23 and SEQ ID NO:24, respectively.

In one embodiment, this invention provides a conjugate of compound 80 and a polypeptide, preferably an antibody, modified to include an azide group.

Example 20

Compound 88

This example describes the synthesis of compound 88, which has an alkyl primary amine functionality that can be used for conjugation. Reference is made to the synthetic scheme of FIG. 24.

Compound 82.

A mixture of tert-butyl 1-amino-3,6,9,12-tetraoxapentadecan-15-oate 54 (0.285 g, 0.888 mmol, purchased from VWR; see also Example 8) and 2,5-dioxo-pyrrolidin-1-yl 6-((((9H-fluoren-9-yl)methoxy)carbonyl)amino)hexanoate 81 (0.4 g, 0.888 mmol, purchased from Chem-Impex) in DMF (3 mL) was stirred at RT for 2 h. The solvent was evaporated. The crude product was purified by flash chromatography eluting from silica gel with a gradient of 0-10% MeOH in DCM to afford 0.4 g of compound 82 as a white solid. MS: (+) m/z 657.4 (M+1).

Compound 83.

A mixture of compound 82 (0.258 g, 0.393 mmol) in TFA (2 mL, 0.393 mmol) was stirred at RT for 1 h. The solvent was evaporated. Compound 83 (white solid) was washed twice with hexanes and used for the next step reaction without further purification.

Compound 84.

DCC (0.162 g, 0.786 mmol) was added to a mixture of compound 83 (0.236 g, 0.393 mmol) and NHS (0.090 g, 0.786 mmol) in DCM (5 mL) at RT. After the reaction mixture was stirred at RT overnight, the solid was filtered off, and the filtrate concentrated. The crude product was purified by flash chromatography eluting from silica gel with a gradient of 0-100% EtOAc in hexanes to afford 0.195 g of compound 84 as a colorless oil. MS: (+) m/z 698.3 (M+1).

Compound 85.

DIEA was added to a solution of compound 21 (0.162 g, 0.279 mmol) and compound 84 (0.195 g, 0.279 mmol) in DMF (1.5 mL) at RT. After the reaction mixture was stirred at RT for 1 h, the reaction was quenched by addition of 6 mL of 1:1 mixture of acetonitrile and water containing 0.1% TFA. The crude product was purified by preparative HPLC to afford 0.292 g of compound 85 as a white solid. MS: (+) m/z 1161.6 (M+1).

Compound 86.

TFA (0.5 mL) was added to a mixture of compound 85 (22.1 mg, 0.019 mmol) in DCM (1 mL) at RT. After the reaction mixture was stirred at RT for 20 min, the solvent was evaporated to afford compound 86. MS: (+) m/z 1061.6 (M+1).

Compound 87.

DIEA was added to a solution of compound 9 (10.53 mg, 0.019 mmol) and HATU (7.23 mg, 0.019 mmol) in DMF (0.4 mL). The pH of the reaction mixture was adjusted to 8-9. After the reaction mixture was stirred at RT for 10 min, compound 86 (20.19 mg, 0.019 mmol) in DMF (1 mL) and DIEA were added. The pH of the reaction solution was adjusted to 8-9. After the reaction mixture was stirred at RT for 10 min, LCMS showed the reaction went to completion. The reaction was quenched by addition of 10 mL of a 1:1 (v/v) mixture of water (0.1% TFA) and acetonitrile. The crude product was purified by preparative HPLC to afford 27.3 mg of compound 87 as a white solid. MS: (+) m/z 799.1 (M/2+1).

Compound 88.

Piperidine was added to a solution of compound 87 (27.3 mg, 0.017 mmol) in DMF (2 mL) at RT, adjusting the pH to 9-10. After the reaction mixture was stirred at RT for 1 h, the reaction was quenched by addition of 6 mL of a 1:1 mixture of acetonitrile and water containing 0.1% TFA. The crude product was purified by preparative HPLC to afford 22.5 mg of compound 88 as a white solid. MS: (+) m/z 688.1 (M/2+1). Compound 88 is also referred to hereinabove as compound (III-13).

In one embodiment, there is provided a conjugate in which compound 88 is conjugated to a polypeptide, which preferably is an antibody, via amide formation between the alkyl primary amine of compound 88 and a carboxyl group on a side chain residue of an amino acid—preferably glutamic acid—in the polypeptide. This invention also provides a method of making such a conjugate, comprising combining compound 88 and the polypeptide in the presence of the enzyme transglutaminase.

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the references cited in abbreviated fashion by first author (or inventor) and date earlier in this specification are provided below. Each of these references is incorporated herein by reference for all purposes. The citation of a reference hereinbelow or elsewhere in this specification is not an admission that such reference is material prior art.

Abe et al., WO 97/21712 (1997).
Boyd et al., US 2008/0279868 A1 (2008).
Boyd et al., U.S. Pat. No. 7,691,962 B2 (2010).
Balasubramanian et al., Bioorg. Med. Chem. Lett. 2008, 18, 2996-2999.
Balasubramanian et al., J. Med. Chem. 2009, 52 (2), 238-240.
Chai et al., Chem. & Biol. 2010, 17(3), 296-309.
Chai et al., US 2011/0245295 A1 (2011).
Cheng et al., US 2011/0027274 A1 (2011).
Coccia et al., US 2010/0150950 (2010)
Davis et al., US 2008/0176958 A1 (2008).
Domling, DE 10 2004 030 227 A1 (2006).
Domling et al., US 2005/0239713 A1 (2005) [2005a].
Domling et al., US 2005/0249740 A1 (2005) [2005b].
Domling et al., Mol. Diversity 2005, 9, 141-147 [2005c].
Domling et al., Ang. Chem. Int. Ed. 2006, 45, 7235-7239.
Ellman et al., U.S. Pat. No. 8,476,451 B2 (2013).
Hamel et al., Curr. Med. Chem.—Anti-Cancer Agents 2002, 2, 19-53.
Hoefle et al., DE 100 08 089 A1 (2001).
Hoefle et al., Pure Appl. Chem. 2003, 75 (2-3), 167-178.
Hoefle et al., US 2006/0128754 A1 (2006) [2006a].
Hoefle et al., US 2006/0217360 A1 (2006) [2006b].
Jackson et al., US 2013/0224228 A1 (2013).
Kaur et al., Biochem. J. 2006, 396, 235-242.
Khalil et al., Chem Bio Chem 2006, 7, 678-683.
Leamon et al., Cancer Res. 2008, 68 (23), 9839-9844.
Leamon et al., US 2010/0323973 A1 (2010).
Leung et al., US 2002/0169125 A1 (2002).
Low et al., US 2010/0324008 A1 (2010).
Lundquist et al., Org. Lett. 2001, 3, 781-783.
Neri et al., Chem Med Chem 2006, 1, 175-180.
Pando et al., J. Am. Chem. Soc., 2011, 133, 7692-7696.
Patterson et al., Chem. Eur. J 2007, 13, 9534-9541.
Patterson et al., J. Org. Chem. 2008, 73, 4362-4369.
Peltier et al., J. Am. Chem. Soc. 2006, 128, 16018-16019.
Reddy et al., Mol. Pharmaceutics 2009, 6 (5), 1518-1525.
Reichenbach et al. WO 98/13375 A1 (1998).
Richter, US 2012/0129779 A1 (2012) [2012a]
Richter, US 2012/0252738 A1 (2012) [2012b].
Richter, US 2012/0252739 A1 (2012) [2012c].
Sani et al., Angew. Chem. Int. Ed. 2007, 46, 3526-3529.
Sasse et al., J. Antibiotics 2000, 53 (9), 879-885.
Sasse et al., Nature Chem. Biol. 2007, 3 (2), 87-89.
Schluep et al., Clin. Cancer Res. 2009, 15 (1), 181-189.
Schrama et al., Nature Rev. Drug Disc. 2006, 5, 147-159.
Shankar et al., SYNLETT 2009, 8, 1341-1345.
Shankar et al., Org. Biomol. Chem., 2013, 11(14), 2273-2287.
Shibue et al., Tetrahedron Lett. 2009, 50, 3845-3848.
Shibue et al., Chemistry Eur. J, 2010, 16(38), 11678-11688.
Shibue et al., Bioorg. Med. Chem., 2011, 21, 431-434.
Sreejith et al., SYNLETT 2011, No. 12, 1673-1676x.
Steinmetz et al., Angew. Chem. Int. Ed. 2004, 43, 4888-4892.
Terrett et al., U.S. Pat. No. 8,268,970 B2 (2012).
Terrette et al., US 2010/0209432 A1 (2010).
Ullrich et al., Angew. Chemie Int. Ed. 2009, 48, 4422-4425.
Vlahov et al., Bioorg. Med. Chem. Lett. 2008, 18 (16), 4558-4561 [2008a].
Vlahov et al., US 2008/0248052 A1 (2008) [2008b].
Vlahov et al., US 2010/0240701 A1 (2010) [2010a].
Vlahov et al., US 2010/0048490 A1 (2010) [2010b].
Wang et al., Chem. Biol. Drug. Des 2007, 70, 75-86.
Wipf et al., Org. Lett. 2004, 6 (22), 4057-4060.
Wipf et al., Org. Lett. 2007, 9 (8), 1605-1607.
Wipf et al., US 2010/0047841 A1 (2010).
Zanda et al., U.S. Pat. No. 8,580,820 B2 (2013).

TABLE OF SEQUENCES

The following Table 3 summarizes the descriptions of the sequences disclosed in this application.

TABLE 3

| Sequence Summary | |
|---|---|
| SEQ ID NO: | SEQUENCE DESCRIPTION |
| 1 | 6A4 $V_H$ CDR1 amino acid |
| 2 | 6A4 $V_H$ CDR2 amino acid |

TABLE 3-continued

Sequence Summary

| SEQ ID NO: | SEQUENCE DESCRIPTION |
|---|---|
| 3 | 6A4 $V_H$ CDR3 amino acid |
| 4 | 6A4 $V_K$ CDR1 amino acid |
| 5 | 6A4 $V_K$ CDR2 amino acid |
| 6 | 6A4 $V_K$ CDR3 amino acid |
| 7 | 6A4 $V_H$ amino acid |
| 8 | 6A4 $V_K$ amino acid |
| 9 | 1F4 $V_H$ CDR1 amino acid |
| 10 | 1F4 $V_H$ CDR2 amino acid |
| 11 | 1F4 $V_H$ CDR3 amino acid |
| 12 | 1F4 $V_K$ CDR1 amino acid |
| 13 | 1F4 $V_K$ CDR2 amino acid |
| 14 | 1F4 $V_K$ CDR3 amino acid |
| 15 | 1F4 $V_H$ amino acid |
| 16 | 1F4 $V_K$ amino acid |
| 17 | 4A6 $V_H$ CDR1 amino acid |
| 18 | 4A6 $V_H$ CDR2 amino acid |
| 19 | 4A6 $V_H$ CDR3 amino acid |
| 20 | 4A6 $V_K$ CDR1 amino acid |
| 21 | 4A6 $V_K$ CDR2 amino acid |
| 22 | 4A6 $V_K$ CDR3 amino acid |
| 23 | 4A6 $V_H$ amino acid |
| 24 | 4A6 $V_K$ amino acid |
| 25 | Modified antibody constant region |
| 26 | Modified antibody constant region |

SEQUENCE LISTING

```
<160> NUMBER OF SEQ ID NOS: 26

<210> SEQ ID NO 1
<211> LENGTH: 5
<212> TYPE: PRT
<213> ORGANISM: Homo sapiens

<400> SEQUENCE: 1

Ile Tyr Gly Met His
1               5

<210> SEQ ID NO 2
<211> LENGTH: 17
<212> TYPE: PRT
<213> ORGANISM: Homo sapiens

<400> SEQUENCE: 2

Val Leu Trp Tyr Asp Gly Ser His Glu Tyr Tyr Ala Asp Ser Val Lys
1               5                   10                  15

Gly

<210> SEQ ID NO 3
<211> LENGTH: 13
<212> TYPE: PRT
<213> ORGANISM: Homo sapiens

<400> SEQUENCE: 3

Asp Gly Asp Tyr Tyr Asp Ser Gly Ser Pro Leu Asp Tyr
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Asn Arg Ala Thr
```

```
<210> SEQ ID NO 6
<211> LENGTH: 9
<212> TYPE: PRT
<213> ORGANISM: Homo sapiens

<400> SEQUENCE: 6

Gln Gln Arg Ser Asn Trp Pro Leu Thr
1               5

<210> SEQ ID NO 7
<211> LENGTH: 122
<212> TYPE: PRT
<213> ORGANISM: Homo sapiens

<400> SEQUENCE: 7

Gln Val His Leu Val Glu Ser Gly Gly Gly Val Gln Pro Gly Arg
1               5                   10                  15

Ser Leu Arg Leu Ser Cys Val Ala Ser Gly Ile Thr Phe Arg Ile Tyr
                20                  25                  30

Gly Met His Trp Val Arg Gln Ala Pro Gly Lys Gly Leu Glu Trp Val
            35                  40                  45

Ala Val Leu Trp Tyr Asp Gly Ser His Glu Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Asp Gly Asp Tyr Tyr Asp Ser Gly Ser Pro Leu Asp Tyr Trp
            100                 105                 110

Gly Gln Gly Thr Leu Val Thr Val Ser Ser
            115                 120

<210> SEQ ID NO 8
<211> LENGTH: 107
<212> TYPE: PRT
<213> ORGANISM: Homo sapiens

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 9
<211> LENGTH: 5
<212> TYPE: PRT
<213> ORGANISM: Homo sapiens
```

<400> SEQUENCE: 9

Ile Tyr Ala Met Ser
1               5

<210> SEQ ID NO 10
<211> LENGTH: 17
<212> TYPE: PRT
<213> ORGANISM: Homo sapiens

<400> SEQUENCE: 10

Ala Ile Ser Asp Ser Gly Gly Arg Thr Tyr Phe Ala Asp Ser Val Arg
1               5                   10                  15

Gly

<210> SEQ ID NO 11
<211> LENGTH: 11
<212> TYPE: PRT
<213> ORGANISM: Homo sapiens

<400> SEQUENCE: 11

Val Asp Tyr Ser Asn Tyr Leu Phe Phe Asp Tyr
1               5                   10

<210> SEQ ID NO 12
<211> LENGTH: 12
<212> TYPE: PRT
<213> ORGANISM: Homo sapiens

<400> SEQUENCE: 12

Arg Ala Ser Gln Ser Ile Ser Ser Tyr Leu Ala
1               5                   10

<210> SEQ ID NO 13
<211> LENGTH: 7
<212> TYPE: PRT
<213> ORGANISM: Homo sapiens

<400> SEQUENCE: 13

Gly Ala Ser Ser Arg Ala Thr
1               5

<210> SEQ ID NO 14
<211> LENGTH: 9
<212> TYPE: PRT
<213> ORGANISM: Homo sapiens

<400> SEQUENCE: 14

Gln Gln Tyr Gly Ser Ser Pro Tyr Thr
1               5

<210> SEQ ID NO 15
<211> LENGTH: 120
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

```
Ser Ala Ile Ser Asp Ser Gly Gly Arg Thr Tyr Phe Ala Asp Ser Val
        50                  55                  60

Arg Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Val Asp Tyr Ser Asn Tyr Leu Phe Phe Asp Tyr Trp Gly Gln
            100                 105                 110

Gly Thr Leu Val Thr Val Ser Ser
            115                 120

<210> SEQ ID NO 16
<211> LENGTH: 108
<212> TYPE: PRT
<213> ORGANISM: Homo sapiens

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

<210> SEQ ID NO 17
<211> LENGTH: 5
<212> TYPE: PRT
<213> ORGANISM: Homo sapiens

<400> SEQUENCE: 17

Ser Tyr Trp Ile Ala
1               5

<210> SEQ ID NO 18
<211> LENGTH: 17
<212> TYPE: PRT
<213> ORGANISM: Homo sapiens

<400> SEQUENCE: 18

Ile Ile Phe Pro Gly Asp Ser Asp Thr Arg Tyr Ser Pro Ser Phe Gln
1               5                   10                  15

Gly

<210> SEQ ID NO 19
<211> LENGTH: 8
<212> TYPE: PRT
<213> ORGANISM: Homo sapiens

<400> SEQUENCE: 19

Thr Arg Glu Gly Tyr Phe Asp Tyr
1               5
```

<210> SEQ ID NO 20
<211> LENGTH: 12
<212> TYPE: PRT
<213> ORGANISM: Homo sapiens

<400> SEQUENCE: 20

Arg Ala Val Gln Ser Val Ser Ser Tyr Leu Ala
1               5                   10

<210> SEQ ID NO 21
<211> LENGTH: 7
<212> TYPE: PRT
<213> ORGANISM: Homo sapiens

<400> SEQUENCE: 21

Gly Ala Ser Ser Arg Ala Thr
1               5

<210> SEQ ID NO 22
<211> LENGTH: 8
<212> TYPE: PRT
<213> ORGANISM: Homo sapiens

<400> SEQUENCE: 22

Gln Gln Tyr Gly Ser Ser Pro Thr
1               5

<210> SEQ ID NO 23
<211> LENGTH: 117
<212> TYPE: PRT
<213> ORGANISM: Homo sapiens

<400> SEQUENCE: 23

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Ala Trp Val Arg Gln Met Pro Gly Lys Gly Leu Glu Trp Met
            35                  40                  45

Gly Ile Ile Phe Pro Gly Asp Ser Asp Thr Arg Tyr Ser Pro Ser Phe
        50                  55                  60

Gln Gly Gln Val Thr Ile Ser Ala Asp Arg Ser Ile Arg Thr Ala Tyr
65                  70                  75                  80

Leu Gln Trp Ser Ser Leu Lys Ala Ser Asp Thr Ala Leu Tyr Tyr Cys
                85                  90                  95

Ala Arg Thr Arg Glu Gly Tyr Phe Asp Tyr Trp Gly Gln Gly Thr Leu
            100                 105                 110

Val Thr Val Ser Ser
        115

<210> SEQ ID NO 24
<211> LENGTH: 107
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Val Gln Ser Val Ser Ser Ser
                20                  25                  30

```
Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Thr Phe Gly Gly Gly Thr Lys Val Glu Ile Lys
                100                 105

<210> SEQ ID NO 25
<211> LENGTH: 327
<212> TYPE: PRT
<213> ORGANISM: Artificial Sequence
<220> FEATURE:
<223> OTHER INFORMATION: Modified Antibody Constant Region

<400> SEQUENCE: 25

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Ala Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 26
<211> LENGTH: 330
<212> TYPE: PRT
<213> ORGANISM: Artificial Sequence
<220> FEATURE:
<223> OTHER INFORMATION: Modified Antibody Constant Region

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Asp Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Glu Gly Asn
    290                 295                 300

Gln Lys Ser Leu Ser Leu Ser Leu Gly Lys
            325                 330
What is claimed is:
1. A compound having a structure represented by formula (I-2):
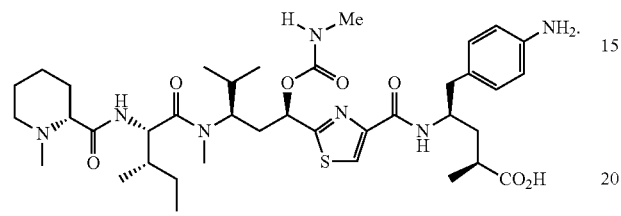

Val Phe Ser Cys Ser Val Met His Glu Ala Leu His Asn His Tyr Thr
305                 310                 315                 320
```